(12) United States Patent
Okazaki et al.

(10) Patent No.: US 12,234,289 B2
(45) Date of Patent: Feb. 25, 2025

(54) IMMUNOSUPPRESIVE AGENT

(71) Applicants: ONO PHARMACEUTICAL CO., LTD., Osaka (JP); TOKUSHIMA UNIVERSITY, Tokushima (JP)

(72) Inventors: Taku Okazaki, Tokushima (JP); Daisuke Sugiura, Tokushima (JP); Takeo Maeda, Tokushima (JP); Shiro Shibayama, Ibaraki (JP)

(73) Assignees: ONO PHARMACEUTICAL CO., LTD., Osaka (JP); TOKUSHIMA UNIVERSITY, Tokushima (JP)

( * ) Notice: Subject to any disclaimer, the term of this patent is extended or adjusted under 35 U.S.C. 154(b) by 857 days.

(21) Appl. No.: 17/311,148

(22) PCT Filed: Dec. 6, 2019

(86) PCT No.: PCT/JP2019/047913
§ 371 (c)(1),
(2) Date: Jun. 4, 2021

(87) PCT Pub. No.: WO2020/116636
PCT Pub. Date: Jun. 11, 2020

(65) Prior Publication Data
US 2022/0025051 A1    Jan. 27, 2022

(30) Foreign Application Priority Data

Dec. 7, 2018  (JP) ................. 2018-229774

(51) Int. Cl.
| | | |
|---|---|---|
| C07K 16/28 | (2006.01) | |
| A61K 39/00 | (2006.01) | |
| A61P 37/06 | (2006.01) | |

(52) U.S. Cl.
CPC .......... *C07K 16/2827* (2013.01); *A61P 37/06* (2018.01); *A61K 2039/505* (2013.01); *C07K 2317/92* (2013.01)

(58) Field of Classification Search
CPC ........... C07K 16/2827; C07K 2317/92; C07K 2319/20; A61P 37/06; A61P 37/08; A61K 2039/505
See application file for complete search history.

(56) References Cited

FOREIGN PATENT DOCUMENTS

| | | |
|---|---|---|
| JP | 11-508764 A | 8/1999 |
| JP | 2012-517406 A | 8/2012 |
| WO | 96/40878 A1 | 12/1996 |
| WO | 2010/089411 A2 | 8/2010 |
| WO | 2015/048520 A1 | 4/2015 |

OTHER PUBLICATIONS

Rosenblum, M.D., et al.(2015) Mechanisms of human autoimmunity J Clin Invest 125(6); 2228-2233 (Year: 2015).*

(Continued)

*Primary Examiner* — Scarlett Y Goon
*Assistant Examiner* — Audrey L Buttice
(74) *Attorney, Agent, or Firm* — Sughrue Mion, PLLC

(57) ABSTRACT

An immunosuppressive agent containing a substance that is selected from anti-CD80 antibodies and anti-PD-L1 antibodies and that promotes binding between PD-L1 and PD-1.

12 Claims, 30 Drawing Sheets
Specification includes a Sequence Listing.

(56) References Cited

OTHER PUBLICATIONS

Royal, C. and C. Gray (2020) Allergy Prevention: an overview of current evidence Yale Journal of Biology and Medicine 93; 689-698 (Year: 2020).*

Lee, C., et al.(2018) Prediction of absolute risk of acute graft versus host disease following hematopoietic cell transplantation PLoS ONE 13(1): e0190610, 1-16 (Year: 2018).*

Chan, B.M., et al.(2018) Flow cytometry-based epitope binning using competitive binding profiles for the characterization of monoclonal antibodies against cellular and soluble protein targets SLAS Discovery 23(7); 613-623 (Year: 2018).*

Hummer, A.M., et al.(2022) Advances in computational structure-based antibody design Current Opinion in Structural Biology 74(102379); 1-7 (Year: 2022).*

Smith et al., "The anti-CD80 primatized monoclonal antibody, galiximab, is well-tolerated but has limited activity in relapsed Hodgkin lymphoma: Cancer and Leukemia Group B 50602 (Alliance)," Leuk Lymphoma, vol. 54, No. 7, pp. 1405-1410, XP055959000, Jul. 2013, Total 15 pages.

Butte, et al., "Interaction of human PD-L1 and B7-1", 2008, Molecular Immunology, vol. 45, Issue 13, 6 pages total, XP022849591.

Butte, et al., "PD-L1 interacts specifically with B7-1 to inhibit T cell proliferation", 2007, Immunity, vol. 27, Issue 1, 22 pages total, XP055555055.

Chaudhri et al., "PD-L1 Binds to B7-1 Only In Cis on the Same Cell Surface," American Association for Cancer Research, Cancer Immunology Research, vol. 6, Jun. 5, 2018, pp. 921-929, Total 10 pages, DOI: 10.1158/2326-6066.

Sugiura et al., "Restriction of PD-1 function by cis-PD-L1/CD80 interactions is required for optimal T cell responses," Science, vol. 364 (6440), May 10, 2019, pp. 558-566, Total 10 pages, DOI: 10.1126/science.aav7062.

International Search Report (PCT/ISA/210) dated Mar. 3, 2020, issued by the International Searching Authority in counterpart International Application No. PCT/JP2019/047913.

Written Opinion (PCT/ISA/237) dated Mar. 3, 2020, issued by the International Searching Authority in counterpart International Application No. PCT/JP2019/047913.

* cited by examiner

Fig. 1
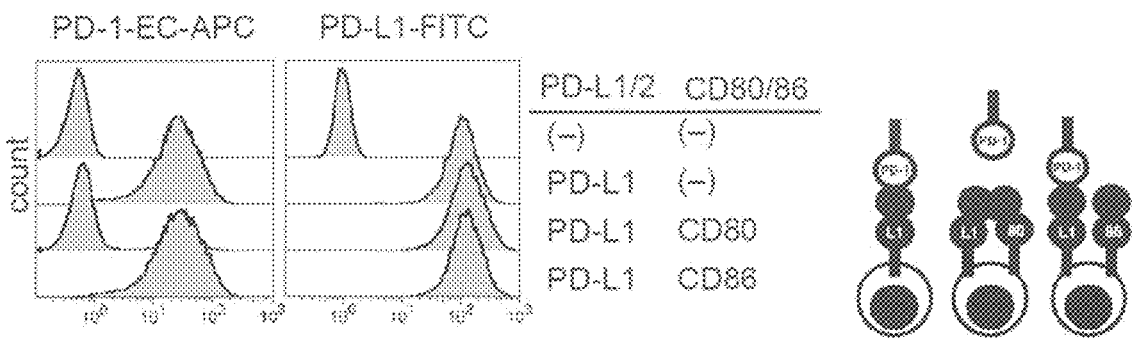
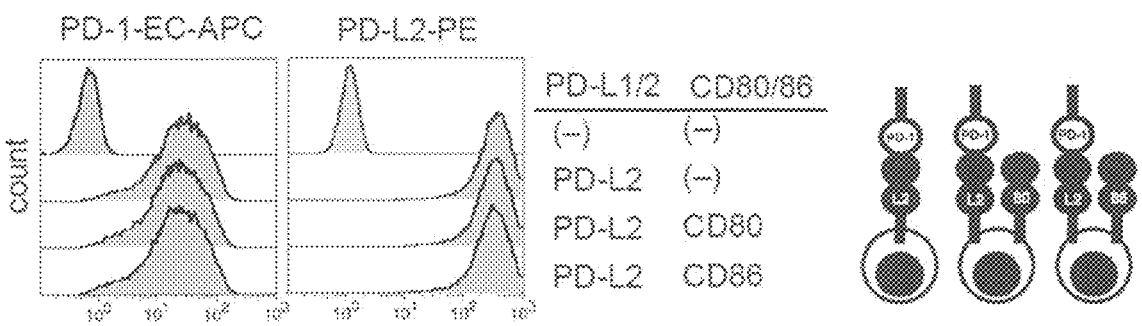
Fig. 2
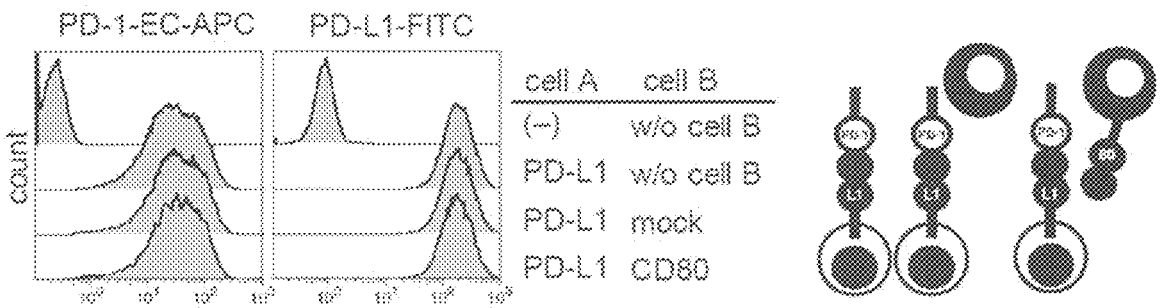

PD-1-EC binding (%)

Reduction of IL-2 (%)

Fig. 15
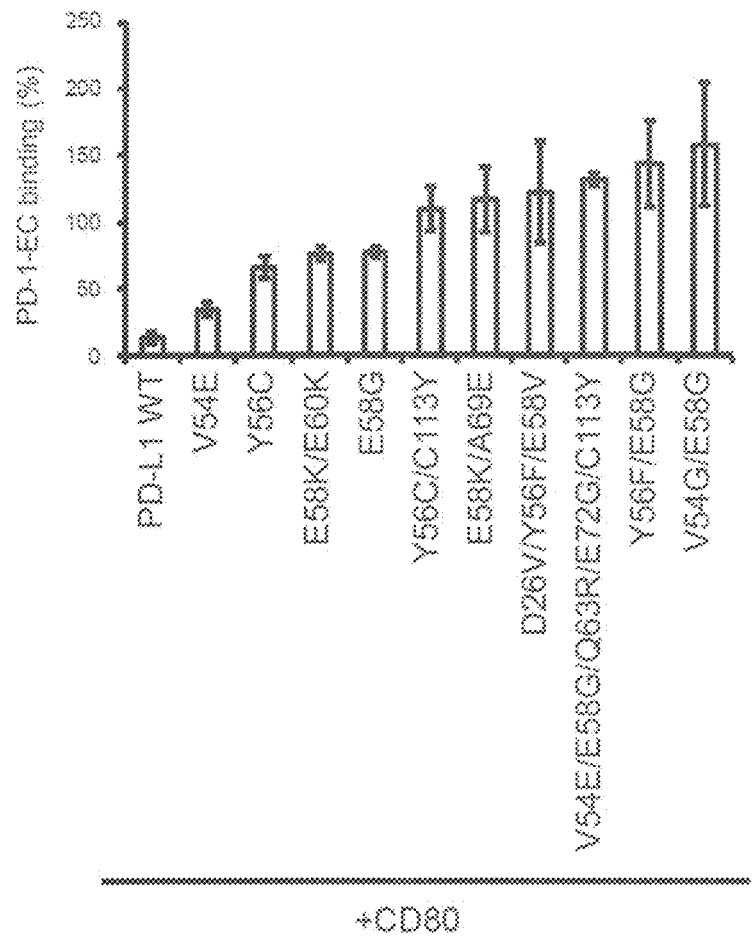
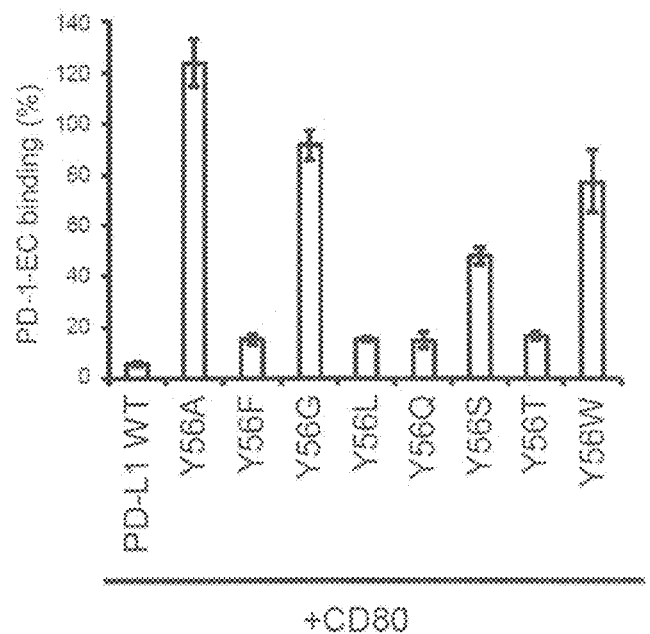

hCD80
(PDB ID:1DR9)

hCD86
(PDB ID:1NCN)

Fig. 24
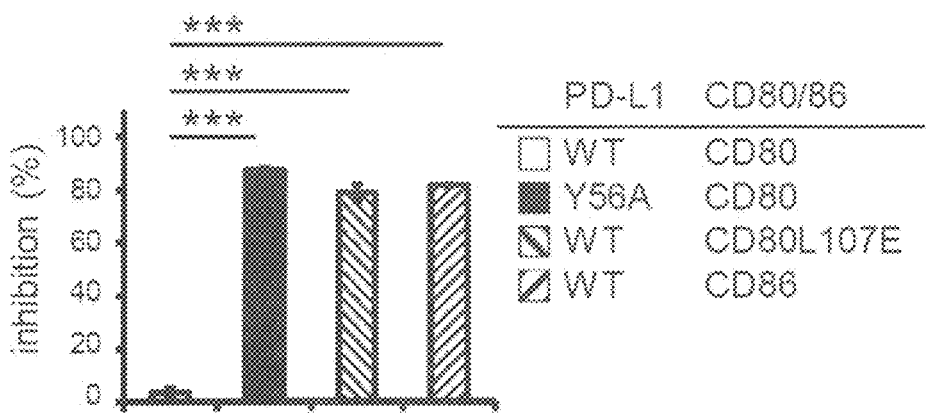
Fig. 25
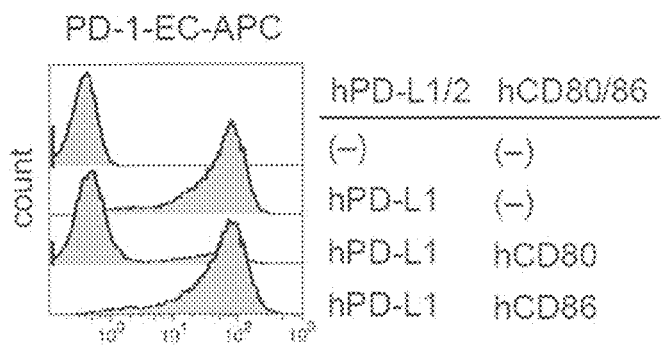
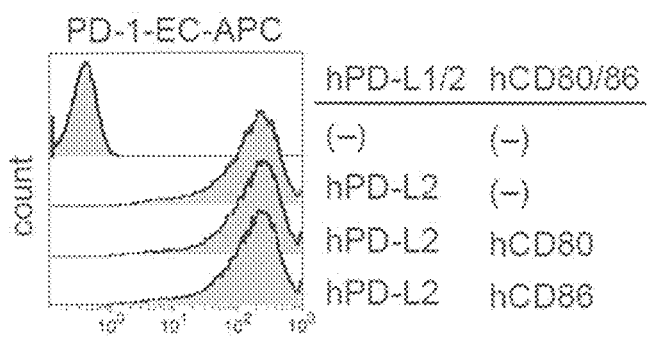
Fig. 26
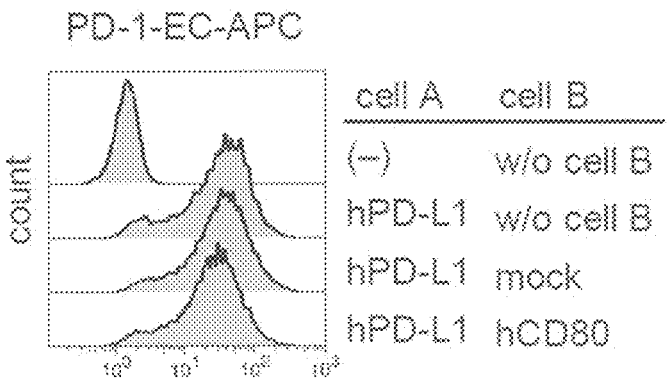

Fig. 29
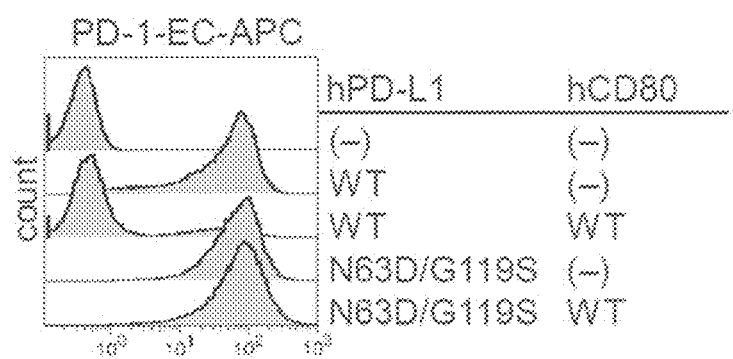
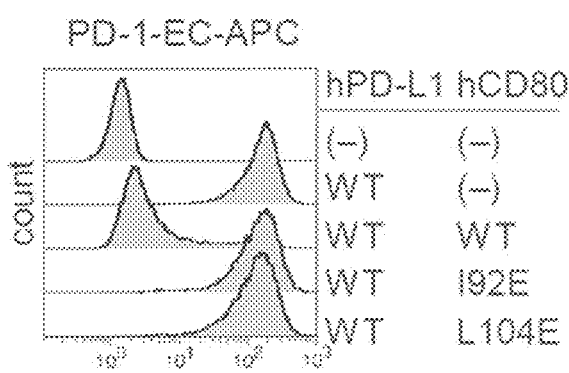

days after tumor inoculation

Fig. 47
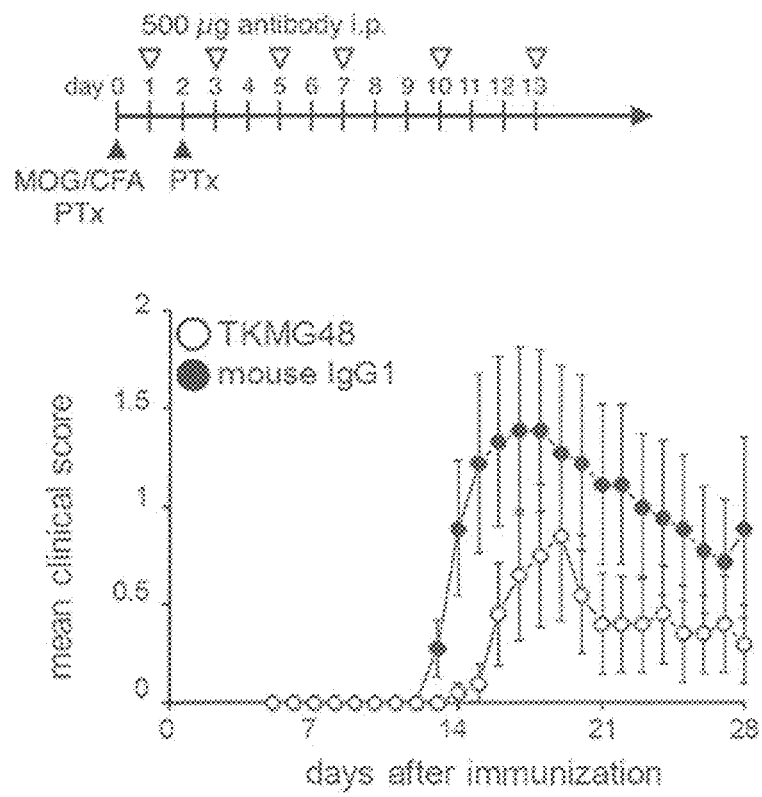
Fig. 48
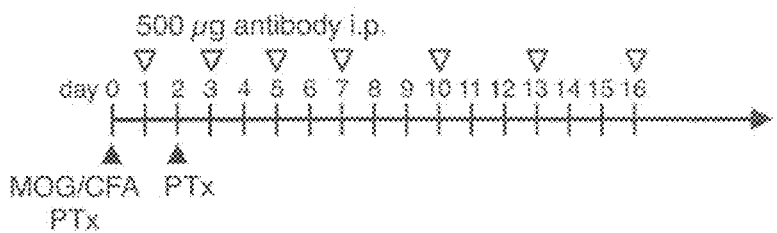
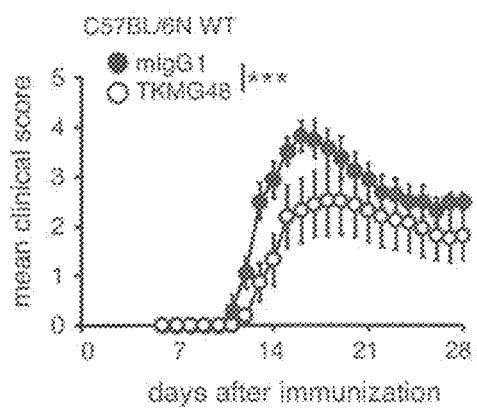
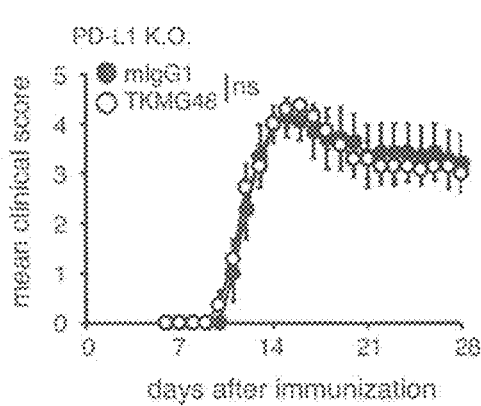

Fig. 51

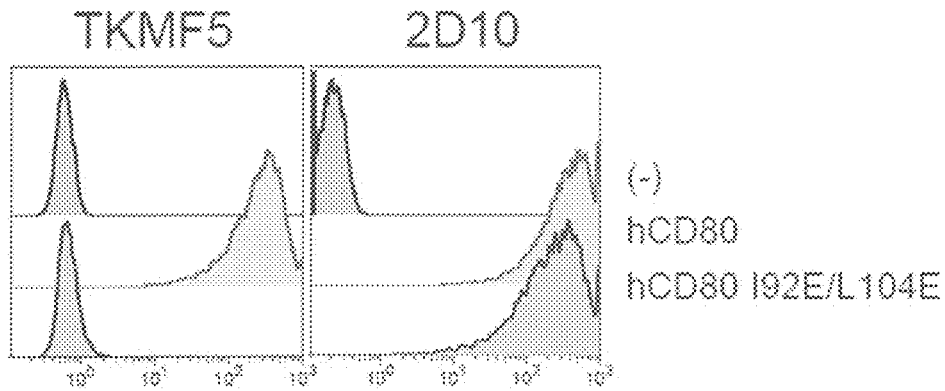

Fig. 52

Amino acid sequence of anti-human CD80 antibody TKMF5

Heavy chain variable region (SEQ ID NO: 7)
QVQLQQSGAELVRPGSSVKISCKASGYAFSYYWMNWVKQRPGQGLEWIGQIYPGDGDTNYNGKFKGKATL
                              CDR1 (SEQ ID NO: 9)      CDR2 (SEQ ID NO: 10)

TADKSSSTAYMQLSSLTSEDSAVYFCARSYGNTMDYWGQGTSVTVSS
                            CDR3 (SEQ ID NO: 11)

Light chain variable region (SEQ ID NO: 8)
DIVMTQSQKFMSTSVGDRVSITCKAGQNVRTAVAWYQQKPGQSPKTLIYLASNRHTGVPDRFTGSGSGTD
                          CDR1 (SEQ ID NO: 12)       CDR2 (SEQ ID NO: 13)

FTLTISNVQSEDLADYFCLQHWNYPFTFGSGTKLEIK
                  CDR3 (SEQ ID NO: 14)

Fig. 53

Amino acid sequence of anti-mouse CD80 antibody TKMG48

Heavy chain variable region (SEQ ID NO: 15)
QVQLQQPGAELVRPGSSVKLSCKASGYTFTSYWMHWVKQRPGQGLEWIGNIDPSDSETHYNQKFKDKATL
　　　　　　　　　　　　　　　　CDR1 (SEQ ID NO: 17)　　CDR2 (SEQ ID NO: 18)

TVDKSSSTAYMQLSSLTSEDSAVYYCARSYYYGTRYYAMDYWGQGTSVTVSS
　　　　　　　　　　　　　　　CDR3 (SEQ ID NO: 19)

Light chain variable region (SEQ ID NO: 16)
DIQMTQSPSSLSASLGGKVTITCKASQDINKYIAWYQHKPGKGPRLLIHYTSTLQPGIPSRFSGSGSGRD
　　　　　　　　　　　　CDR1 (SEQ ID NO: 20)　　　CDR2 (SEQ ID NO: 21)

YSFSISNLEPEDIATYYCLQYDNLLTFGGGTKLEIK
　　　　　　　　　CDR3 (SEQ ID NO: 22)

SEQUENCE LISTING

<160> NUMBER OF SEQ ID NOS: 44

<210> SEQ ID NO 1
<211> LENGTH: 288
<212> TYPE: PRT
<213> ORGANISM: Homo sapiens

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 2
<211> LENGTH: 306
<212> TYPE: PRT
<213> ORGANISM: Mus musculus

<400> SEQUENCE: 2

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp

```
            35                  40                  45
Lys Val Leu Leu Pro Cys Arg Tyr Asn Ser Pro His Glu Asp Glu Ser
 50                  55                  60

Glu Asp Arg Ile Tyr Trp Gln Lys His Asp Lys Val Val Leu Ser Val
 65                  70                  75                  80

Ile Ala Gly Lys Leu Lys Val Trp Pro Glu Tyr Lys Asn Arg Thr Leu
                 85                  90                  95

Tyr Asp Asn Thr Thr Tyr Ser Leu Ile Ile Leu Gly Leu Val Leu Ser
                100                 105                 110

Asp Arg Gly Thr Tyr Ser Cys Val Val Gln Lys Lys Glu Arg Gly Thr
                115                 120                 125

Tyr Glu Val Lys His Leu Ala Leu Val Lys Leu Ser Ile Lys Ala Asp
                130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
                180                 185                 190

Ser Gln Asp Pro Glu Ser Glu Leu Tyr Thr Ile Ser Ser Gln Leu Asp
                195                 200                 205

Phe Asn Thr Thr Arg Asn His Thr Ile Lys Cys Leu Ile Lys Tyr Gly
                210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
                260                 265                 270

Lys His Arg Ser Cys Phe Arg Arg Asn Glu Ala Ser Arg Glu Thr Asn
                275                 280                 285

Asn Ser Leu Thr Phe Gly Pro Glu Glu Ala Leu Ala Glu Gln Thr Val
                290                 295                 300

Phe Leu
305

<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
                 35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95
```

```
Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 4
<211> LENGTH: 290
<212> TYPE: PRT
<213> ORGANISM: Mus musculus

<400> SEQUENCE: 4

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175
```

```
Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
        210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
    290

<210> SEQ ID NO 5
<211> LENGTH: 288
<212> TYPE: PRT
<213> ORGANISM: Homo sapiens

<400> SEQUENCE: 5

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
```

```
                        245                 250                 255
Met Gly Thr Ser Ser Pro Ala Arg Arg Gly Ser Ala Asp Gly Pro Arg
                    260                 265                 270

Ser Ala Gln Pro Leu Arg Pro Glu Asp Gly His Cys Ser Trp Pro Leu
                275                 280                 285
```

<210> SEQ ID NO 6
<211> LENGTH: 288
<212> TYPE: PRT
<213> ORGANISM: Mus musculus

<400> SEQUENCE: 6

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285
```

<210> SEQ ID NO 7
<211> LENGTH: 117
<212> TYPE: PRT
<213> ORGANISM: Homo sapiens

<400> SEQUENCE: 7

```
Gln Val Gln Leu Gln Gln Ser Gly Ala Glu Leu Val Arg Pro Gly Ser
```

```
                 1               5                  10                 15
              Ser Val Lys Ile Ser Cys Lys Ala Ser Gly Tyr Ala Phe Ser Tyr Tyr
                             20                  25                 30

Trp Met Asn Trp Val Lys Gln Arg Pro Gly Gln Gly Leu Glu Trp Ile
                         35                  40                  45

Gly Gln Ile Tyr Pro Gly Asp Gly Asp Thr Asn Tyr Asn Gly Lys Phe
                     50                  55                  60

Lys Gly Lys Ala Thr Leu Thr Ala Asp Lys Ser Ser Ser Thr Ala Tyr
               65                  70                  75                  80

Met Gln Leu Ser Ser Leu Thr Ser Glu Asp Ser Ala Val Tyr Phe Cys
                             85                  90                  95

Ala Arg Ser Tyr Gly Asn Thr Met Asp Tyr Trp Gly Gln Gly Thr Ser
                            100                 105                 110

Val Thr Val Ser Ser
                            115

<210> SEQ ID NO 8
<211> LENGTH: 107
<212> TYPE: PRT
<213> ORGANISM: Homo sapiens

<400> SEQUENCE: 8

Asp Ile Val Met Thr Gln Ser Gln Lys Phe Met Ser Thr Ser Val Gly
               1               5                  10                  15

Asp Arg Val Ser Ile Thr Cys Lys Ala Gly Gln Asn Val Arg Thr Ala
                             20                  25                  30

Val Ala Trp Tyr Gln Gln Lys Pro Gly Gln Ser Pro Lys Thr Leu Ile
                         35                  40                  45

Tyr Leu Ala Ser Asn Arg His Thr Gly Val Pro Asp Arg Phe Thr Gly
                     50                  55                  60

Ser Gly Ser Gly Thr Asp Phe Thr Leu Thr Ile Ser Asn Val Gln Ser
               65                  70                  75                  80

Glu Asp Leu Ala Asp Tyr Phe Cys Leu Gln His Trp Asn Tyr Pro Phe
                             85                  90                  95

Thr Phe Gly Ser Gly Thr Lys Leu Glu Ile Lys
                            100                 105

<210> SEQ ID NO 9
<211> LENGTH: 5
<212> TYPE: PRT
<213> ORGANISM: Homo sapiens

<400> SEQUENCE: 9

Tyr Tyr Trp Met Asn
               1               5

<210> SEQ ID NO 10
<211> LENGTH: 17
<212> TYPE: PRT
<213> ORGANISM: Homo sapiens

<400> SEQUENCE: 10

Gln Ile Tyr Pro Gly Asp Gly Asp Thr Asn Tyr Asn Gly Lys Phe Lys
               1               5                  10                  15

Gly

<210> SEQ ID NO 11
<211> LENGTH: 8
```

<212> TYPE: PRT
<213> ORGANISM: Homo sapiens

<400> SEQUENCE: 11

Ser Tyr Gly Asn Thr Met Asp Tyr
1               5

<210> SEQ ID NO 12
<211> LENGTH: 11
<212> TYPE: PRT
<213> ORGANISM: Homo sapiens

<400> SEQUENCE: 12

Lys Ala Gly Gln Asn Val Arg Thr Ala Val Ala
1               5                   10

<210> SEQ ID NO 13
<211> LENGTH: 7
<212> TYPE: PRT
<213> ORGANISM: Homo sapiens

<400> SEQUENCE: 13

Leu Ala Ser Asn Arg His Thr
1               5

<210> SEQ ID NO 14
<211> LENGTH: 9
<212> TYPE: PRT
<213> ORGANISM: Homo sapiens

<400> SEQUENCE: 14

Leu Gln His Trp Asn Tyr Pro Phe Thr
1               5

<210> SEQ ID NO 15
<211> LENGTH: 122
<212> TYPE: PRT
<213> ORGANISM: Mus musculus

<400> SEQUENCE: 15

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Ile Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Tyr Tyr Gly Thr Arg Tyr Tyr Ala Met Asp Tyr Trp
                100                 105                 110

Gly Gln Gly Thr Ser Val Thr Val Ser Ser
            115                 120

<210> SEQ ID NO 16
<211> LENGTH: 106
<212> TYPE: PRT
<213> ORGANISM: Mus musculus

<400> SEQUENCE: 16

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Thr
                85                  90                  95

Phe Gly Gly Gly Thr Lys Leu Glu Ile Lys
            100                 105

<210> SEQ ID NO 17
<211> LENGTH: 5
<212> TYPE: PRT
<213> ORGANISM: Mus musculus

<400> SEQUENCE: 17

Ser Tyr Trp Met His
1               5

<210> SEQ ID NO 18
<211> LENGTH: 17
<212> TYPE: PRT
<213> ORGANISM: Mus musculus

<400> SEQUENCE: 18

Asn Ile Asp Pro Ser Asp Ser Glu Thr His Tyr Asn Gln Lys Phe Lys
1               5                   10                  15

Asp

<210> SEQ ID NO 19
<211> LENGTH: 13
<212> TYPE: PRT
<213> ORGANISM: Mus musculus

<400> SEQUENCE: 19

Ser Tyr Tyr Tyr Gly Thr Arg Tyr Tyr Ala Met Asp Tyr
1               5                   10

<210> SEQ ID NO 20
<211> LENGTH: 11
<212> TYPE: PRT
<213> ORGANISM: Mus musculus

<400> SEQUENCE: 20

Lys Ala Ser Gln Asp Ile Asn Lys Tyr Ile Ala
1               5                   10

<210> SEQ ID NO 21
<211> LENGTH: 7
<212> TYPE: PRT
<213> ORGANISM: Mus musculus

<400> SEQUENCE: 21

Tyr Thr Ser Thr Leu Gln Pro
1               5

<210> SEQ ID NO 22
<211> LENGTH: 8
<212> TYPE: PRT
<213> ORGANISM: Mus musculus

<400> SEQUENCE: 22

Leu Gln Tyr Asp Asn Leu Leu Thr
1               5

<210> SEQ ID NO 23
<211> LENGTH: 20
<212> TYPE: DNA
<213> ORGANISM: Mus musculus

<400> SEQUENCE: 23
gtatggcagc aacgtcacga                                          20

<210> SEQ ID NO 24
<211> LENGTH: 20
<212> TYPE: DNA
<213> ORGANISM: Mus musculus

<400> SEQUENCE: 24
gacagtggca tctacctctg                                          20

<210> SEQ ID NO 25
<211> LENGTH: 20
<212> TYPE: DNA
<213> ORGANISM: Mus musculus

<400> SEQUENCE: 25
actcggcatt cgagcgaaac                                          20

<210> SEQ ID NO 26
<211> LENGTH: 20
<212> TYPE: DNA
<213> ORGANISM: Mus musculus

<400> SEQUENCE: 26
gctgttcacg cccttgtaca                                          20

<210> SEQ ID NO 27
<211> LENGTH: 20
<212> TYPE: DNA
<213> ORGANISM: Mus musculus

<400> SEQUENCE: 27
gttcagaaaa gatgtcagaa                                          20

<210> SEQ ID NO 28
<211> LENGTH: 20
<212> TYPE: DNA
<213> ORGANISM: Mus musculus

<400> SEQUENCE: 28
gtgctctcag acccattcca                                          20

<210> SEQ ID NO 29
<211> LENGTH: 20
<212> TYPE: DNA
<213> ORGANISM: Mus musculus

<400> SEQUENCE: 29
agaccctcca cagagagcac                                              20

<210> SEQ ID NO 30
<211> LENGTH: 20
<212> TYPE: DNA
<213> ORGANISM: Mus musculus

<400> SEQUENCE: 30
atgctaatgg ctgaagaatc                                              20

<210> SEQ ID NO 31
<211> LENGTH: 20
<212> TYPE: DNA
<213> ORGANISM: Mus musculus

<400> SEQUENCE: 31
gagacactat ctctaaaaat                                              20

<210> SEQ ID NO 32
<211> LENGTH: 20
<212> TYPE: DNA
<213> ORGANISM: Mus musculus

<400> SEQUENCE: 32
ttagtagagg tctccacctt                                              20

<210> SEQ ID NO 33
<211> LENGTH: 20
<212> TYPE: DNA
<213> ORGANISM: Mus musculus

<400> SEQUENCE: 33
gttcatgtga ttccctaaat                                              20

<210> SEQ ID NO 34
<211> LENGTH: 20
<212> TYPE: DNA
<213> ORGANISM: Mus musculus

<400> SEQUENCE: 34
ctgaagttgc tgtgctgagg                                              20

<210> SEQ ID NO 35
<211> LENGTH: 18
<212> TYPE: DNA
<213> ORGANISM: Mus musculus

<400> SEQUENCE: 35
tctgaaagga ccaggccc                                                18

<210> SEQ ID NO 36
<211> LENGTH: 18
<212> TYPE: DNA
<213> ORGANISM: Mus musculus

<400> SEQUENCE: 36
ttgcgttagt ggtgtact                                                18

<210> SEQ ID NO 37
<211> LENGTH: 82
<212> TYPE: DNA
<213> ORGANISM: Mus musculus -continued

```
<400> SEQUENCE: 37
ccctgtagaa cgggagctgg acctgcttgc gttagtggtg gcctgggaaa aggaagatga      60
gcaagtgatt cagtttgtgg ca                                              82

<210> SEQ ID NO 38
<211> LENGTH: 83
<212> TYPE: DNA
<213> ORGANISM: Mus musculus

<400> SEQUENCE: 38
ccggacttta tatgacaaca ctacctactc tcttatcatc gaaggcctgg tcctttcaga      60
ccggggcaca tacagctgtg tcg                                             83

<210> SEQ ID NO 39
<211> LENGTH: 17
<212> TYPE: PRT
<213> ORGANISM: Mus musculus

<400> SEQUENCE: 39

Ile Ser Gln Ala Val His Ala Ala His Ala Glu Ile Asn Glu Ala Gly
1               5                   10                  15

Arg

<210> SEQ ID NO 40
<211> LENGTH: 8
<212> TYPE: PRT
<213> ORGANISM: Mus musculus

<400> SEQUENCE: 40

Ser Ile Ile Asn Phe Glu Lys Leu
1               5

<210> SEQ ID NO 41
<211> LENGTH: 8
<212> TYPE: PRT
<213> ORGANISM: Artificial Sequence
<220> FEATURE:
<223> OTHER INFORMATION: FLAG tag

<400> SEQUENCE: 41

Asp Tyr Lys Asp Asp Asp Asp Lys
1               5

<210> SEQ ID NO 42
<211> LENGTH: 20
<212> TYPE: PRT
<213> ORGANISM: Homo sapiens

<400> SEQUENCE: 42

Ser His Ser Leu Gln Lys Tyr Tyr Ile Thr Gly Glu Ala Glu Gly Phe
1               5                   10                  15

Pro Ala Thr Ala
            20

<210> SEQ ID NO 43
<211> LENGTH: 21
<212> TYPE: PRT
<213> ORGANISM: Mus musculus

<400> SEQUENCE: 43

Met Glu Val Gly Trp Tyr Arg Ser Pro Phe Ser Arg Val Val His Leu
1               5                   10                  15
```

```
Tyr Arg Asn Gly Lys
            20

<210> SEQ ID NO 44
<211> LENGTH: 18
<212> TYPE: DNA
<213> ORGANISM: Mus musculus

<400> SEQUENCE: 44
ttgcgttagt ggtgtact                                                   18
```

IMMUNOSUPPRESIVE AGENT

CROSS-REFERENCE TO RELATED APPLICATIONS

This application is a National Phase Entry of PCT International Application No. PCT/JP2019/047913, filed on Dec. 6, 2019, which claims priority to Japanese Patent Application No. 2018-229774 filed on Dec. 7, 2018, the contents of all of which are incorporated herein by reference in their entirety.

TECHNICAL FIELD

This patent application claims the benefit of priority of Japanese Patent Application No. 2018-229774, the entire content of which is incorporated herein by reference.

The present application relates to an immunosuppressive agent containing a substance that promotes the binding of PD-L1 to PD-1 and is selected from an anti-CD80 antibody and an anti-PD-L1 antibody.

BACKGROUND ART

The immune system protects the living body from disease by recognizing and killing non-self substances such as pathogens and abnormal cells such as cancer cells in the body. The immune system is tightly regulated so that it attacks pathogens and abnormal cells and does not attack normal self-substances, but if the control mechanism is disrupted, various intractable diseases such as autoimmune diseases and chronic inflammatory diseases are caused.

Various molecules involved in the regulation of the immune system are known. Programmed death-1 (PD-1) is a type of immune checkpoint receptor on the surface of T cells, and it binds to two types of ligands, programmed death ligand-1 (PD-L1) and programmed death ligand-2 (PD-L2). CD80, along with CD86, functions as a ligand for two structurally similar molecules expressed in T cells, i.e., CD28 and CTLA-4. CD28 activates T cells, while CTLA-4 suppresses them. Targeting inhibition of PD-1, PD-L1, and CTLA-4 is known to be effective in treating tumors in human patients because it can activate tumor-specific T cells. In addition, it has been reported that an anti-CD80 antibody that inhibits the binding of CD80 to CD28 suppresses T cell activation (Patent Literature 1).

Interestingly, it has been reported that an anti-PD-L1 antibody that inhibits CD80/PD-L1 interaction activates tumor immunity and is useful for cancer treatment (Non-Patent Literature 1 and Patent Literature 2). On the other hand, it has been reported that CD80 and PD-L1 are expressed and bound on the same cells. It has also been reported that the maintenance of T cell activity by CD80 involves inhibition of immunosuppression by the PD-1/PD-L1 system, in addition to the action mediated by CD28 (Non Patent Literatures 2 and 3). Thus, the physiological function of the CD80/PD-L1 interaction has not been elucidated.

CITATIONS LIST

Patent Literature

Patent Literature 1: WO1998/019706
Patent Literature 2: US2011/0280877 A

Non Patent Literature

Non Patent Literature 1: The Journal of Immunology, 2011, 187: 1113-1119
Non Patent Literature 2: Cancer Immunol Res. 2014 July; 2 (7): 610-615
Non Patent Literature 3: Cancer Immunology Research, 2018 Jun. 5, 6 (8), 921-929

SUMMARY OF INVENTION

Technical Problems

It is one object of the present application to provide an immunosuppressive agent.

Solutions to Problems

In one aspect, the present disclosure provides an immunosuppressive agent containing a substance that promotes the binding of PD-L1 to PD-1 and is selected from an anti-CD80 antibody and an anti-PD-L1 antibody.

In one aspect, the present disclosure provides an anti-CD80 antibody including: a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14.

In one aspect, the present disclosure provides an anti-CD80 antibody including: a heavy chain variable region including a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and a light chain variable region including a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22.

In one aspect, the present disclosure provides an anti-CD80 antibody that competes with any of the above antibodies for binding to CD80.

In one aspect, the present disclosure provides an immunosuppressive agent containing any of the above antibodies as an active ingredient.

In one aspect, the present disclosure provides a prophylactic and/or therapeutic agent for an autoimmune disease, an allergic disease, or a graft-versus-host disease, containing any of the above antibodies as an active ingredient.

Advantageous Effects of Invention

The present disclosure provides: immunosuppressive agents; prophylactic and/or therapeutic agents for autoimmune diseases, allergic diseases, or graft-versus-host diseases; or antibodies that can be utilized for these.

BRIEF DESCRIPTION OF DRAWINGS

FIG. 1 shows intensities of the binding of PD-1-EC (left) and the labeled antibodies (right) shown in the drawing to PD-L1 (upper row) or PD-L2 (lower row) and IIAdL1 cells expressing CD80 or CD86.

FIG. 2 shows the intensifies of the binding of PD-1-EC and anti-PD-L1 antibody to IIAdL1-PD-L1 cells with and without co-culture with IIAdL1-mock cells or IIAdL1-CD80 cells.

FIG. 15 shows the PD-1-EC binding abilities of IIAdL1-CD80 cells expressing the isolated PD-L1 mutant (upper) and PD-L1 with amino acid substitution of Y56 (lower). The PD-1-EC binding intensities of cells are shown in comparison with the PD-1-EC binding intensities of IIAdL1-PD-L1 cells that do not have CD80.

FIG. 24 shows the results of further analysis of the data shown in the middle and lower rows in FIG. 22. The rates of PD-1-dependent inhibition mediated by the molecules shown in the drawing are shown (0.3 μM antigen peptide). One-way ANOVA with Dunnett's post-test. ***p<0.001.

FIG. 25 shows intensities of the binding of human PD-1-EC and the antibodies shown in the drawing to IIAdL1 cells expressing human PD-L1 (upper), human PD-L2 (lower) and human CD80 or human CD86.

FIG. 26 shows intensities of the binding of human PD-1-EC and IIAdL1 cells expressing human PD-L1 with and without co-culture with IIAdL1 cells expressing human CD80.

FIG. 29 shows intensities of the binding of PD-1-EC to IIAdL1 cells expressing human PD-L1N63D/G119S mutants (upper) and IIAdL1 cells expressing human CD80, CD80192E, and CD80L104E (lower).

FIG. 47 shows that the administration of the anti-mouse CD80 antibody TKMG48 substantially reduced the symptoms of EAE in wild-type mice.

FIG. 48 shows that the administration of the anti-mouse CD80 antibody TKMG48 substantially reduced the symptoms of EAE in wild-type mice, but did not in PD-L1 knockout mice (PD-L1 K.O. in the drawing).

FIG. 51 shows that the anti-human CD80 antibody TKMF5 had low binding to CD80 mutants lacking the ability to bind PD-L1. 2D10 is a commercially available anti-human CD80 antibody.

FIG. 52 shows the amino acid sequences of the heavy and light chain variable regions of the anti-human CD80 antibody TKMF5. Each CDR is shown in a square.

FIG. 53 shows the amino acid sequences of the heavy and light chain variable regions of the anti-mouse CD80 antibody TKMG48. Each CDR is shown in a square.

DESCRIPTION OF EMBODIMENTS

Figure 3:
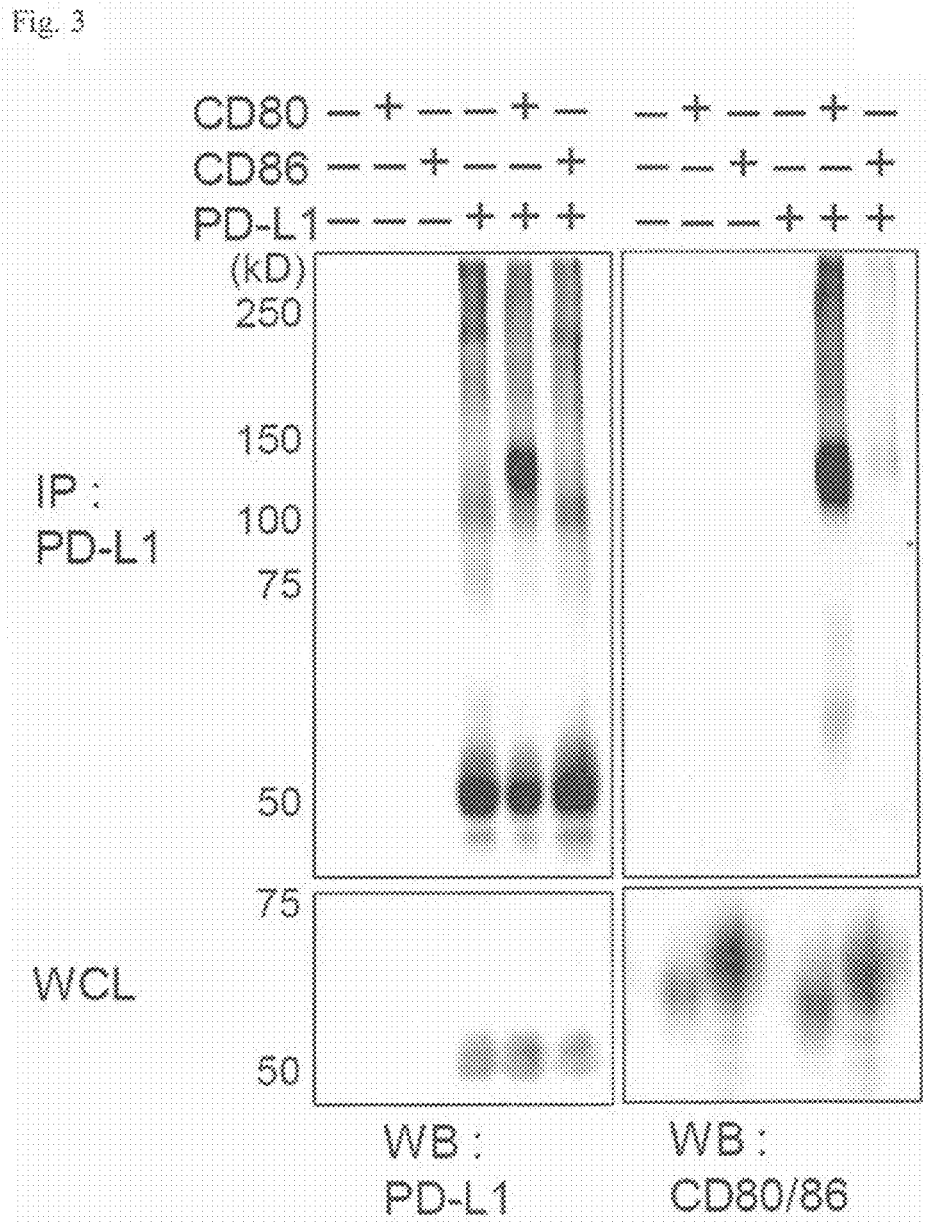
FIG. 3 shows co-immunoprecipitation of CD80 and PD-L1 in IIAdL1 cells. WCL: whole uncrosslinked cell lysate.

In the present disclosure, when a numerical value is accompanied by the term "about", it is intended to encompass a range of 10% of that value. For example, "about 20" shall encompass "18-22". A range expressed by numerical values encompasses all values between these numerical values, and the numerical values at both of the ends. The "about" for a range applies to both ends of the range. Therefore, for example, "about 20 to 30" encompasses "18 to 33".

In the present disclosure, amino acid residues are represented by the following abbreviations.

Ala or A: alanine
Arg or R: arginine
Asn or N: asparagine
Asp or D: aspartic acid
Cys or C: cysteine
Gln or Q: glutamine
Glu or E: glutamic acid
Gly or G: glycine
His or H: histidine
Ile or I: isoleucine
Leu or L: leucine
Lys or K: lysine
Met or M: methionine
Phe or F: phenylalanine
Pro or P: proline
Ser or S: serine
Thr or T: threonine
Trp or W: tryptophan
Tyr or Y: tyrosine
Val or V: valine PD-L1 (also called CD274) is a ligand for PD-1 and is expressed in a variety of cells, including dendritic and tumor cells. PD-1 is a typical immune checkpoint receptor on the surface of T cells, and the binding of PD-L1 to PD-1 can suppress the immune response. Therefore, a substance that promotes the binding of PD-L1 to PD-1 can be used as an immunosuppressive agent. The inventors of the present application have found that certain anti-CD80 and anti-PD-L1 antibodies promote the binding of PD-L1 to PD-1.

The binding of PD-L1 to PD-1 can be measured by bringing, for example, a cell expressing PD-L1 into contact with a soluble peptide including an extracellular region of PD-1 having a detectable label (e.g., a fluorescent label, a luminescent label, a radioactive label, a magnetic label, etc.), and measuring the amount of the label binding to the cell. An unlabeled soluble peptide may be bound to the peptide and used in combination with a labeled substance (e.g., a secondary antibody). Specifically, the binding of PD-L1 to PD-1 can be measured by the method in the examples of the present application described below.

CD80 is expressed primarily on the surface of dendritic cells, activated B cells and macrophages, and can control T cell activation and survival, acting as a ligand for two different proteins (CD28 and CTLA-4) present on the surface of T cells. Although not limited by theory, the inventors of the present application have revealed that the binding (cis-binding) of CD80 to PD-L1 on the same cell inhibits the binding of the PD-L1 to PD-1 on T cells. Therefore, when the cis-binding of CD80 to PD-L1 is inhibited, the binding of PD-L1 to PD-1 can be promoted. In one aspect, the substance that promotes the binding of PD-L1 to PD-1 is a substance that promotes the binding of PD-L1 present on the same cell as CD80, to PD-1. In one aspect, the substance that promotes the binding of PD-L1 to PD-1 is a substance that inhibits the cis-binding of CD80 to PD-L1. In one aspect, the substance that promotes the binding of PD-L1 to PD-1 is an anti-CD80 antibody. In one aspect, the substance that promotes the binding of PD-L1 to PD-1 is an anti-PD-L1 antibody.

In the present disclosure, "cis" means that two or more different molecules such as proteins are present on the same cell. For example, cis-PD-L1/CD80 means that PD-L1 and CD80 are present on the same cell.

In the present disclosure, "trans" means that two or more different molecules such as proteins are present on different cells. For example, trans-PD-L1/CD80 means that PD-L1 and CD80 are present on separate cells.

In the present disclosure, "cis-binding" means that two or more different membrane proteins expressed on the surface of one cell bind, associate or interact on the cell membrane. The cis-binding of CD80 to PD-L1 may occur in any cell, e.g., in cells of the immune system, in particular antigen-presenting cells, e.g., dendritic cells, macrophages, 13 cells, etc., which are antigen-presenting cells.

The cis-binding of CD80 to PD-L1 can be confirmed by treating cells expressing CD80 and PD-L1 with a cross-linking agent that cross-links adjacent proteins (e.g., bis(sulfosuccinimidyl)suberate) and subsequently detecting or measuring the cross-linked CD80 and PD-L1. The detection or measurement of the crosslinked CD80 and PD-L1 can be performed by detecting or measuring a molecule captured by a substance (e.g., an antibody) binding to one of CD80 and PD-L1, with use of another substance (e.g., an antibody) binding to the other of CD80 and PD-L1, in an assay system of immunoprecipitation, enzyme linked immunosorbent assay (ELISA), mass analysis, or the like. Specifically, the cis-binding of CD80 to PD-L1 can be measured by the method in the examples of the present application described below. Examples of the substance that binds to CD80 include CD28, CTLA-4, anti-CD80 antibodies, and fragments thereof. Examples of the substance that binds to PD-L1 include PD-1, anti-PD-L1 antibodies, and fragments thereof. The substance for the detection or measurement may have a detectable label (e.g., a fluorescent label, a luminescent label, a radioactive label, a magnetic label, etc.).

In the present disclosure, "inhibiting cis-binding" encompasses dissociating cis-bound CD80 and PD-L1 and/or preventing CD80 and PD-L1 from becoming cis-bound. In one embodiment, a substance that promotes the binding of PD-L1 to PD-1 inhibits the cis-binding of CD80 to PD-L1 by competition.

In one embodiment, when cultured cells exhibiting high level expression of CD80 and PD-L1 (for example, cells obtained by causing DO11.10 T cells lacking the PD-1 and PD-L1 genes to express CD80 and PD-L1 under the LTR promoter (DOdKO cells)) are cultured under the presence of 10 μg/ml of the substance that promotes the binding of PD-L1 to PD-1, the substance promotes the binding of PD-L1 to PD-1 at least about twice or more, for example, about 5 times or more, or about 10 times or more. For example, an example in which the binding is measured when the substance that promotes the binding of PD-L1 to PD-1 is an anti-CD80 antibody is described in the description of the examples of the present application.

In the present disclosure, CD80, PD-L1 and PD-1 may be of any species, typically mammals (e.g., humans, mice, rats, hamsters, rabbits, cats, dogs, cows, sheep, monkeys, etc.). Of these, mice or humans are preferable, and humans are particularly preferable. The amino acid sequences of CD80, PD-L1 and PD-1 derived from various species are readily available using known databases. Representative amino acid sequences of human and mouse CD80 are registered as GenBank accession numbers NP_005182 (SEQ ID NO: 1) and NP_033985 (SEQ ID NO: 2), respectively. Representative amino acid sequences of human and mouse PD-L1 are registered as GenBank accession numbers NP_054862 (SEQ ID NO: 3) and NP 068693 (SEQ ID NO: 4), respectively. Representative amino acid sequences of human and mouse PD-1 are registered as GenBank accession numbers NP 005009 (SEQ ID NO: 5) and NP_032824 (SEQ ID NO: 6), respectively. In the present disclosure, CD80, PD-L1 and PD-1 encompass the products of their naturally occurring alleles.

In one embodiment, the cis-binding between CD80 and PD-L1 is a binding mediated by at least a region that includes an amino acid corresponding to isoleucine at position 92 and/or leucine at position 104 in human CD80 having the amino acid sequence of SEQ ID NO: 1 (preferably, a region that includes an amino acid corresponding to isoleucine at position 92 and leucine at position 104 in human CD80 having the amino acid sequence of SEQ ID NO: 1), and a region that includes an amino acid corresponding to asparagine at position 63 and/or glycine at position 119 in human PD-L1 having the amino acid sequence of SEQ ID NO: 3 (preferably, a region that includes an amino acid corresponding to asparagine at position 63 and glycine at position 119 in human PD-L1 having the amino acid sequence of SEQ ID NO: 3). Alternatively, the cis-binding between CD80 and PD-L1 is a binding mediated by at least a region that includes an amino acid corresponding to leucine at position 96 and/or leucine at position 107 in mouse CD80 having the amino acid sequence of SEQ ID NO: 2 (preferably, a region that includes an amino acid corresponding to leucine at position 96 and leucine at position 107 in mouse CD80 having the amino acid sequence of SEQ ID NO: 2) and a region that includes an amino acid corresponding to valine at position 54, tyrosine at position 56, and/or glutamic acid at position 58 in mouse PD-L1 having the amino acid sequence of SEQ ID NO: 4 (preferably, a region that includes an amino acid corresponding to valine at position 54, tyrosine at position 56, and glutamic acid at position 58 in mouse PD-L1 having the amino acid sequence of SEQ ID NO: 4). The region including the above-described amino acid may be composed of continuous amino acid residues or may be composed of discontinuous amino acid residues.

In one embodiment, the anti-CD80 antibody binds to a region including an amino acid corresponding to isoleucine at position 92 and/or leucine at position 104 of human CD80 having the amino acid sequence of SEQ ID NO: 1. In a preferred embodiment, the anti-CD80 antibody binds to a region including an amino acid corresponding to isoleucine at position 92 and leucine at position 104 of human CD80 having the amino acid sequence of SEQ ID NO: 1. The region including the above-described amino acid may be composed of continuous amino acid residues or may be composed of discontinuous amino acid residues.

In one embodiment, the anti-CD80 antibody binds to a region including an amino acid corresponding to leucine at position 96 and/or leucine at position 107 of mouse CD80 having the amino acid sequence of SEQ ID NO: 2. In a preferred embodiment, the anti-CD80 antibody binds to a region including an amino acids corresponding to leucine at position 96 and leucine at position 107 of mouse CD80 having the amino acid sequence of SEQ ID NO: 2. The region including the above-described amino acid may be composed of continuous amino acid residues or may be composed of discontinuous amino acid residues.

In one embodiment, the anti-PD-L1 antibody binds to a region including an amino acid corresponding to asparagine at position 63 and/or glycine at position 119 in human PD-L1 having the amino acid sequence of SEQ ID NO: 3. In a preferred embodiment, the anti-PD-L1 antibody binds to a region including an amino acid corresponding to asparagine at position 63 and glycine at position 119 of human PD-L1 having the amino acid sequence of SEQ ID NO: 3. The region including the above-described amino acid may be composed of continuous amino acid residues or may be composed of discontinuous amino acid residues.

In one embodiment, the anti-PD-L1 antibody binds to a region including an amino acid corresponding to valine at position 54, tyrosine at position 56, and/or glutamic acid at position 58 of mouse PD-L1 having the amino acid sequence of SEQ ID NO: 4. In a preferred embodiment, the anti-PD-L1 antibody binds to a region including an amino acid corresponding to valine at position 54, tyrosine at position 56, and glutamic acid at position 58 of mouse PD-L1 having the amino acid sequence of SEQ ID NO: 4. The region including the above-described amino acid may be composed of continuous amino acid residues or may be composed of discontinuous amino acid residues.

"An amino acid corresponding to isoleucine at position 92 of human CD80 having the amino acid sequence of SEQ ID NO: 1" means an amino acid in CD80 that matches with isoleucine at position 92 of SEQ ID NO: 1 when a certain amino acid sequence of CD80 and the amino acid sequence of SEQ ID NO: 1 are aligned in an optimum state (the state in which the amino acid matching is maximized). "An amino acid corresponding to leucine at position 104 in human CD80 having the amino acid sequence of SEQ ID NO: 1", "an amino acid corresponding to leucine at position 96 and/or leucine at position 107 in mouse CD80 having the amino acid sequence of SEQ ID NO: 2", "an amino acid corresponding to asparagine at position 63 and/or glycine at position 119 in human PD-L1 having the amino acid sequence of SEQ ID NO: 3", and "valine at position 54, tyrosine at position 56, and/or glutamic acid at position 58 of mouse PD-L1 having the amino acid sequence of SEQ ID NO: 4" are also defined in the same way. For example, leucine at position 96 in mouse CD80 having the amino acid sequence of SEQ ID NO: 2, and leucine at position 107 of mouse CD80 having the amino acid sequence of SEQ ID NO: 2 correspond to isoleucine at position 92 of human CD80 having the amino acid sequence of SEQ ID NO: 1, and leucine at position 104 in human CD80 having the amino acid sequence of SEQ ID NO: 1, respectively.

In the present disclosure, the term "antibody" is used to encompass various antibody structures such as monoclonal antibodies, polyclonal antibodies, chimeric antibodies, humanized antibodies, human antibodies, and multispecific antibodies (e.g., bispecific antibodies). The type of antibody is not particularly limited, and examples thereof include antibodies derived from mice, rats, rabbits, goats, and humans. As the antibody, a humanized antibody and a human antibody (fully human antibody) are preferable. Further, as the antibody, a monoclonal antibody is preferable, and an isolated monoclonal antibody is more preferable.

In the present disclosure, the term "isolated monoclonal antibody" means a monoclonal antibody that has been identified, separated, and/or purified from impurities including multiple or innumerable components extracted from host cells such as hybridomas or culture supernatants thereof, thereby having become substantially a single pure component.

In the present disclosure, the term "antibody" also encompasses molecules that include a portion of an antibody as a component and retain its binding property to an antigen. For example, the antibody of the present application encompasses antibody heavy and light chain variable regions ($V_H$ and $V_L$), $F(ab')_2$, Fab', Fab, Fv, disulphide-linked FV(sdFv), Single-Chain FV(scFV), Fab3, Diabody, Triabody, Tetrabody, Minibody, Bis-scFv, $(scFv)_2$-Fc, and intact-IgG, as well as polymers of these, though it is not limited to these.

The immunoglobulin class of an antibody is determined based on the heavy chain constant region. Examples of the immunoglobulin class include IgA, IgD, IgE, IgG, and IgM, and the heavy chains corresponding thereto are called α chain, δ chain, ε chain, γ chain, and μ chain, respectively. The immunoglobulin class can be further subclassed into subclasses (isotypes) such as IgG1, IgG2, IgG3, IgG4, IgA1 and IgA2. The immunoglobulin class and subclass of the antibody herein are not particularly limited. In one embodiment, the immunoglobulin class is IgG. The light chain of an antibody can be divided into a κ chain and a κ chain based on its constant region, but the antibody herein may have either a κ chain or a λ chain.

The variable region of an antibody is usually composed of three complementarity determining regions (also referred to as CDRs) interposed between four framework regions (also referred to as FRs). Incidentally, in this specification, the amino acid positions assigned to the CDR of the variable region of the antibody and the framework are defined according to Kabat (see Sequences of Proteins of Immunological Interest (National Institute of Health, Bethesda, Md., (1987) and (1991)).

An anti-CD80 antibody and an anti-PD-L1 antibody, respectively, can be obtained by a general method by using, as an immunogen, a peptide including all or part of CD80 or PD-L1, e.g., all or part of the extracellular region of CD80 or PD-L1. A peptide including all or part of CD80 or PD-L1 can be prepared by conventional peptide synthesis methods, for example, by genetic engineering techniques or chemical synthesis.

A polyclonal antibody can be prepared by a general method such as the method described in "Antibodies: A Laboratory Manual, Lane, H. D. et al. eds., Cold Spring Harbor Laboratory Press, New York, 1989" and the like. Specifically, anti-CD80 polyclonal antibodies and anti-PD-L1 polyclonal antibodies can be prepared by immunizing mammals such as rats, mice, rabbits, goats, or horses with peptides including all or part of CD80, and peptides including all or part of PD-L1, respectively.

A monoclonal antibody can be obtained by a known method such as a method for producing a hybridoma that produces an antibody, or a method for producing an expression vector containing an antibody gene using a genetic engineering technique and causing it to be expressed in cells.

Hybridomas that secrete monoclonal antibodies can be made according to the method described in Kohler et al., Nature 256: 495, 1975. First, the immunogen is mixed with a suitable substance for enhancing antigenicity (e.g., keyhole limpet hemocyanin, bovine serum albumin, etc.) and, if necessary, an immunostimulant (such as Freund's complete or incomplete adjuvant), and non-human mammals such as rats, mice, rabbits, goats, or horses are immunized with the same. Usually, immunized animals are subjected to multiple rounds of immunization at intervals of 3 to 10 days, and 1 to 100 μg of the immunogenic peptide is administered. Immunocompetent cells (cells capable of producing antibodies in immune animals) are then collected from the immunized animals that have undergone multiple rounds of immunization, and are fused with myeloma cells that are not capable of producing autoantibodies (e.g., cells derived from mammals such as mice, rats, guinea pigs, hamsters, rabbits, or humans). For the cell fusion, the polyethylene glycol method, the electric fusion method, or the like is used. Furthermore, cells that have been successfully fused are selected based on selection markers that the fused cells have, and the reactivity of the antibody produced by the selected cells to the immunogen is confirmed by ELISA, radioimmunoassay, the fluorescent antibody method, etc. Thereby, a hybridoma that produces the desired monoclonal antibody is obtained. The monoclonal antibody can be isolated from the culture supernatant in which the obtained hybridoma is cultured in vitro. It can also be cultured in vivo in ascites of mice, rats, guinea pigs, hamsters, rabbits, or the like and isolated from the ascites.

In addition, a monoclonal antibody can be obtained by cloning an antibody gene from the obtained hybridoma, incorporating it into an appropriate expression vector and causing it to be expressed in a host cell, as is described below (P. J. Delves., ANTIBODY PRODUCTION ESSENTIAL TECHNIQUES., 1997 WILEY; P. Shepherd and C. Dean., Monoclonal Antibodies., 2000 OXFORD UNIVERSITY PRESS; J. W. Goding., Monoclonal Antibodies: principles and practice., 1993 ACADEMIC PRESS). Furthermore, using a transgenic animal production technique, a transgenic animal (for example, a cow, a goat, a sheep, or a pig) in which the gene of the antibody of interest is incorporated into an endogenous gene is produced, and for example, a monoclonal antibody derived from the antibody gene can also be obtained from milk of the transgenic animal.

The obtained monoclonal antibody can be purified by an appropriate combination of methods well known in the art, for example, chromatography using a protein A column, ion exchange chromatography, hydrophobic chromatography, ammonium sulfate precipitation, gel filtration, affinity chromatography, and the like.

A chimeric antibody is an antibody including sequences derived from different species, for example, an antibody in which a variable region and a constant region that are derived from different species, respectively, are linked. In one embodiment, the chimeric antibody is composed of a variable region of an antibody derived from a non-human mammal and a constant region derived from a human antibody. A chimeric antibody can be obtained by, for example, linking a polynucleotide encoding a variable region of an antibody derived from a non-human mammal and a polynucleotide encoding a constant region of a human antibody, incorporating the same into an expression vector, and introducing this expression vector into a host so that the expression vector is expressed therein.

The CDR is a region that substantially determines the binding specificity of an antibody, and shows great diversity in amino acid sequence. On the other hand, the amino acid sequences constituting an FR show high homology, even between antibodies having different binding specificities. Therefore, the binding specificity of one antibody can be transplanted to another antibody by CDR transplantation.

A humanized antibody is generally composed of CDRs of an antibody derived from a non-human animal, FRs derived from a human antibody, and constant regions derived from the human antibody. A humanized antibody can be obtained by transplanting CDRs of an antibody derived from a non-human animal into a human antibody. A humanized antibody can be prepared by a variety of methods, one example of which is Overlap Extension PCR (Almagro and Fransson, Front. Biosci. 13: 1619-1633 (2008)). In this method, PCR is performed by using, as a primer, an oligonucleotide having a portion that overlaps an end of a CDR of an antibody derived from a non-human animal (for example, a mouse antibody) and a portion that overlaps an end of an FR of a human antibody, whereby a polynucleotide in which the CDR of the antibody derived from the non-human animal and the FR derived from the human antibody are linked is synthesized. Next, the obtained polynucleotide is linked with a polynucleotide encoding a constant region of the human antibody, and incorporated into an expression vector. Then, this expression vector is introduced into a host so as to be expressed. Thereby, a humanized antibody can be obtained.

A method for selecting an FR suitable for producing a humanized antibody is known. For example, an FR selected by the best fit method (Sims et al. J. Immunol. 151: 2296 (1993)), or an FR derived from a consensus sequence of a particular subgroup of a light chain or heavy chain variable region of a human antibody (Carter et al. Proc. Natl. Acad. Sci. USA 89: 4285 (1992); Presta et al. J. Immunol. 151: 2623(1993)) can be used.

Human antibodies can be obtained, for example, by sensitizing human lymphocytes in vitro with desired antigens and then fusing the sensitized lymphocytes with human myeloma cells (Japanese Patent Publication No. 1-59878). For human myeloma cells, which are fusion partners, for example, U266 can be used. Human antibodies can also be obtained by immunizing transgenic animals with the entire repertoire of human antibody genes with the desired antigen (Lonberg, Nat. Biotech. 23: 1117-1125, 2005). Furthermore, a technique for obtaining human antibodies by panning using a human antibody library is also known (Antibody Phage Display: Methods and Protocols, Methods in Molecular Biology 178, 2001). For example, the variable region of a human antibody is expressed as a single-chain antibody (scFv) on the surface of a phage by a phage display method, a phage that binds to an antigen is selected, and the gene of the selected phage is analyzed. This enables to determine a DNA sequence encoding the variable region of the human antibody binding to the antigen. Next, this variable region sequence is linked by in-frame with the sequence of the human antibody constant region, and incorporated into an appropriate expression vector. Then, this expression vector is introduced into a host so as to be expressed. Thereby, a human antibody can be obtained.

A multispecific antibody is an antibody that binds to at least two different sites. Examples of the multispecific antibody include a bispecific antibody and a trispecific antibody. In one embodiment, the multispecific antibody binds to CD80 or PD-L1, and one or more other antigens. A multispecific antibody can be made, for example, by a genetic engineering technique, or by binding two or more antibodies or antibody fragments that respectively recognize different antigens.

The antibody fragment can be obtained, for example, by digesting the antibody with a protease such as papain or pepsin. Alternatively, it can be obtained by introducing an expression vector including a polynucleotide encoding an antibody fragment into a host cell, and causing it to be expressed in the host cell (e.g., Co, M S et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol (1986) 121, 652-663; Rousseaux, J. et al., Methods Enzymol. (1986) 121, 663-669; Bird, R. E. and Walker, B. W., Trends Biotechnol. (1991) 9, 132-137; Hudson et al., Nat. Med., (2003) 9, 129-134).

As described above, an antibody can be obtained by introducing an expression vector including a polynucleotide encoding the antibody into a cell and causing it to be expressed therein. Specifically, an expression vector is constructed so that the sequence encoding the antibody is expressed in an expression control region such as an enhancer or a promoter, and the host cell is transformed with this expression vector so that the antibody is expressed.

That is, the present disclosure also provides a polynucleotide encoding an anti-CD80 antibody or an anti-PD-L1 antibody, an expression vector including the polynucleotide, and a transformed cell including the polynucleotide or the expression vector.

As the host cell, for example, eukaryotic cells such as animal cells, plant cells, and fungal cells can be used. Examples of the animal cells include mammalian cells (e.g., CHO, COS, NIH3T3, myeloma, BHK (baby hamster kidney), HeLa, Vero), amphibian cells (e.g., *Xenopus* oocytes), or insect cells (e.g., Sf9, Sf21, Tn5). Examples of fungal cells include yeast (e.g., the genus *Saccharomyces*, such as *Saccharomyces cerevisiae*), filamentous fungi (e.g., the genus *Aspergillus*, such as *Aspergillus niger*), and the like. In addition, prokaryotic cells such as colon *Bacillus* (*Escherichia coli* (*E. coli*)) (e.g., JM109, DH5a, HB101, etc.) and *Bacillus subtilis* can also be used as host cells. The vector can be introduced into the host cell by, for example, the calcium phosphate method, the DEAE dextran method, the electroporation method, or a lipofection.

The binding of the obtained anti-CD80 antibody or anti-PD-L1 antibody to CD80 or PD-L1 can be confirmed by ELISA, the fluorescent antibody method, the radioimmunoassay (RIA), the BIACORE® surface plasmon resonance assay, etc.

Binding of the obtained anti-CD80 antibody or anti-PD-L1 antibody to CD80 or PD-L1 can also be confirmed by a competitive assay. For example, it can be confirmed by examining, with FACS, ELISA, or the like, whether the obtained anti-CD80 antibody competes with a known anti-CD80 antibody for binding to CD80, or whether the obtained anti-PD-L1 antibody competes with a known anti-PD-L1 antibody for binding to PD-L1. As a known anti-CD80 antibody, for example, an anti-CD80 antibody can be used that has a heavy chain variable region described below, a light chain variable region described below, or a CDR sequence described below.

In one embodiment, the anti-CD80 antibody or anti-PD-L1 antibody binds to CD80 or PD-L1 with an equilibrium dissociation constant (KD) of $10^{-7}$M or less or $10^{-8}$M or less, such as $10^{-7}$M to $10^{-15}$M, $10^{-7}$M to $10^{-13}$M, $10^{-7}$M to $10^{-9}$M., $10^{-8}$M to $10^{-15}$M, $10^{-8}$M to $10^{-13}$M, $10^{-8}$M to $10^{-9}$M, $10^{-9}$M to $10^{-12}$M, or $10^{-9}$M to $10^{-11}$M. The equilibrium dissociation constant can be measured, for example, by the biolayer interferometry. Specifically, the equilibrium dissociation constant can be measured by the method in the examples of the present application described below.

Preferably, the anti-CD80 antibody does not substantially inhibit the binding of CD80 to CTLA-4. The binding of CD80 to CTLA-4 can be measured by bringing, for example, a cell expressing CD80 into contact with a soluble peptide including an extracellular region of CTLA-4 having a detectable label (e.g., a fluorescent label, a luminescent label, a radioactive label, a magnetic label, etc.), and measuring the amount of the label binding to the cell. An unlabeled soluble peptide may be bound to the peptide and used in combination with a labeled substance (e.g., a secondary antibody). The presence or absence of inhibition of the binding of CD80 to CTLA-4, or the degree of the inhibition, can be confirmed by comparing the amount of a label that binds to cells in the presence of the anti-CD80 antibody, and that in the absence of the same. In this context, "does not substantially inhibit the binding" means that in the presence of a sufficient amount (e.g., about 10 μg/ml) of an anti-CD80 antibody against CD80 expressed on the cell surface, the amount of binding of CD80 to CTLA-4 is about 70%, about 75%, about 80%, about 85%, about 90%, about 95%, about 96%, about 97%, about 98%, or about 99% or more (may exceed 100%) of the amount of binding of CD80 to CTLA-4 in the absence of the anti-CD80 antibody.

In addition, an anti-CD80 antibody that does not strongly inhibit the binding of CD80 to CD28 can be used. The binding of CD80 to CD28 can be measured by bringing, for example, cells expressing CD80 into contact with a soluble peptide including the extracellular region of CD28 having a detectable label (e.g., fluorescent label, luminescent label, radioactive label, magnetic label, etc.), and measuring the amount of label binding to the cells. An unlabeled soluble peptide may be bound to the peptide and used in combination with a labeled substance (e.g., a secondary antibody). The presence or absence of inhibition of the binding of CD80 to CD28, or the degree of the inhibition, can be confirmed by comparing the amount of a label that binds to cells in the presence of the anti-CD80 antibody, and that in the absence of the same. In this context, "does not strongly inhibit the binding" means that in the presence of a sufficient amount (e.g., about 10 μg/ml) of an anti-CD80 antibody against CD80 expressed on the cell surface, the amount of binding of CD80 to CD28 is about 40%, about 45%, about 50%, about 55%, about 60%, about 65%, about 70%, about 75%, about 80%, about 85%, about 90%, about 95%, about 96%, about 97%, about 98%, about 99%, or more (may exceed 100%) of the amount of binding in the absence of the anti-CD80 antibody.

In one embodiment, the anti-CD80 antibody includes:
  a heavy chain variable region including a CDR1, a CDR2, and a CDR3 in the amino acid sequence of SEQ ID NO: 7, or the amino acid sequence of SEQ ID NO: 7; and/or
  a light chain variable region including a CDR1, a CDR2, and a CDR3 in the amino acid sequence of SEQ ID NO: 8, or the amino acid sequence of SEQ ID NO: 8.

In one embodiment, the anti-CD80 antibody includes:
  a heavy chain variable region including CDR1, CDR2, and CDR3 in the amino acid sequence of SEQ ID NO: 15, or the amino acid sequence of SEQ ID NO: 15; and/or a light chain variable region including CDR1, CDR2, and CDR3 in the amino acid sequence of SEQ ID NO: 16, or the amino acid sequence of SEQ ID NO: 16.

In one embodiment, the anti-CD80 antibody includes:
a heavy chain variable region that includes:
a CDR1 including a sequence having a sequence identity of 80% or more, preferably 85% or more, more preferably 90% or more, and even more preferably 95% or more with the sequence of SEQ ID NO: 9;
a CDR2 including a sequence having a sequence identity of 80% or more, preferably 85% or more, more preferably 90% or more, and even more preferably 95% or more with the sequence of SEQ ID NO: 10; and
a CDR3 including a sequence having a sequence identity of 80% or more, preferably 85% or more, more preferably 90% or more, and even more preferably 95% or more with the sequence of SEQ ID NO: 11;
and/or
a light chain variable region that includes:
a CDR1 including a sequence having a sequence identity of 80% or more, preferably 85% or more, more preferably 90% or more, and even more preferably 95% or more with the sequence of SEQ ID NO: 12;
a CDR2 including a sequence having a sequence identity of 80% or more, preferably 85% or more, more preferably 90% or more, and even more preferably 95% or more with the sequence of SEQ ID NO: 13; and
a CDR3 including a sequence having a sequence identity of 80% or more, preferably 85% or more, more preferably 90% or more, and even more preferably 95% or more with the sequence of SEQ ID NO: 14.

In one embodiment, the anti-CD80 antibody includes:
a heavy chain variable region that includes:
a CDR1 including a sequence having a sequence identity of 80% or more, preferably 85% or more, more preferably 90% or more, and even more preferably 95% or more with the sequence of SEQ ID NO: 17;
a CDR2 including a sequence having a sequence identity of 80% or more, preferably 85% or more, more preferably 90% or more, and even more preferably 95% or more with the sequence of SEQ ID NO: 18; and
a CDR3 including a sequence having a sequence identity of 80% or more, preferably 85% or more, more preferably 90% or more, and even more preferably 95% or more with the sequence of SEQ ID NO: 19;
and/or
a light chain variable region that includes:
a CDR1 including a sequence having a sequence identity of 80% or more, preferably 85% or more, more preferably 90% or more, and even more preferably 95% or more with the sequence of SEQ ID NO: 20;
a CDR2 including a sequence having a sequence identity of 80% or more, preferably 85% or more, more preferably 90% or more, and even more preferably 95% or more with the sequence of SEQ ID NO: 21; and
a CDR3 including a sequence having a sequence identity of 80% or more, preferably 85% or more, more preferably 90% or more, and even more preferably 95% or more with the sequence of SEQ ID NO: 22.

In one embodiment, the anti-CD80 antibody includes:
a heavy chain variable region that includes:
a CDR1 including the sequence of SEQ ID NO: 9 in which 0, 1, or 2 amino acids are deleted, substituted, or added;
a CDR2 including the sequence of SEQ ID NO: 10 in which 0, 1, or 2 amino acids are deleted, substituted, or added;
a CDR3 including the sequence of SEQ ID NO: 11 in which 0, 1, or 2 amino acids are deleted, substituted, or added;
and/or
a light chain variable region that includes:
a CDR1 including the sequence of SEQ ID NO: 12 in which 0, 1, or 2 amino acids are deleted, substituted, or added;
a CDR2 including the sequence of SEQ ID NO: 13 in which 0, 1, or 2 amino acids are deleted, substituted, or added;
a CDR3 including the sequence of SEQ ID NO: 14 in which 0, 1, or 2 amino acids are deleted, substituted, or added.

In one embodiment, the anti-CD80 antibody includes:
a heavy chain variable region that includes:
a CDR1 including the sequence of SEQ ID NO: 17 in which 0, 1, or 2 amino acids are deleted, substituted, or added;
a CDR2 including the sequence of SEQ ID NO: 18 in which 0, 1, or 2 amino acids are deleted, substituted, or added;
a CDR3 including the sequence of SEQ ID NO: 19 in which 0, 1, or 2 amino acids are deleted, substituted, or added;
and/or
a light chain variable region that includes:
a CDR1 including the sequence of SEQ ID NO: 20 in which 0, 1, or 2 amino acids are deleted, substituted, or added;
a CDR2 including the sequence of SEQ ID NO: 21 in which 0, 1, or 2 amino acids are deleted, substituted, or added;
a CDR3 including the sequence of SEQ ID NO: 22 in which 0, 1, or 2 amino acids are deleted, substituted, or added.

In one embodiment, the anti-CD80 antibody includes: a heavy chain variable region that includes: a CDR1 including the amino acid sequence of SEQ ID NO: 9, a CDR2 including an amino acid sequence of SEQ ID NO: 10, and CDR3 including the amino acid sequence of SEQ ID NO: 11; and/or a light chain variable region that includes a CDR1 including the amino acid sequence of SEQ ID NO: 12, a CDR2 including the amino acid sequence of SEQ ID NO: 13, and a CDR3 including the amino acid sequence of SEQ ID NO: 14. In one embodiment, the anti-CD80 antibody includes: a heavy chain variable region that includes: a CDR1 consisting of the amino acid sequence of SEQ ID NO: 9, a CDR2 consisting of an amino acid sequence of SEQ ID NO: 10, and CDR3 consisting of the amino acid sequence of SEQ ID NO: 11; and/or a light chain variable region that includes a CDR1 consisting of the amino acid sequence of SEQ ID NO: 12, a CDR2 consisting of the amino acid sequence of SEQ ID NO: 13, and a CDR3 consisting of the amino acid sequence of SEQ ID NO: 14.

In one embodiment, the anti-CD80 antibody includes: a heavy chain variable region that includes: a CDR1 including the amino acid sequence of SEQ ID NO: 17, a CDR2 including an amino acid sequence of SEQ ID NO: 18, and CDR3 including the amino acid sequence of SEQ ID NO: 19; and/or a light chain variable region that includes a CDR1 including the amino acid sequence of SEQ ID NO: 20, a CDR2 including the amino acid sequence of SEQ ID NO: 21, and a CDR3 including the amino acid sequence of SEQ ID NO: 22. In one embodiment, the anti-CD80 antibody includes: a heavy chain variable region that includes: a CDR1 consisting of the amino acid sequence of SEQ ID NO:

17, a CDR2 consisting of an amino acid sequence of SEQ ID NO: 18, and CDR3 consisting of the amino acid sequence of SEQ ID NO: 19; and/or a light chain variable region that includes a CDR1 consisting of the amino acid sequence of SEQ ID NO: 20, a CDR2 consisting of the amino acid sequence of SEQ ID NO: 21, and a CDR3 consisting of the amino acid sequence of SEQ ID NO: 22.

In one embodiment, the anti-CD80 antibody includes: a heavy chain variable region that includes a sequence having a sequence identity of 80% or more, preferably 85% or more, more preferably 90% or more, and even more preferably 95% or more with the amino acid sequence of SEQ ID NO: 7; and/or a light chain variable region that includes a sequence having a sequence identity of 80% or more, preferably 85% or more, more preferably 90% or more, and even more preferably 95% or more with the amino acid sequence of SEQ ID NO: 8. In a further embodiment, the anti-CD80 antibody includes: a heavy chain variable region that includes the amino acid sequence of SEQ ID NO: 7 in which 0 to 5 amino acids are deleted, substituted, or added; and/or a light chain variable region that includes the amino acid sequence of SEQ ID NO: 8 in which 0 to 5 amino acids are deleted, substituted, or added. These embodiments also encompass the following: an anti-CD80 antibody in which no modification has occurred to the CDRs of the heavy chain variable region and/or the light chain variable region. Specifically, these embodiments encompass an anti-CD80 antibody that includes: a heavy chain variable region that includes a CDR1 including the amino acid sequence of SEQ ID NO: 9, a CDR2 including the amino acid sequence of SEQ ID NO: 10, and a CDR3 including the amino acid sequence of SEQ ID NO: 11; and/or a light chain variable region that includes a CDR1 including the amino acid sequence of SEQ ID NO: 12, a CDR2 including the amino acid sequence of SEQ ID NO: 13, and a CDR3 including the amino acid sequence of SEQ ID NO: 14.

In one embodiment, the anti-CD80 antibody includes: a heavy chain variable region that includes a sequence having a sequence identity of 80% or more, preferably 85% or more, more preferably 90% or more, and even more preferably 95% or more with the amino acid sequence of SEQ ID NO: 15; and/or a light chain variable region that includes a sequence having a sequence identity of 80% or more, preferably 85% or more, more preferably 90% or more, and even more preferably 95% or more with the amino acid sequence of SEQ ID NO: 16. In a further embodiment, the anti-CD80 antibody includes: a heavy chain variable region that includes the amino acid sequence of SEQ ID NO: 15 in which 0 to 5 amino acids are deleted, substituted, or added; and/or a light chain variable region that includes the amino acid sequence of SEQ ID NO: 16 in which 0 to 5 amino acids are deleted, substituted, or added. These embodiments also encompass the following: an anti-CD80 antibody in which no modification has occurred to the CDRs of the heavy chain variable region and/or the light chain variable region. Specifically, these embodiments encompass an anti-CD80 antibody that includes: a heavy chain variable region that includes a CDR1 including the amino acid sequence of SEQ ID NO: 17, a CDR2 including the amino acid sequence of SEQ ID NO: 18, and a CDR3 including the amino acid sequence of SEQ ID NO: 19; and/or a light chain variable region that includes a CDR1 including the amino acid sequence of SEQ ID NO: 20, a CDR2 including the amino acid sequence of SEQ ID NO: 21, and a CDR3 including the amino acid sequence of SEQ ID NO: 22.

In one embodiment, the anti-CD80 antibody includes a heavy chain variable region including the amino acid sequence of SEQ ID NO: 7 and/or a light chain variable region including the amino acid sequence of SEQ ID NO: 8. In a further embodiment, the anti-CD80 antibody includes a heavy chain variable region consisting of the amino acid sequence of SEQ ID NO: 7 and/or a light chain variable region consisting of the amino acid sequence of SEQ ID NO: 8.

In one embodiment, the anti-CD80 antibody includes a heavy chain variable region including the amino acid sequence of SEQ ID NO: 15 and/or a light chain variable region including the amino acid sequence of SEQ 1D NO: 16. In a further embodiment, the anti-CD80 antibody includes a heavy chain variable region consisting of the amino acid sequence of SEQ ID NO: 15 and/or a light chain variable region consisting of the amino acid sequence of SEQ ID NO: 16.

In one embodiment, the anti-CD80 antibody includes a heavy chain variable region including the CDRs 1 to 3 of the above-described light chain variable region and/or a light chain variable region including the CDRs 1 to 3 of the above-described heavy chain variable region.

In one embodiment, the anti-CD80 antibody is an antibody that competes, for binding to CD80, with any of the anti-CD80 antibodies identified in the above-described sequences. Competition can be confirmed, for example, by the competition assay described above.

"Sequence identity" is determined by comparing two optimally aligned sequences over the entire region of the sequences to be compared. Here, in the two optimally aligned sequences to be compared, the sequences may have additions or deletions (e.g., gaps). The sequence identity can be calculated using a program such as FASTA, BLAST, or CLUSTAL W provided in public databases (e.g., DDBJ (www.ddbj.nig.ac.jp)). Alternatively, the sequence identity can be determined using commercially available sequence analysis software (for example, Vector NTI® software, GENETYX® ver. 12).

Various methods are known as methods for modifying an amino acid sequence to obtain an antibody having desired properties. For example, a mutant with improved binding affinity can be obtained by a method based on phage display. In this method, for example, the alanine scanning mutagenesis method is used to identify amino acid residues that affect antibody-antigen interactions. Or alternatively, the crystal structure of an antigen-antibody complex is analyzed to identify the contact point between the antibody and the antigen, whereby the mutagenesis site is determined. A mutant in which the amino acid of this site is modified is prepared by error-prone PCR, site-specific mutagenesis, or the like, and the library of the obtained mutant is screened, whereby a mutant having a desired characteristic can be obtained.

The sugar chain of the Fc region of the anti-CD80 antibody or the anti-PD-L1 antibody may be modified. Examples of the antibody with a modified sugar chain include an antibody lacking fucose added to the sugar chain (US 2003/0157108 A), and an antibody having a sugar chain having bisect N-acetylglucosamine (GlcNAc) (WO2003/011878).

The anti-CD80 antibody or the anti-PD-L1 antibody may be bound to a polymer in order to, for example, extend the half-life of the antibody or improve stability, the polymer being polyethylene glycol (PEG), polypropylene glycol, polyoxyalkylene, a copolymer of polyethylene glycol and polypropylene glycol, or the like.

A substance that promotes the binding of PD-L1 to PD-1 can suppress immunity when administered in an effective amount to a subject. Therefore, an immunosuppressive agent is provided that contains, as an active ingredient, a substance that promotes the binding of PD-L1 to PD-1 and is selected from an anti-CD80 antibody and an anti-PD-L1 antibody.

Since the antibodies or immunosuppressive agents disclosed herein have low toxicity, they can be safely used as pharmaceutical products.

[Application to Pharmaceutical Products]

The antibodies or immunosuppressive agents disclosed herein can be used for the prevention and/or treatment of diseases characterized by enhanced immunity. Therefore, in one aspect, a prophylactic and/or therapeutic agent for a disease characterized by enhanced immunity, wherein the agent contains, as an active ingredient, a substance that promotes the binding of PD-L1 to PD-1 and is selected from an anti-CD80 antibody and an anti-PD-L1 antibody.

Examples of the disease characterized by enhanced immunity include autoimmune diseases, allergic diseases and graft-versus-host diseases. Examples of the autoimmune disease include Behcet's disease, systemic lumpus erythematosus, multiple sclerosis (systemic sclerosis, progressive systemic sclerosis), scleroderma, polymyositis, dermatomyositis, periarteritis nodosa (polyarteritis nodosa, microscopic polyangiitis), aortitis syndrome (Takayasu's arteritis), malignant rheumatoid arthritis, rheumatoid arthritis, juvenile idiopathic arteritis, Wegener's granulomatosis, mixed connective tissue disease, Sjogren's syndrome, Adult-onset Still's disease, allergic granulomatous angiitis, hypersensitivity vasculitis, Cogan's syndrome, RS3PE, temporal arteritis, polymyalgia rheumatica, fibromyalgia, antiphospholipid antibody syndrome, eosinophilic fasciitis, IgG4-related diseases (e.g., primary sclerosing cholangitis, autoimmune pancreatitis), Guillain-Barre syndrome, myasthenia gravis, chronic atrophic gastritis, autoimmune hepatitis, primary biliary cirrhosis, aortitis syndrome, Goodpasture syndrome, rapidly progressive glomerulonephritis, megaloblastic anemia, autoimmune hemolytic anemia, autoimmune neutropenia, idiopathic thrombocytopenic purpura, Basedow's disease (hyperthyroidism), Hashimoto disease, autoimmune adrenal insufficiency, primary hypothyroidism, idiopathic Addison disease (chronic hypoadreno corticism), type I diabetes, slowly progressive type I diabetes (latent autoimmune diabetes in adults), chronic discoid lupus erythematosus, circumscribed scleroderma, psoriasis, psoriatic arthritis, pemphigus, pemphigoid, gestational herpes, linear IgA bullous dermatosis, acquired epidermolysis bullosa, allopecia areata, white spots, vitiligo vulgaris, atopic dermatitis, neuromyelitis optica, Chronic inflammatory demyelinating polyneuropathy, sarcoidosis, bullous pemphigoid, giant cell arteritis, amyotrophic lateral sclerosis, eosinophilic granulomatosis with polyangiitis, Harada disease, autoimmune optic neuropathy, idiopathic azoospermia, habitual abortion, inflammatory bowel disease (e.g., ulcerative colitis, Crohn's disease), and celiac disease. In an embodiment, the autoimmune disease is type I diabetes, multiple sclerosis, systemic lupus erythematosus, or rheumatoid arthritis. In one embodiment, the autoimmune disease is multiple sclerosis. Examples of allergic disease include asthma, atopic dermatitis, rhinitis, conjunctivitis, and hay fever.

As used herein, "treating" or "treatment" means reducing or eliminating the cause of a disease in a subject with the disease, delaying or stopping the progression of the disease, reducing, alleviating, improving, and/or eliminating its symptoms, or suppressing the exacerbation of its symptoms.

As used herein, "preventing" or "prevention" means preventing the development of a disease, or reducing the likelihood of developing the disease in a subject, especially in a subject who is highly likely to develop the disease but has not yet developed the disease. It also encompasses the prevention of recurrence. Subjects who are likely to develop autoimmune diseases or allergic diseases but have not yet developed the diseases encompass subjects with enhanced immunity; subjects with genetic predispositions to autoimmune diseases or allergic diseases; and subjects who have been affected and cured of autoimmune or allergic diseases in the past. Subjects who may develop graft-versus-host diseases but have not yet developed encompass those who undergo an organ transplant.

Immunosuppressive agents, or prophylactic and/or therapeutic agents for diseases characterized by enhanced immunity, can be administered to animals, typically mammals (e.g., humans, mice, rats, hamsters, rabbits, cats, dogs, cows, sheep, and monkeys, etc.), among which humans are particularly preferred. Also preferred are subjects that require immunosuppression, or the prevention and/or treatment, and are particularly those who require the treatment.

The dose of the active ingredient is appropriately selected depending on the administration method, the age, body weight, health condition and the like of the administration target. For example, 10 µg/kg to 100 mg/kg, 100 µg/kg to 10 mg/kg, or 1 mg/kg to 10 mg/kg per day can be administered to an adult, continuously over a period ranging from 30 minutes to 24 hours a day, once to several times a day, or once to several times one or several days, or one or several weeks for example, once every 1 to 3 weeks, though not limited to this. The administration method also is appropriately selected depending on the age, body weight, health condition and the like of the administration target. The administration method may be oral administration or parenteral administration, but parenteral administration is preferable. Examples of parenteral administration include subcutaneous administration, intradermal administration, intraperitoneal administration, intramuscular administration, and intravenous administration, but intravenous administration is preferable.

Immunosuppressive agents, or prophylactic and/or therapeutic agents for diseases characterized by enhanced immunity, can be formulated by conventional methods. The formulation may contain a variety of pharmaceutically acceptable substances for formulation, as required in formulation. The substance for formulation can be appropriately selected depending on the dosage form of the formulation, and examples of the same include a buffering agent, a surfactant, a stabilizer, a preservative, an excipient, a diluent, an additive, a disintegrant, a binder, a coating agent, a lubricant, a lubricating agent, and a solubilizer. For example, immunosuppressive agents can be formulated as injections or infusions. The injection or the infusion can be in the sterilized aqueous solution form, the suspension form, or the emulsion form, or in the solid dosage form or lyophilized form for use in a state of being dissolved, suspended, or emulsified in a sterilized liquid. The sterilized liquid can be, for example, water for injection, saline, glucose solution, or isotonic solution. Immunosuppressive agents can also be formulated in such a manner that sustained release or controlled release of the active ingredient is achieved. Methods for producing these formulations are well known in the art.

The formulation may contain a pharmaceutically acceptable carrier. In the present disclosure, a "pharmaceutically acceptable carrier" contains a certain arbitrary substance that is non-reactive with the immune system of interest, which, when combined with an active ingredient, can retain the biological activity of that ingredient. Examples of the pharmaceutically acceptable carrier include stabilizers, solubilizers, suspending agents, emulsifiers, soothing agents, buffers, preservatives, pH regulators and antioxidants. As the stabilizer, for example, the following can be used: various amino acids, albumin, globulin, gelatin, mannitol, glucose, dextran, ethylene glycol, propylene glycol, polyethylene glycol, ascorbic acid, sodium bisulfite, sodium thiosulfate, sodium edetate, sodium citrate, and dibutylhydroxytoluene. As the solubilizer, for example, the following can be used: alcohols (e.g., ethanol), polyalcohols (e.g., propylene glycol, polyethylene glycol), and nonionic surfactants (e.g., polysorbate 20®, polysorbate 80®, HCO-50, etc.). As the suspending agent, for example, the following can be used: glycerin monostearate, aluminum monostearate, methyl cellulose, carboxymethyl cellulose, hydroxymethyl cellulose, and sodium lauryl sulfate. As the emulsifier, for example, the following can be used: gum arabic, sodium alginate, and tragacanth. As the soothing agent, for example, the following can be used: benzyl alcohol, chlorobutanol, and sorbitol can be used. As the buffer, for example, the following can be used: a phosphate buffer solution, an acetate buffer solution, a borate buffer solution, a carbonate buffer solution, a citrate buffer solution, a Tris buffer solution, a glutamic acid buffer solution, and an epsilon aminocaproic acid buffer solution. As the preservative, for example, the following can be used: methyl paraoxybenzoate, ethyl paraoxybenzoate, propyl paraoxybenzoate, butyl paraoxybenzoate, chlorobutanol, benzyl alcohol, benzalkonium chloride, sodium dehydroacetate, sodium edetate, boric acid, and borax. As the preservative, for example, benzalkonium chloride, paraoxybenzoic acid, and chlorobutanol can be used. As the pH adjuster, for example, hydrochloric acid, sodium hydroxide, phosphoric acid, and acetic acid can be used. As antioxidants, for example, the following can be used: (1) water-soluble antioxidants such as ascorbic acid, cysteine hydrochloride, sodium bisulfate, sodium metabisulfite, sodium sulfite, etc.; (2) oil-soluble antioxidants such as ascorbyl palmitate, butylated hydroxyanisole, butylated hydroxytoluene, lecithin, propyl gallate, α-tocopherol, etc.; and (3) metal chelating agents such as citric acid, ethylenediaminetetraacetic acid, sorbitol, tartaric acid, phosphoric acid.

An infusion solution for injection or infusion can be produced through a process of: sterilizing the same in the final step, or applying an aseptic technique such as filtering with a filter or the like and sterilizing the same; and then, filling the same in a sterile container. A vacuum-dried and lyophilized sterile powder (which may contain a pharmaceutically acceptable carrier powder) may be dissolved in a suitable solvent before use, so as to be used as the infusion solution for injection or infusion.

Immunosuppressive agents, or prophylactic and/or therapeutic agents for preventing and/or treating diseases characterized by enhanced immunity, can be used alone or in combination with one or more additional active ingredients, in particular with an active ingredient for immunosuppression. "Combination" of ingredients is not limited to the use of a dosage form containing all ingredients, and the use of a combination of dosage forms containing the ingredients respectively. It also encompasses administering all of the component simultaneously or administering the same with a delay as for a certain component, as long as they are used for immunosuppression, or the treatment and/or prevention of diseases characterized by enhanced immunity. In a case where a certain component is administered with a delay, there may be a period during which the components are co-administered. It is also possible to combine two or more additional active ingredients. The combined use enables, for example, to complement the prophylactic and/or therapeutic effects of other active ingredients, and to maintain and/or reduce the dose or the frequency of administration. Examples of the active ingredients suitable for the combined use include anti-inflammatory agents, antibacterial agents, antifungal agents, antiviral agents, immunosuppressive agents, and molecular targeting agents.

For example, when the immunosuppressive agent of the invention, or the prophylactic and/or therapeutic agent of the present invention for a disease characterized by enhanced immunity, is applied to the prevention and/or treatment of type I diabetes, it may be used in combination with any one or more agents selected from the following: insulin preparations (e.g., human insulin, insulin glargine, insulin lispro, insulin detemir, insulin aspart); sulfonylureas (e.g., glibenclamide, gliclazide, glimepiride); fast-acting insulin secretagogue (e.g., nateglinide); biguanide preparations (e.g. metformin), insulin sensitizers (e.g., pioglitazone); α-glucosidase inhibitors (e.g., acarbose, voglibose); therapeutic agents for diabetic neuropathy (e.g., epalrestat, mexiletine, imidapril); GLP-1 analogs (e.g., liraglutide, exenatide, lixisenatide); and DPP-4 inhibitors (e.g. sitagliptin, vildagliptin, alogliptin).

In addition, for example, when the immunosuppressive agent of the present invention, or the prophylactic and/or therapeutic agent of the present invention for a disease characterized by enhanced immunity, is applied to the prevention and/or treatment of multiple sclerosis, it may be used in combination with any one or more agents selected from the following: steroid drugs (e.g., cortisone acetate, hydrocortisone, hydrocortisone sodium phosphate, hydrocortisone sodium succinate, fludrocortisone acetate, prednisolone, prednisolone acetate, prednisolone sodium succinate, butyl prednisolone, prednisolone sodium phosphate, halopredone acetate, methylprednisolone, Methylprednisolone acetate, methylprednisolone sodium succinate, triamcinolone, triamcinolone acetate, triamcinolone acetonide, dexamethasone, dexamethasone acetate, dexamethasone phosphate, dexamethasone palmitate, paramethasone acetate, betamethasone); interferon β-1a, interferon β-1b, glatiramer acetate, mitoxantrone, azathiopurine, cyclophosphamide, cyclosporine, methotrexate, cladribine, adrenocorticotrophic hormone (ACTH), corticotropin, mizoribine, tacrolimus, fingolimod and alemtuzumab, etc.

In addition, for example, when the immunosuppressive agent of the present invention, or the prophylactic and/or therapeutic agent of the present invention for a disease characterized by enhanced immunity, is applied to the prevention and/or treatment of systemic lupus erythematosus, it may be used in combination with any one or more agents selected from the following: steroid drugs (e.g., the steroid drugs described above); other immunosuppressive agents (e.g., cyclosporine, tacrolimus, fingolimod, etc.); and belimumab.

In addition, for example, when the immunosuppressive agent of the invention, or the prophylactic and/or therapeutic agent of the present invention for a disease characterized by enhanced immunity, is applied to the prevention and/treatment of rheumatoid arthritis, it may be used in combination with one or more selected from the following: steroid drugs (for example, the steroid drugs described above); antirheumatic drugs (e.g., methotrexate, sulfasalazine, bucillamine, leflunomide, mizoribine, tacrolimus, etc.) or anticytokine drugs (e.g., infliximab, adalimumab, tocilizumab, etanercept, golimumab, certolizumab, etc.); and abatacept.

When applied to the prevention and/or treatment of other autoimmune diseases, allergic diseases or graft-versus-host diseases, the immunosuppressive agent of the present invention, or the prophylactic and/or therapeutic agent of the present invention for a disease characterized by enhanced immunity, may be used in combination with any one or more of the other agents described above.

In one aspect, a method for suppressing immunity is provided, the method including administering, to a subject in need of immunosuppression, an effective amount of a substance that promotes the binding of PD-L1 to PD-1 and is selected from an anti-CD80 antibody and an anti-PD-L1 antibody, or an immunosuppressive agent containing the substance.

As used herein, the term "effective amount" means an amount with which an effect of suppressing immunity in a subject can be exerted.

In one aspect, provided is a substance that promotes the binding of PD-L1 to PD-1 and is selected from an anti-CD80 antibody and an anti-PD-L1 antibody, or an immunosuppressive agent containing the substance, for use in immunosuppression.

In one aspect, provided is a substance that promotes the binding of PD-L1 to PD-1 and is selected from an anti-CD80 antibody and an anti-PD-L1 antibody, or an immunosuppressive agent containing the substance, for use in production of a pharmaceutical composition for immunosuppression.

In one aspect, provided is a method for preventing and/or treating a disease characterized by enhanced immunity, the method including administering, to a subject in need of preventing and/or treating the disease, an effective amount of a substance that promotes the binding of PD-L1 to PD-1 and is selected from an anti-CD80 antibody and an anti-PD-L1 antibody, or an immunosuppressive agent containing the substance.

In one aspect, provided is a substance that promotes the binding of PD-L1 to PD-1 and is selected from an anti-CD80 antibody and an anti-PD-L1 antibody, or an immunosuppressive agent containing the substance, for use in the prevention and/or treatment of a disease characterized by enhanced immunity.

In one aspect, provided is use of a substance that promotes the binding of PD-L1 to PD-1 and is selected from an anti-CD80 antibody and an anti-PD-L1 antibody, in the production of a prophylactic and/or therapeutic agent for preventing and/or treating a disease characterized by enhanced immunity. Also provided is an immunosuppressive agent containing the substance.

The present application provides, for example, the following embodiments.

[1-1] An immunosuppressive agent containing a substance that promotes binding of PD-L1 to PD-1, the substance being selected from an anti-CD80 antibody and an anti-PD-L1 antibody.

[1-2] The immunosuppressive agent according to [1-1] above, wherein the substance promotes the binding of PD-L1 present on the same cell as CD80, to PD-1.

[1-3] The immunosuppressive agent according to [1-1] or [1-2] above, wherein the substance promotes the binding of PD-L1 to PD-1 so that the binding increases about twice or more.

[1-4] The immunosuppressive agent according to any one of [1-1] to [1-3] above, wherein PD-1 is present on a T cell.

[1-5] The immunosuppressive agent according to any one of [1-1] to [1-4] above, wherein the substance is an anti-CD80 antibody.

[1-6] The immunosuppressive agent according to [1-5] above, wherein the anti-CD80 antibody binds to CD80 with an equilibrium dissociation constant of $10^{-7}$ M or less.

[1-7] The immunosuppressive agent according to [1-5] or [1-6] above, wherein the anti-CD80 antibody inhibits cis-binding of CD80 to PD-L1.

[1-8] The immunosuppressive agent according to [1-7] above, wherein the cis-binding is mediated by at least
 a region including an amino acid corresponding to isoleucine at position 92 and/or leucine at position 104 of human CD80 having the amino acid sequence of SEQ ID NO: 1, and
 a region including an amino acid corresponding to asparagine at position 63 and/or glycine at position 119 of human PD-L1 having the amino acid sequence of SEQ ID NO: 3, or
the cis-binding is mediated by at least
 a region including an amino acid corresponding to leucine at position 96 and/or leucine at position 107 of mouse CD80 having the amino acid sequence of SEQ ID NO: 2, and
 a region including an amino acid corresponding to valine at position 54, tyrosine at position 56, and/or glutamic acid at position 58 of mouse PD-L1 having the amino acid sequence of SEQ ID NO: 4.

[1-9] The immunosuppressive agent according to any one of [1-5] to [1-8] above, wherein the anti-CD80 antibody binds to
 a region that includes an amino acid corresponding to isoleucine at position 92 and/or leucine at position 104 of human CD80 having the amino acid sequence of SEQ ID NO: 1, or
 a region that includes an amino acid corresponding to leucine at position 96 and/or leucine at position 107 of mouse CD80 having the amino acid sequence of SEQ ID NO: 2.

[1-10] The immunosuppressive agent according to any one of [1-5] to [1-9] above, wherein the anti-CD80 antibody does not substantially inhibit binding of CD80 to CTLA-4.

[1-11] The immunosuppressive agent according to any one of [1-5] to [1-10] above, wherein the anti-CD80 antibody does not strongly inhibit binding of CD80 to CD28.

[1-12] An immunosuppressive agent containing an anti-CD80 antibody that promotes binding of PD-L1 present on the same cell as CD80, to PD-1, and does not strongly inhibit binding of CD80 to CD28.

[1-13] The immunosuppressive agent according to any one of [1-5] to [1-12] above, wherein the anti-CD80 antibody includes:
 (1) a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and
 a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14;

(2) a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and
a light chain variable region that includes a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22;
(3) a heavy chain variable region that includes a heavy chain CDR1 including the amino acid sequence of SEQ ID NO: 12, a heavy chain CDR2 including the amino acid sequence of SEQ ID NO: 13, and a heavy chain CDR3 including the amino acid sequence of SEQ ID NO: 14; and
a light chain variable region that includes a light chain CDR1 including the amino acid sequence of SEQ ID NO: 9, a light chain CDR2 including the amino acid sequence of SEQ ID NO: 10, and a light chain CDR3 including the amino acid sequence of SEQ ID NO: 11; or
(4) a heavy chain variable region that includes a heavy chain CDR1 including the amino acid sequence of SEQ ID NO: 20, a heavy chain CDR2 including the amino acid sequence of SEQ ID NO: 21, and a heavy chain CDR3 including the amino acid sequence of SEQ ID NO: 22; and
a light chain variable region that includes a light chain CDR1 including the amino acid sequence of SEQ ID NO: 17, a light chain CDR2 including the amino acid sequence of SEQ ID NO: 18, and a light chain CDR3 including the amino acid sequence of SEQ ID NO: 19.

[1-14] The immunosuppressive agent according to any one of [1-5] to [1-13] above, wherein the anti-CD80 antibody includes:
a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and
a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14.

[1-15] The immunosuppressive agent according to any one of [1-5] to [1-13] above, wherein the anti-CD80 antibody includes:
a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and
a light chain variable region that includes alight chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22.

[1-16] The immunosuppressive agent according to any one of [1-5] to [1-14] above, wherein the anti-CD80 antibody includes:
a heavy chain variable region that includes an amino acid sequence having an identity of 90% or more with the amino acid sequence of SEQ ID NO: 7; and
a light chain variable region that includes an amino acid sequence having an identity of 90% or more with the amino acid sequence of SEQ ID NO: 8.

[1-17] The immunosuppressive agent according to any one of [1-5] to [1-13] and [1-15] above, wherein the anti-CD80 antibody includes:
a heavy chain variable region that includes an amino acid sequence having an identity of 90% or more with the amino acid sequence of SEQ ID NO: 15; and
a light chain variable region that includes an amino acid sequence having an identity of 90% or more with the amino acid sequence of SEQ ID NO: 16.

[1-18] The immunosuppressive agent according to any one of [1-5] to [1-12] above, wherein the anti-CD80 antibody competes with the antibody according to any one of [1-13] to [1-17] above for binding to CD80.

[1-19] The immunosuppressive agent according to any one of [1-1] to [1-4] above, wherein the substance is an anti-PD-L1 antibody.

[1-20] The immunosuppressive agent according to [1-19] above, wherein the anti-PD-L1 antibody binds to PD-L1 with an equilibrium dissociation constant of $10^{-7}$ M or less.

[1-21] The immunosuppressive agent according to [1-19] or [1-20] above, wherein the anti-PD-L1 antibody inhibits cis-binding of PD-L1 to CD80.

[1-22] The immunosuppressive agent according to [1-21] above, wherein the cis-binding is mediated by at least
an amino acid corresponding to isoleucine at position 92 and/or leucine at position 104 of human CD80 having the amino acid sequence of SEQ ID NO: 1, and
an amino acid corresponding to asparagine at position 63 and/or glycine at position 119 of human PD-L1 having the amino acid sequence of SEQ ID NO: 3, or the cis-binding is mediated by at least
an amino acid corresponding to leucine at position 96 and/or leucine at position 107 of mouse CD80 having the amino acid sequence of SEQ ID NO: 2, and
an amino acid corresponding to valine at position 54, tyrosine at position 56, and/or glutamic acid at position 58 of mouse PD-L1 having the amino acid sequence of SEQ ID NO: 4.

[1-23] The immunosuppressive agent according to any one of [1-19] to [1-22] above, wherein the anti-PD-L1 antibody binds to
a region including an amino acid corresponding to asparagine at position 63 and/or glycine at position 119 of human PD-L1 having the amino acid sequence of SEQ ID NO: 3, or
a region including an amino acid corresponding to valine at position 54, tyrosine at position 56, and/or glutamic acid at position 58 of mouse PD-L1 having the amino acid sequence of SEQ ID NO: 4.

[1-24] The immunosuppressive agent according to any one of [1-1] to [1-23] above, for prevention and/or treatment of an autoimmune disease, an allergic disease, or a graft-versus-host disease.

[1-25] A method for preventing and/or treating an autoimmune disease, an allergic disease, or a graft-versus-host disease, the method including:
  administering an effective amount of the immunosuppressive agent according to any one of [1-1] to [1-23] above, to a subject in need thereof.
[1-26] The immunosuppressive agent according to any one of [1-1] to [1-23] above, for use in prevention and/or treatment of an autoimmune disease, an allergic disease, or a graft-versus-host disease.
[1-27] A use of the immunosuppressive agent according to any one of [1-1] to [1-23] above for production of a prophylactic and/or therapeutic agent for an autoimmune disease, an allergic disease, or a graft-versus-host disease.
[2-1] An anti-CD80 antibody or anti-PD-L1 antibody, wherein the antibody promotes binding of PD-L1 to PD-1.
[2-2] The anti-CD80 antibody or anti-PD-L1 antibody according to [2-1] above, wherein the anti-CD80 antibody or anti-PD-L1 antibody promotes the binding of PD-L1 present on the same cell as CD80, to PD-1.
[2-3] The anti-CD80 antibody or anti-PD-L1 antibody according to [2-1] or [2-2] above, wherein the anti-CD80 antibody or anti-PD-L1 antibody promotes the binding of PD-L1 to PD-1 so that the binding increases about twice or more.
[2-4] The anti-CD80 antibody or anti-PD-L1 antibody according to any one of [2-1] to [2-3] above, wherein PD-1 is on T cells.
[2-5] The antibody according to any one of [2-1] to [2-4] above, wherein the antibody is an anti-CD80 antibody.
[2-6] The antibody according to [2-5] above, wherein the antibody binds to CD80 with an equilibrium dissociation constant of $10^{-7}$M or less.
[2-7] The antibody according to [2-5] or [2-6] above, wherein the antibody inhibits the cis-binding of CD80 to PD-L1.
[2-8] The antibody according to [2-7] above, wherein the cis-binding is mediated by at least
  a region including an amino acid corresponding to isoleucine at position 92 and/or leucine at position 104 of human CD80 having the amino acid sequence of SEQ ID NO: 1, and
  a region including an amino acid corresponding to asparagine at position 63 and/or glycine at position 119 of human PD-L1 having the amino acid sequence of SEQ ID NO: 3, or
  the cis-binding is mediated by at least
  a region including an amino acid corresponding to leucine at position 96 and/or leucine at position 107 of mouse CD80 having the amino acid sequence of SEQ ID NO: 2, and
  a region including an amino acid corresponding to valine at position 54, tyrosine at position 56, and/or glutamic acid at position 58 of mouse PD-L1 having the amino acid sequence of SEQ ID NO: 4.
[2-9] The antibody according to any one of [2-5] to [2-8] above, the antibody binding to
  a region including an amino acid corresponding to isoleucine at position 92 and/or leucine at position 104 of human CD80 having the amino acid sequence of SEQ ID NO: 1, or
  a region including an amino acid corresponding to leucine at position 96 and/or leucine at position 107 of mouse CD80 having the amino acid sequence of SEQ ID NO: 2.
[2-10] The antibody according to any one of [2-5] to [2-9] above, wherein the antibody does not substantially inhibit binding of CD80 to CTLA-4.
[2-11] The antibody according to any one of [2-5] to [2-10] above, wherein the antibody does not strongly inhibit binding of CD80 to CD28.
[2-12] An anti-CD80 antibody, wherein the antibody promotes binding of PD-L1 present on the same cells as CD80 to PD-1, and does not strongly inhibit binding of CD80 to CD28.
[2-13] (1) The antibody according to any one of [2-5] to [2-12] above, the antibody including:
  a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and
  a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14;
  (2) a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and
  a light chain variable region that includes a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22;
  (3) a heavy chain variable region that includes a heavy chain CDR1 including the amino acid sequence of SEQ ID NO: 12, a heavy chain CDR2 including the amino acid sequence of SEQ ID NO: 13, and a heavy chain CDR3 including the amino acid sequence of SEQ ID NO: 14; and
  a light chain variable region that includes a light chain CDR1 including the amino acid sequence of SEQ ID NO: 9, a light chain CDR2 including the amino acid sequence of SEQ ID NO: 10, and a light chain CDR3 including the amino acid sequence of SEQ ID NO: 11;
  or
  (4) a heavy chain variable region that includes a heavy chain CDR1 including the amino acid sequence of SEQ ID NO: 20, a heavy chain CDR2 including the amino acid sequence of SEQ ID NO: 21, and a heavy chain CDR3 including the amino acid sequence of SEQ ID NO: 22; and
  a light chain variable region that includes a light chain CDR1 including the amino acid sequence of SEQ ID NO: 17, a light chain CDR2 including the amino acid sequence of SEQ ID NO: 18, and a light chain CDR3 including the amino acid sequence of SEQ ID NO: 19.
[2-14] The antibody according to any one of [2-5] to [2-13] above, the antibody including:
  a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14.

[2-15] The antibody according to any one of [2-5] to [2-13] above, the antibody including:

a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and a light chain variable region that includes a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22.

[2-16] The antibody according to any one of [2-5] to [2-14] above, wherein the anti-CD80 antibody includes:

a heavy chain variable region that includes an amino acid sequence having an identity of 90% or more with the amino acid sequence of SEQ ID NO: 7; and a light chain variable region that includes an amino acid sequence having an identity of 90% or more with the amino acid sequence of SEQ ID NO: 8.

[2-17] The antibody according to any one of [2-5] to [2-13] and [2-15] above, wherein the anti-CD80 antibody includes:

a heavy chain variable region that includes an amino acid sequence having an identity of 90% or more with the amino acid sequence of SEQ ID NO: 15; and a light chain variable region that includes an amino acid sequence having an identity of 90% or more with the amino acid sequence of SEQ ID NO: 16.

[2-18] The antibody according to any one of [2-1] to [2-12] above, wherein the antibody competes with the antibody according to any one of the above [2-13] to [2-17] for binding to CD80.

[2-19] The antibody according to any one of the above [2-1] to [2-4], wherein the antibody is an anti-PD-L1 antibody.

[2-20] The antibody according to [2-19] above, wherein the antibody binds to PD-L1 with an equilibrium dissociation constant of $10^{-7}$M or less.

[2-21] The antibody according to the above [2-19] or [2-20], wherein the antibody inhibits the cis-binding of PD-L1 to CD80.

[2-22] The antibody according to [2-21] above, wherein the cis-binding is mediated by at least a region including an amino acid corresponding to isoleucine at position 92 and/or leucine at position 104 of human CD80 having the amino acid sequence of SEQ ID NO: 1, and a region including an amino acid corresponding to asparagine at position 63 and/or glycine at position 119 of human PD-L1 having the amino acid sequence of SEQ ID NO: 3, or the cis-binding is mediated by at least a region including an amino acid corresponding to leucine at position 96 and/or leucine at position 107 of mouse CD80 having the amino acid sequence of SEQ ID NO: 2, and a region including an amino acid corresponding to valine at position 54, tyrosine at position 56, and/or glutamic acid at position 58 of mouse PD-L1 having the amino acid sequence of SEQ ID NO: 4.

[2-23] The antibody according to any one of [2-19] to [2-22] above, wherein the antibody binds to a region including an amino acid corresponding to asparagine at position 63 and/or glycine at position 119 of human PD-L1 having the amino acid sequence of SEQ ID NO: 3, or a region including an amino acid corresponding to valine at position 54, tyrosine at position 56, and/or glutamic acid at position 58 of mouse PD-L1 having the amino acid sequence of SEQ ID NO: 4.

[2-24] An anti-CD80 antibody including:

(1) a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14;

(2) a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and a light chain variable region that includes a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22;

(3) a heavy chain variable region that includes a heavy chain CDR1 including the amino acid sequence of SEQ ID NO: 12, a heavy chain CDR2 including the amino acid sequence of SEQ ID NO: 13, and a heavy chain CDR3 including the amino acid sequence of SEQ ID NO: 14; and a light chain variable region that includes a light chain CDR1 including the amino acid sequence of SEQ ID NO: 9, a light chain CDR2 including the amino acid sequence of SEQ ID NO: 10, and a light chain CDR3 including the amino acid sequence of SEQ ID NO: 11;

or (4) a heavy chain variable region that includes a heavy chain CDR1 including the amino acid sequence of SEQ ID NO: 20, a heavy chain CDR2 including the amino acid sequence of SEQ ID NO: 21, and a heavy chain CDR3 including the amino acid sequence of SEQ ID NO: 22; and a light chain variable region that includes a light chain CDR1 including the amino acid sequence of SEQ ID NO: 17, a light chain CDR2 including the amino acid sequence of SEQ ID NO: 18, and a light chain CDR3 including the amino acid sequence of SEQ ID NO: 19.

[2-25] The antibody according to [2-24] above, the antibody including:
a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11; and
a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14.

[2-26] The antibody according to [2-24] above, the antibody including:
a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19; and
a light chain variable region that includes a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22.

[2-27] The antibody according to [2-24] or [2-25] above, wherein the anti-CD80 antibody includes:
a heavy chain variable region that includes an amino acid sequence having an identity of 90% or more with the amino acid sequence of SEQ ID NO: 7; and
a light chain variable region that includes an amino acid sequence having an identity of 90% or more with the amino acid sequence of SEQ ID NO: 8.

[2-28] The antibody according to [2-24] or [2-26] above, wherein the anti-CD80 antibody includes:
a heavy chain variable region that includes an amino acid sequence having an identity of 90% or more with the amino acid sequence of SEQ ID NO: 15; and
a light chain variable region that includes an amino acid sequence having an identity of 90% or more with the amino acid sequence of SEQ ID NO: 16.

[2-29] An anti-CD80 antibody that competes with the antibody according to any one of [2-24] to [2-28] above for binding to CD80.

[2-30] An anti-CD80 antibody binding to:
a region including an amino acid corresponding to isoleucine at position 92 and/or leucine at position 104 of human CD80 having the amino acid sequence of SEQ ID NO: 1; or
a region including an amino acid corresponding to leucine at position 96 and/or leucine at position 107 of mouse CD80 having the amino acid sequence of SEQ ID NO: 2.

[2-31] The antibody according to any one of [2-24] to [2-30] above, wherein the antibody binds to CD80 with an equilibrium dissociation constant of $10^{-7}$M or less.

[2-32] An anti-PD-L1 antibody binding to:
a region including an amino acid corresponding to asparagine at position 63 and/or glycine at position 119 of human PD-L1 having the amino acid sequence of SEQ ID NO: 3, or
a region including an amino acid corresponding to valine at position 54, tyrosine at position 56, and/or glutamic acid at position 58 of mouse PD-L1 having the amino acid sequence of SEQ ID NO: 4.

[2-33] The antibody according to [2-32] above, which binds to PD-L1 with an equilibrium dissociation constant of $10^{-7}$M or less.

[2-34] The antibody according to any one of the above [2-1] to [2-33], wherein the antibody is a monoclonal antibody.

[2-35] The antibody according to any one of the above [2-1] to [2-34], wherein the antibody is an isolated monoclonal antibody.

[2-36] A pharmaceutical composition containing the antibody according to any one of [2-1] to [2-35] above.

[2-37] The pharmaceutical composition according to the above [2-36], for the suppression of immunity, or the prevention and/or treatment of a disease characterized by enhancement of immunity.

[2-38] An immunosuppressive agent containing the antibody according to any one of [2-1] to [2-35] as an active ingredient.

[2-39] The immunosuppressive agent according to [2-38] above, further containing a pharmaceutically acceptable carrier.

[2-40] A method for suppressing immunity, the method including administering an effective amount of the antibody according to any one of [2-1] to [2-35] above, to a subject in need thereof.

[2-41] The antibody according to any one of [2-1] to [2-35] above, for use in immunosuppression.

[2-42] A use of the antibody according to any one of [2-1] to [2-35] above, for the production of an immunosuppressive agent.

[2-43] A prophylactic and/or therapeutic agent for a disease characterized by enhanced immunity, which contains the antibody according to any one of [2-1] to [2-35] above as an active ingredient.

[2-44] The prophylactic and/or therapeutic agent according to [2-43] above, further containing a pharmaceutically acceptable carrier.

[2-45] A method for preventing and/or treating a disease characterized by enhanced immunity, the method including administering an effective amount of the antibody according to any one of [2-1] to [2-35] above, to a subject in need thereof.

[2-46] The antibody according to any one of [2-1] to [2-35] above, for use in the prevention and/or treatment of a disease characterized by enhanced immunity

[2-47] A use of the antibody according to any one of [2-1] to [2-35] above, for the production of a prophylactic and/or therapeutic agent for a disease characterized by enhanced immunity.

[2-48] The prophylactic and/or therapeutic agent according to the above [2-43] or [2-44], the method according to [2-45] above, the antibody according to [2-46] above, or the use according to [2-47] above, wherein the disease characterized by enhanced immunity is an autoimmune disease, an allergic disease, or a graft-versus-host disease.

[2-49] The prophylactic and/or therapeutic agent, method, antibody, or use according to [2-48] above, wherein the disease characterized by enhanced immunity is an autoimmune disease.

[2-50] The prophylactic and/or therapeutic agent, method, antibody, or use according to [2-49] above, the autoimmune disease is selected from the group consisting of Behcet's disease, systemic lumpus erythematosus, multiple sclerosis, scleroderma, polymyositis, dermatomyositis, periarteritis nodosa, aortitis syndrome, malignant rheumatoid arthritis, rheumatoid arthritis, juvenile idiopathic arteritis, Wegener's granulomatosis, mixed connective tissue disease, Sjogren's syndrome, Adult-onset Still's disease, allergic granulomatous angiitis, hypersensitivity vasculitis, Cogan's syndrome, RS3PE, temporal arteritis, polymyalgia rheumatica, fibromyalgia, antiphospholipid antibody syndrome, eosinophilic fasciitis, IgG4-related diseases, Guillain-Barre syndrome, myasthenia gravis, chronic atrophic gastritis, autoimmune hepatitis, primary biliary cirrhosis, aortitis syndrome, Goodpasture syndrome, rapidly progressive glomerulonephritis, megaloblastic anemia, autoimmune hemolytic anemia, autoimmune neutropenia, idiopathic thrombocytopenic purpura, Basedow's disease, Hashimoto disease, autoimmune adrenal insufficiency, primary hypothyroidism, idiopathic Addison disease, type 1 diabetes, slowly progressive type I diabetes, chronic discoid lupus erythematosus, circumscribed scleroderma, psoriasis, psoriatic arthritis, pemphigus, pemphigoid, gestational herpes, linear IgA bullous dermatosis, acquired epidermolysis bullosa, allopecia areata, white spots, vitiligo vulgaris, atopic dermatitis, neuromyelitis optica, Chronic inflammatory demyelinating polyneuropathy, sarcoidosis, bullous pemphigoid, giant cell arteritis, amyotrophic lateral sclerosis, eosinophilic granulomatosis with polyangiitis, Harada disease, autoimmune optic neuropathy, idiopathic azoospermia, habitual abortion, inflammatory bowel disease, and celiac disease.

[2-51] The prophylactic and/or therapeutic agent, method, antibody, or use according to [2-49] or [2-50] above, wherein the autoimmune disease is type I diabetes, multiple sclerosis, systemic lupus erythematosus, or rheumatoid arthritis.

[2-52] The prophylactic and/or therapeutic agent, method, antibody or use according to any one of [2-49] to [2-51] above, wherein the autoimmune disease is multiple sclerosis.

[2-53] The prophylactic and/or therapeutic agent, method, antibody or use according to [2-52] above, wherein the multiple sclerosis is systemic scleroderma or progressive systemic sclerosis.

[2-54] A polynucleotide encoding the antibody according to any one of the above [2-1] to [2-35].

[2-55] A vector including the polynucleotide according to [2-54] above.

[2-56] A host cell containing the polynucleotide according to [2-54] above or the vector according to [2-55] above.

All references cited herein are hereby incorporated by reference.

All of the above description is non-limiting and can be modified without departing from the scope of the invention as defined in the appended claims. In addition, the examples below are all non-limiting examples and are provided solely to illustrate the invention.

EXAMPLES

Materials and Methods

Cell Culture

DO11.10 cells, TCRα/β-deficient BW-1100.129.237 cells (White, J. et al., J. Immunol. 143, 1822-5 (1989)) (provided by Leszek Ignatowicz, Georgia Regents University), IIA1.6 cells, and E.G7 cells were maintained in RPMI1640 medium (Gibco) supplemented with 10% (v/v) bovine fetal serum (FBS, Biowest), 0.5 mM monothioglycerol (Wako), 2 mM L-alanyl-L-glutamine dipeptide (Gibco), 100 U/mL penicillin (Nacalai Tesque), and 100 μg/mL streptomycin (Nacalai Tesque). Plat-E cells were maintained in Dulbecco's modified Eagle's medium (D'MEM, Invitrogen) supplemented with 10% (v/v) FBS, 100 U/mL penicillin (Nacalai Tesque), and 100 μg/mL streptomycin (Nacalai Tesque).

Plasmid and Retroviral Gene Transfer

The cDNA fragment was amplified by PCR and cloned into a retrovirus expression plasmid vector modified from pFB-ires-Neo (Agilent). To create a plasmid library of mouse and human PD-L1 mutants, the IgV domain of PD-L1 was amplified by Thermo-Start Taq DNA polymerase (Thermo Fisher Scientific) containing 400 μM $MnCl_2$ and cloned into pFB-ires-Neo. PD-L1 and CD80 mutants with site-specific mutations were generated by overhang PCR. To control the expression level, a fragment of cDNA was cloned into a retrovirus expression plasmid vector (the promoter region was changed to EF-1α (human elongation factor-1 alpha), as well as CAG, CMV, and MC1 promoters) modified from pSUPER.retro.puro (OligoEngine). The plasmid was transfected into Plat-E cells cultured in D'MEM (high glucose) (Gibco) supplemented with 20% (v/v) FBS, 100 U/ml penicillin (Nacalai Tesque) and 100 μg/ml streptomycin (Nacalai Tesque), using FuGENE® HD (Promega), and genes were transduced into target cells using a supernatant containing the virus. Infected cells were selected by using G418 (Wako), puromycin (Sigma-aldrich), Zeocin (InvivoGen), or Blasticidin (InvivoGen).

Preparation of Target Gene Knockout Cell Line by CRISPR/Cas9

PD-1 deficient IIA1.6 cells, PD-1, PD-L1, CD28 deficient DO11.10 cells, and PD-1 deficient BW-1100.129.237 were prepared using the CRISPR/Cas9 system. The guide RNA sequences are shown in the table below. Guide RNA sequences were cloned into pEF-BOS-Cas9-U6-guide (this was modified from pEF-BOS (Mizushima, S. & Nagata, S. Nucleic Acids Res. 18, 5322 (1990)) so as to express a humanized cas9 cDNA (Addgene) with or without the D10A mutation under the human EF-1α-promoter, and to express guide RNAs under the reverse U6 promoter). The plasmid was transfected into cells by electroporation (Nucleofector II®, Lonza). Cells in which the expression of the target gene had disappeared were sorted using a cell sorter (MoFlo XDP, Beckman Coulter). Cell clones were obtained by limiting dilution, and a loss-of-function mutation of the target gene and lack of expression of the same were confirmed by sequencing and flow cytometry, respectively.

TABLE 1

| Cell | Gene | Cas9 | Guide RNA |
|---|---|---|---|
| IIAdL1 | Cd274 | WT | GTATGGCAGCAACGTCACGA |
| DO11.10TKO | Cd274 | WT | GTATGGCAGCAACGTCACGA |
|  | Pdcd1 | WT | GACAGTGGCATCTACCTCTG |
|  | Cd28 | WT | ACTCGGCATTCGAGCGAAAC[*1] |
|  |  |  | GCTGTTCACGCCCTTGTACA[*1] |
| DO11.10-Pdcd1[-/-] | Pdcd1 | D10A | GTTCAGAAAAGATGTCAGAA[*2] |
|  |  |  | GTGCTCTCAGACCCATTCCA[*2] |
|  |  |  | AGACCCTCCACAGAGAGCAC[*2] |
|  |  |  | ATGCTAATGGCTGAAGAATC[*2] |
| BW-Pdcd1[-/-] | Pdcd1 | D10A | GTTCAGAAAAGATGTCAGAA[*2] |
|  |  |  | GTGCTCTCAGACCCATTCCA[*2] |
|  |  |  | AGACCCTCCACAGAGAGCAC[*2] |
|  |  |  | ATGCTAATGGCTGAAGAATC[*2] |

[*1]Two guide RNAs were used simultaneously for increased efficiency.
[*2]Exons 2, 3, and 4 were targeted by performing the transfection with staggered nicks.

Mouse

C57BL/6N mice were purchased from SLC and bred in an environmentally controlled clean room under specific pathogen-free conditions. Mice of identical age and sex were used in each experiment. All mouse protocols have been approved by the Institutional Animal Care and Use Committee (IACUC) of Tokushima University.

Preparation of Target Gene Knockout Mice and Knock-In Mice

By transfecting Cas9 mRNA, gRNA, and single-strand oligodeoxynucleotide (ssODN) into the C57BL/6N zygote by electroporation in the above-described manner (Hashimoto, M. & Takemoto, T., Sci. Rep. 5, 11315 (2015)), C57BL/6N-Cd274[-/-] (PD-L1 knockout mice), C57BL/6N-Cd80[-/-], C57BL/6N-Cd274[Y56A], and C57BL/6N-Cd80[L107E] mice were generated. The nucleotide sequences of the guide RNAs and ssODNs used to prepare C57BL/6N-Cd80[-/-], C57BL/6N-Cd274[Y56A] and C57BL/6N-Cd80[L107E] mice are shown in the table below. One nucleotide was inserted into the C57BU6N-Cd274[-/-] mouse, resulting in the production of a premature stop codon at Y56. One nucleotide was inserted into the C57BL/6N-Cd80[-/-] mouse, resulting in a frameshift at G109, the addition of 20 unrelated amino acids, and the production of premature stop codons. First-generation mosaic mice were crossed with C57BL/6N wild-type mice to obtain heterozygous mice, and heterozygous mice were crossed with each other to obtain homozygous mice. A primer set of 5'-GAGACACTATCTCTAAAAAT-3' and 5'-TTAGTAGAGGTCTCCACCTT-3' for CD80 and a primer set of 5'-GTTCATGTGATTCCCTAAAT-3' and 5'-CTGAAGTTGCTGTGCTGAGG-3' for PD-L1 were used for genomic fragment amplification. Amplified fragments were sequenced (ABI Prism®3700 DNA Analyzer, Thermo Fisher Scientific) or used for restriction length polymorphism analysis.

TABLE 2

| Mouse | Guide RNA | ssODN |
|---|---|---|
| C57BL/6N-Cd274[-/-] | 5'-TTGCGTTAGTGGTGTACT-3' | — |
| C57BL/6N-Cd80[-/-] | 5'-TCTGAAAGGACCAGGCCC-3' | — |
| C57BL/6N-Cd274[Y56A] | 5'-TTGCGTTAGTGGTGTACT-3' | 5'-CCCTGTAGAACGGGAGCTGGACCTGCTTGCGTTAGTGGTGGCCTGGGAAAAGGAAGATGAGCAAGTGATTCAGTTTGTGGCA-3' |
| C57BL/6N-Cd80[L107E] | 5'-TCTGAAAGGACCAGGCCC-3' | 5'-CCGGACTTTATATGACAACACTACCTACTCTCTTATCATCGAAGGCCTGGTCCTTTCAGACCGGGGCACATACAGCTGTGTCG-3' |

Stimulation of DO11.10 T Cells and TCR-Reconstructed Cells

DO11.10 T cells ($5 \times 10^4$ cells/well) were placed in 96-well round bottom plates (BD Bioscinences), and were stimulated with IIAdL1 cells ($1 \times 10^4$ cells/well) pulsed with a predetermined amount of OVA$_{323-339}$ peptide (ISQAVHAA-HAEINEAGR, >95% purity, Sigma-Aldrich Japan or Eurofins Genomics) for 12 to 14 hours. BW-Pdcd1[-/-] cells were prepared by knocking out the PD-1 gene of BW-1100.129.237 cells using the CRISPR/Cas9 system. BW-Pdcd1[-/-] cells were reconstituted with CD3S, CD3c, CD28 and PD-1, together with CD8α/CD8β/OT-I TCR or CD4/OT-II TCR, whereby BW-OT-I cells or BW-OT-II cells were prepared, respectively. BW-OT-I and BW-OT-II cells ($2.5 \times 10^4$ cells/well) were placed in 96-well round-bottomed plates, and were stimulated with BM-DC or splenic DC ($5 \times 10^3$ cells/well) pulsed with a predetermined amount of MHC I-restricted OVA$_{257-264}$ peptide (SIINFEKL, >98% purity, MBL) or MHC II-restricted OVA$_{323-339}$ peptide for 12-14 hours. Added were 1 µg/ml anti-PD-L1 antibody (1-111A), 5 µg/ml anti-PD-L2 antibody (TY25) or rat IgG2a isotype control (RTK2758, Biolegend), where indicated. The concentration of IL-2 in the supernatant of the medium was determined by ELISA (Biolegend). PD-1 mediated inhibition was calculated by comparing the amount of IL-2 when PD-1 was activated and the amount of IL-2 when PD-1 was not activated.

Flow Cytometric Analysis

Cultured cells and primary cells were stained with the antibodies or soluble chimeric proteins shown in the drawing. Splenic cells were stimulated with LPS (1 µg/ml, Escherichia coli 0111: B4, Merck) or poly(I:C) (20 µg/ml, Merk) for 16 to 18 hours before the cells were stained. Antibodies to mouse CD8α (5H10), CD28 (37.51), and PD-L1 (1-111A, MIH5) were purchased from Thermo Fisher Scientific. Antibodies to mouse PD-1 (RMP1-30), MHC II (M5/114.15.2), B220 (RA3-6B2), F4/80 (BM8), CD80 (16-10A1), CD86 (GL-1), DYKDDDDK tag (L5), CD19 (6D5), CD3e (17A2), CD4 (RM4-5), CD8a (53-6.7), CD11b (M1/70), CD11c (N418), and CD317 (927) were purchased from Biolegend. Streptavidin-Phycoerythrin (PE) and Streptavidin-Allophycocyanin (APC) were purchased from Biolegend. Isotype control antibodies to rat IgG2a (RTK2758), rat IgG2b (RTK4530), and hamster IgG (HTK888) were purchased from Biolegend. Unless otherwise stated, 30 µg/ml biotinylated 1-111A was used for the detection of mouse PD-L1. The cDNA fragments encoding the extracellular regions of mouse PD-1 (amino acid 1-167), human PD-1 (amino acid 1-167), mouse CD28 (amino acid 1-149), and mouse CTLA-4 (amino acid 1-162) were amplified by PCR for the preparation of soluble chimeric proteins. Five-stranded coiled coil domains of cartilage oligomer matrix proteins including the DYKDDDDK tag (Terskikh, A. V et al., Proc. Natl. Acad. Sci. U. S A. 94, 1663-8 (1997))

were fused to the C-terminus of each protein. Then, the chimeric cDNA was cloned into an expression vector modified from pEBMulti-Neo (Wako). The plasmids were transfected into 293T cells or Plat-E cells using Avalanche-Omni transfection reagent (EZ Biosystems) and the culture supernatants were collected after 48 hours and 96 hours. The supernatants were diluted and used for staining. Binding of chimeric proteins on cells was detected by an anti-DYKDDDDK tag antibody (L5). Data were acquired using Gallios (Beckman Coulter) and analyzed using FlowJo (Tree Star).

Co-Immunoprecipitation

The DYKDDDDK tag was fused to the C-termini of PD-L1 and PD-L1Y56A. SHSLQKYYITGEAEGFPATA tags (hER tag) recognized by a rabbit polyclonal antibody against human ERα protein (HC-20, Santa Cruz Biotechnology) were fused to the C-termini of CD80, CD80L107E, and CD86. IIAdL1 cells expressing the tagged protein in the prescribed combination were extensively washed with PBS and treated with $BS^3$ (1 mM, Thermo Fisher Scientific), which was a water-soluble, non-cleaving, and membrane-impermeable crosslinker, for 30 minutes. After the cross-linking reaction was ended with 25 mM Tris, cells were lysed with a lysis buffer containing 1% NP-40. Proteins labeled with the DYKDDDDK tag were immunoprecipitated with anti-FLAG M2 agarose beads (Merk), separated by SDS-PAGE under reducing conditions, and transcribed to PVDF membranes. Proteins labeled with the DYKDDDDK tags and the hER tags were detected with use of the anti-DYKDDDDK antibody (L5) and the HC-20 antibody, and subsequently detected by an IRDye800-anti-rat IgG(H+L) antibody and an IRDye680-anti-rabbit IgG(H+L) (LI-COR Biosciences) antibody. Fluorescence signals on the membranes were detected by the Odyssey Imaging System (LI-COR Biosciences).

Preparation of BM-DC

BM cells were harvested from the femur and tibia of mice and were cultured in RPMI1640 medium supplemented with 10% (v/v) FBS, 0.5 mM monothioglycerol, 2 mM L-alanyl-L-glutamine dipeptide, 100 U/ml penicillin, 100 μg/ml streptomycin, and 20 ng/ml recombinant mouse GM-CSF (Biolegend). On day 4, two-thirds of the medium was replaced with fresh medium. Non-adherent cells were collected on day 6, and CD11c⁺ cells were collected for immunity experiments in mice and CD86⁺ cells for in vitro co-culture experiments using the BD iMag Cell Separation System (BD Biosciences). The isolated cells were stimulated with LPS (1 μg/ml). For dendritic cell vaccine therapy in mice with E.G7, 100 μg/ml OVA protein (low endotoxin, Wako) was added. Non-adherent cells were harvested after 16 to 18 hours and used for further experiments.

Preparation of TG-MΦ

Naive mice were intraperitoneally administered with 2 ml of 3% Brewer thioglycolate medium (BD Biosciences). Four days after, peritoneal exudate cells were collected and seeded on tissue culture plates at 37° C. for 2 hours. Floating cells were extensively washed away and strongly adherent cells were stimulated with LPS (1 μg/ml) for 16 to 18 hours and used for flow cytometric analysis. F4/80⁺ cells were purified (>95% purity) using a cell sorter for in vitro co-culture assay.

Isolation of Splenic DC

The spleen was treated with collagenase (1 mg/ml, Wako) for 20 minutes at 37° C. and ground to prepare a single cell suspension. After erythrocyte lysis, whole splenic cells were stimulated with LPS (1 μg/ml) for 16 to 18 hours. Cells were harvested, stained with a bio-CD11c antibody and then PE-streptavidin, and CD11c⁺ cells were concentrated with anti-PE magnetic particles and the BD iMag Cell Separation System. B220⁻F4/80⁻CD3⁻CD11c⁺CD8α⁺CD11b⁻ cells (CD8α⁺DC) or B220⁻F4/80⁻CD3⁻CD11c⁺CD8α⁻CD11b⁺ cells (CD11b⁺ DC) were sorted by a cell sorter (CD8α⁺DC; >85% purity, and CD11b⁺DC; >90% purity, respectively), and were used as antigen-presenting cells in in vitro co-culture assays.

Protein Structure

The structures of mouse PD-L1 and CD80 were predicted by SWISS-MODEL swissmodel.expasy.org/) based on the previously reported structures of IgV domains of human PD-L1 (PDB ID: 4Z18) and mouse CD80 (PDB ID: 4RWH), respectively The structures of human CD80 (PDB ID: 1DR9) and CD86 (PDB ID: 1NCN) were analyzed by the UCSF Chimera Software.

Induction of T Cell Response to OVA

The footpads of naive mice were inoculated with, as an antigen, OVA protein (100 μg) emulsified in Freund's complete adjuvant (BD Biosciences). One week after inoculation with the antigen, 5×10⁵ cells from the popliteal lymph nodes were stimulated with OVA protein (100 μg/ml), $OVA_{257-264}$ peptide (100 nM), and $OVA_{323-339}$ peptide (3 μM) for 48 hours. The concentrations of IL-2 and IFN-γ in the culture supernatants were determined by ELISA (Biolegend).

Tumor Immunotherapy

On day 0, 5×10⁵ E.G7 lymphoma cells were subcutaneously administered to the shaved left abdomens of the mice. On days 5 and 12, OVA protein (100 μg) mixed with poly(I:C) (50 μg) in PBS was subcutaneously inoculated in the vicinity of the tumors. Alternatively, on days 3 and 10, 4.5×10⁵ LPS-activated BM-DCs pulsed with OVA protein were subcutaneously inoculated near the tumors. Tumor sizes were measured with calipers every 3 days. Tumor volumes were calculated using the following formula: 1/2×(shorter diameter)²×(longer diameter).

Experimental Autoimmune Encephalomyelitis (EAE)

Induction of EAE was performed according to an existing protocol (Stromnes, I. M. & Goverman, Nat. Protoc. 1, 1810-1819 (2006)). Briefly, on day 0, the mice were subcutaneously inoculated with, as an antigen, $MOG_{35-55}$ peptide (200 μg, MEVGWYRSPFSRVVHLYRNGK, >95% purity, Eurofins) emulsified in Freund's incomplete adjuvant (BD Biosciences) supplemented with *Mycobacterium tuberculosis* H37RA (200 μg, BD Biosciences). On days 0 and 2, 200 ng of pertussis toxin (List Biological Laboratories) was administered intraperitoneally. Clinical scores were evaluated in blind every day as follows: 0, no clinical signs; 1, dragging; 2, hindlimb weakness; 3, hindlimb paralysis; 4, hindlimb and forelimb paralysis; 5, moribund state. To assess the in vitro recall response, 1×10⁶ mouse splenic cells started to be stimulated with 5 or 50 μg/ml $MOG_{35-55}$ peptide 7 days after inoculation with the antigen, and the stimulation was continued for 66 hours. The concentration of IL-17A in the culture supernatant was determined by ELISA (Thermo Fisher Scientific).

Statistics

An unpaired student's two-sided t-test was used for comparison between the two groups. One-way analysis of variance (ANOVA) or two-way ANOVA with post-test was used for multiple comparisons. $p<0.05$ was considered statistically significant. In the drawing, the error bars denote s.e.m. FIGS. 1 to 12, 17, 19, 21 to 28 and 30 to 34 show representative data from three or more independent experiments.

[Result]
Test 1: Interference with PD-L1/PD-1 Binding and Subsequent PD-1 Mediated Inhibition by Cis-PD-L1/CD80 Interactions In IIA1.6 cells expressing PD-L1 but not PD-L2, the PD-L1 gene was knocked out using the CRISPR/Cas9 system to obtain IIAdL1 cells. PD-L1, PD-L2, CD80 and CD86 were overexpressed in various combinations in IIAdL1 cells, and were stained with soluble mouse PD-1 extracellular region (PD-1-EC) protein, whereby PD-1 binding ability was evaluated (FIG. 1). The binding of PD-1-EC to PD-L1 was strongly blocked by co-expression of CD80 in IIAdL1-PD-L1 cells, and was not blocked by co-expression of CD86 (FIG. 1, upper row). This result indicates that CD80 interacts with PD-L1 on the same antigen-presenting cells, and this cis-PD-L1/CD80 interaction interferes with PD-L1/PD-1 binding. On the other hand, the binding of PD-1-EC to PD-L2 was not affected by the co-expression of CD80 and CD86 in IIAdL1-PD-L2 cells (FIG. 1, lower row). Addition of IIAdL1-CD80 cells to IIAdL1-PD-L1 cells (which allows trans-PD-L1/CD80 interactions rather than cis-PD-L1/CD80 interactions) did not affect the binding of PD-1-EC to IIAdL1-PD-L1 cells (FIG. 2). This result indicates that it is necessary that CD80 be expressed on the same cells as PD-L1 for the interference with PD-L1/PD-1 binding. Notably, the cis-PD-L1/CD80 interaction did not interfere with the CD80/CD28 binding and the CD80/CTLA-4 binding (data not shown). When adjacent proteins on the cell surface were cross-linked with a cell-impermeable cross-linking agent, CD80 was co-immunoprecipitated with PD-L1, and CD86 was not (FIG. 3). This result further supports the cis interaction between PD-L1 and CD80.

Figure 4:
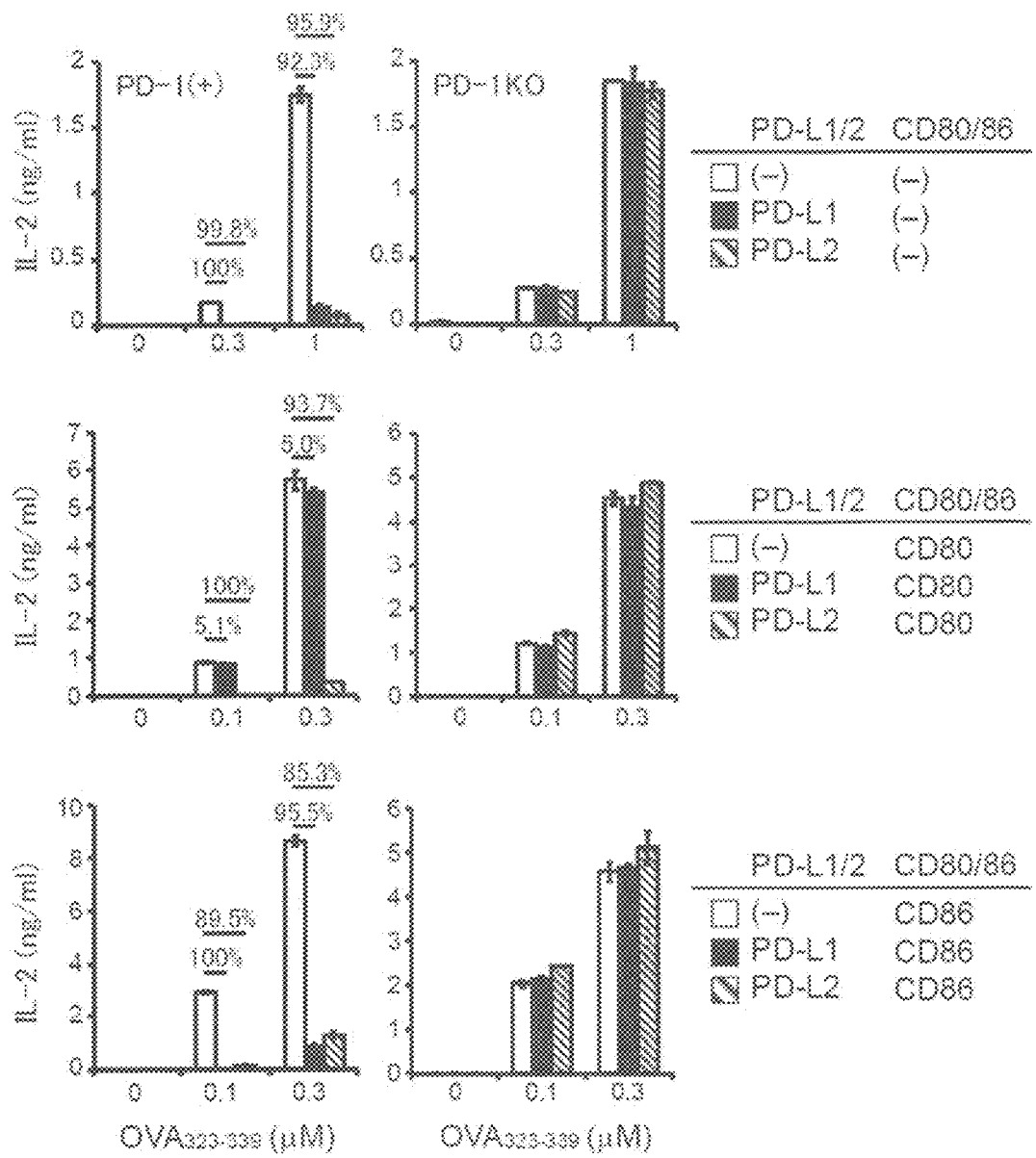
FIG. 4 shows IL-2 production from T cells when antigen-presenting cells pulsed with antigen peptide in the amounts shown in the drawing, and PD-1 expressing DO11.10 T cells (PD-1 (+)) (left) or PD-1 deficient DO11.10 T cells (PD-1KO) (right), were co-cultured. The rates of inhibition of IL-2 production mediated by PD-1 are shown in the drawing.

To investigate its functional significance, IIAdL1 cells overexpressing PD-L1, PD-L2, CD80 and CD86 in various combinations were used as antigen-presenting cells to stimulate DO11.10 T cells. IL-2 production from DO11.10 T cells by antigen stimulation was strongly inhibited when PD-L1 or PD-L2 was expressed on antigen-presenting cells (FIG. 4, upper row). Inhibition of IL-2 production was not observed in PD-1 knockout DO11.10 (DO11.10-Pdcd1.$^{-/-}$) T cells, which proves that PD-L1 or PD-L2-mediated inhibition was PD-1 dependent. Co-expression of CD80 strongly suppressed the PD-1-mediated inhibitory effect elicited by IIAdL1-PD-L1 cells, but did not suppress the inhibitory effect by IIAdL1-PD-L2 cells (FIG. 4, middle row). Co-expression of CD86 did not suppress the PD-1-mediated inhibitory effect elicited by IIAdL1-PD-L1 cells and IIAdL1-PD-L2 cells (FIG. 4, lower row). Therefore, it was shown that CD80 interacts in cis with PD-L1 and prevents PD-L1 from eliciting PD-1 function in T cell activation.

Figure 5:
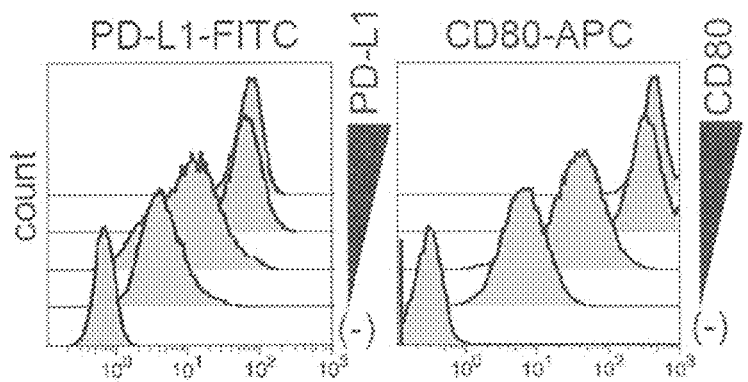
FIG. 5 shows the intensities of the binding of PD-L1 antibody (left) and CD80 antibody (right) to IIAdL1 cells expressing PD-L1 and CD80 at various levels.
Figure 6:
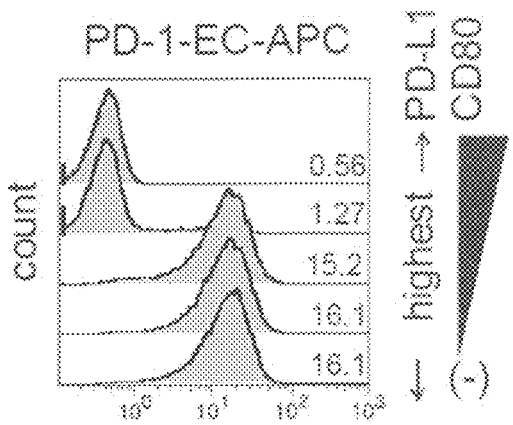
FIG. 6 shows the intensities of the binding of PD-1-EC to IIAdL1 cells that expresses PD-L1 at the highest level and expresses CD80 at various levels.
Figure 7:
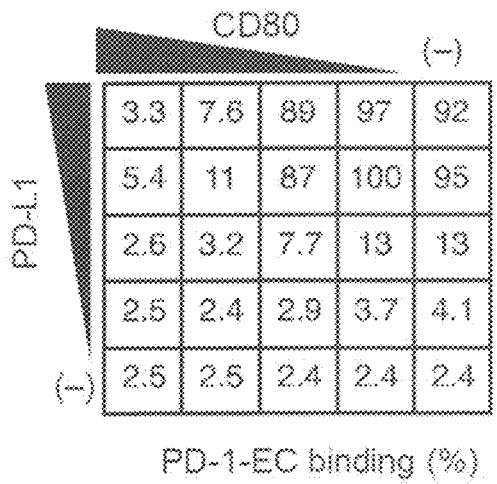
FIG. 7 shows the relative intensities of the binding of PD-1-EC to IIAdL1 cells expressing PD-L1 and CD80 at 25 different expression levels.
Figure 8:
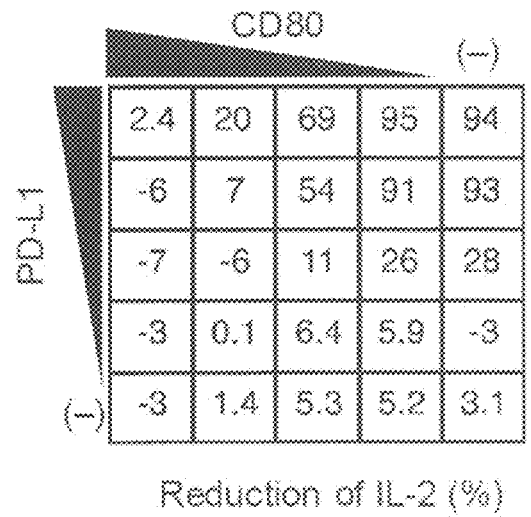
FIG. 8 shows the rate of inhibition of PD-1-mediated IL-2 production when IL-2 production from DO11.10 T cells was elicited by IIAdL1 cells expressing PD-L1 and CD80 at 25 different expression levels.

Next, the dose-dependent effects of the cis-PD-L1/CD80 interaction were investigated. CD80 and PD-L1 were expressed alone or simultaneously on IIAdL1 cells at four different expression levels (25 combinations in total) (FIG. 5). As expected, when a significant amount of CD80 was expressed at the same time as PD-L1, the binding of PD-1-EC to PD-L1 decreased in response to the expression level of CD80 (FIGS. 6 and 7). Antigen-presenting cells having PD-1-EC binding ability were able to elicit PD-1 function and suppress IL-2 production by activating DO11.10 T cells (FIG. 8). These results indicate that, depending on the relative amounts of PD-L1 and CD80, the ability of antigen-presenting cells to bind to PD-1 on T cells and elicit their function is determined.

Figure 9:
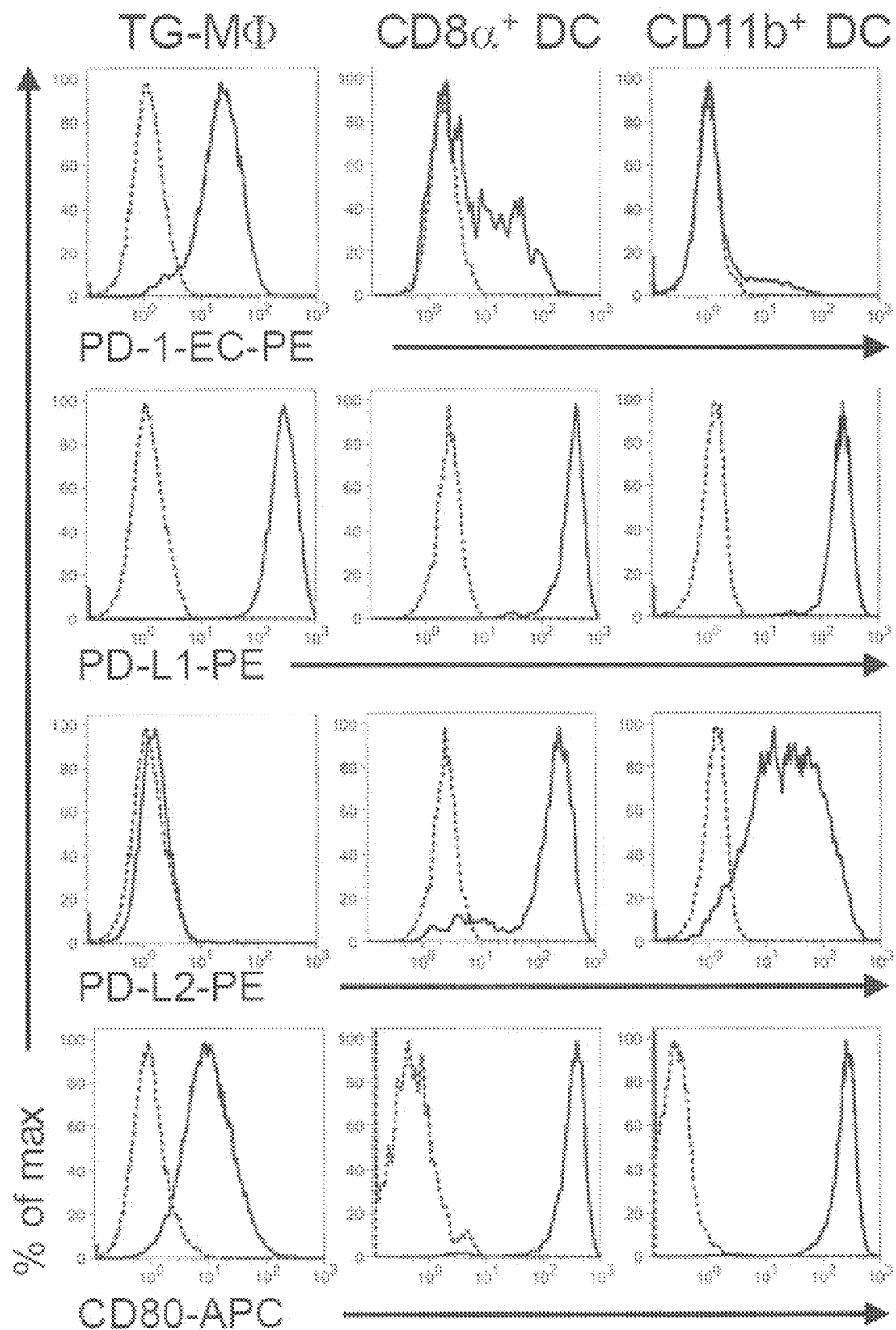
FIG. 9 shows the intensity of the binding of PD-1-EC and labeled antibodies shown in the drawing to LPS-activated splenic CD8α+, CD11b+DC, and TG-MΦ. The dashed histograms indicate isotype control staining.

Test 2: Interference with PD-1-Mediated Inhibition in T Cell Activation by Primary Culture DC Activated CD8$\alpha^+$ and CD11b$^+$ splenic DC as well as thioglycolate-induced peritoneal MΦ (TG-MΦ) were analyzed to investigate cis-PD-L1/CD80 interactions in vivo (FIG. 9). Interestingly, despite the common high PD-L1 expression levels (FIG. 9, second row), the PD-1-EC binding intensities of the three cell populations differed significantly: TO-MCD bound to PD-1-EC strongly; CD8$\alpha^+$DC bound to PD-1-EC weakly; and CD11b$^+$DC hardly bound to PD-1-EC (FIG. 9, top row). Notably, the expression levels of CD80 on CD8$\alpha^+$ and CD11b$^+$DC were much higher than the expression levels of CD80 on TG-MCD (FIG. 9, bottom row).

Figure 10:
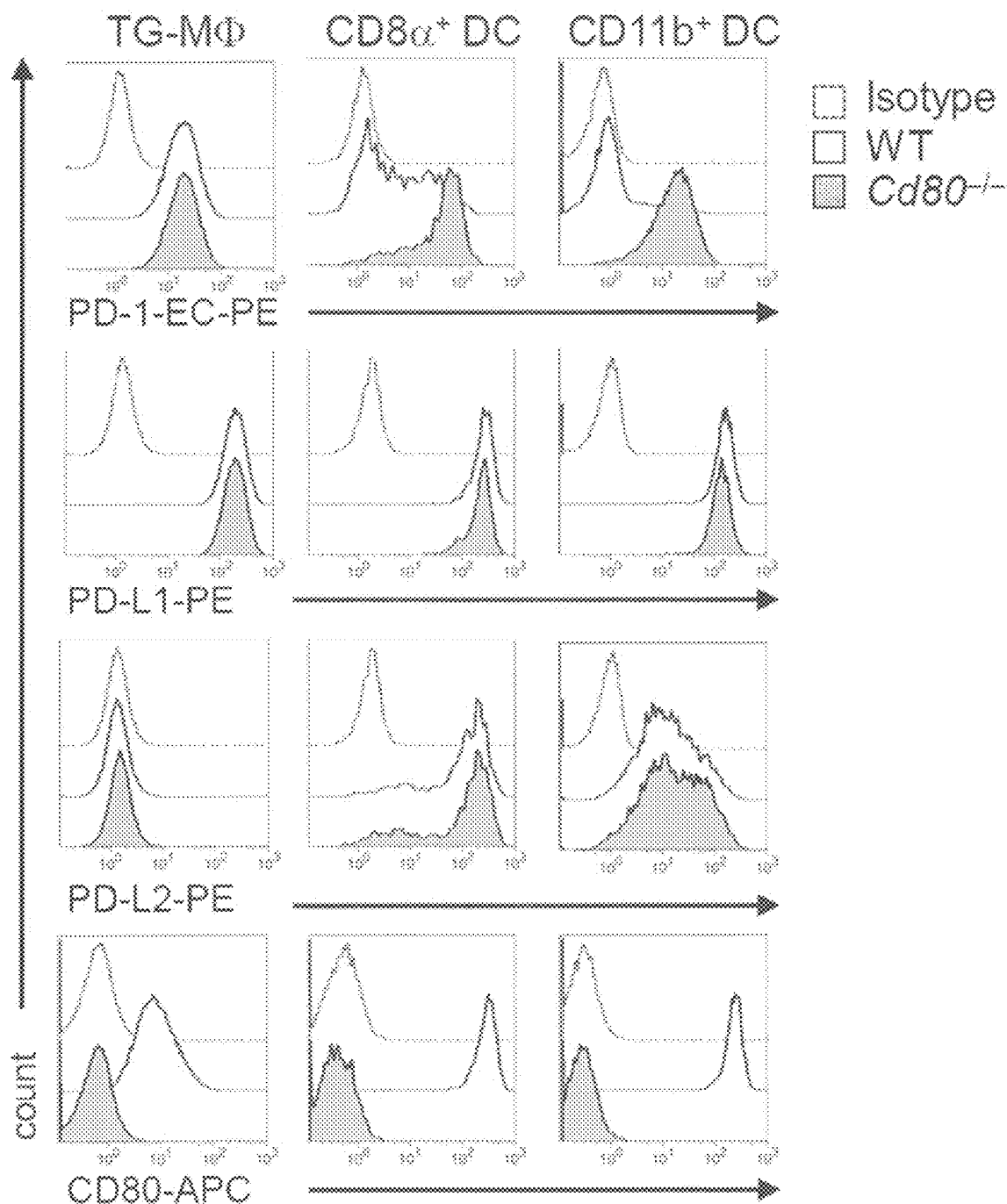
FIG. 10 shows the intensities of the binding of PD-1-EC and antibodies shown in the drawing to LPS-activated splenic CD8α+, CD11b+DC, and TG-MΦ derived from wild-type or C57BL/6-Cd80$^{-/-}$ mice.

Next, CD80 knockout (C57BL/6N-Cd80$^{-/-}$) mice were generated, and the same cell populations as those described above were analyzed (FIG. 10). Notably, C57BL/6N-Cd80$^{-/-}$ mouse-derived CD8$\alpha^+$ and CD11b$^+$DC bound to PD-1-EC with a strength similar to that of TG-MΦ (FIG. 10, top row). This result indicates that in wild-type mice, the bindings of CD8$\alpha^+$ and CD11b$^+$DC to PD-1-EC are incomplete due to strong CD80 expression. The expression levels of CD80 on TG-MCD derived from wild-type mice were not high enough to interfere with PD-L1/PD-1 binding, and the intensity of binding between TG-MCD and PD-1-EC was not changed by CD80 deficiency.

Figure 11:
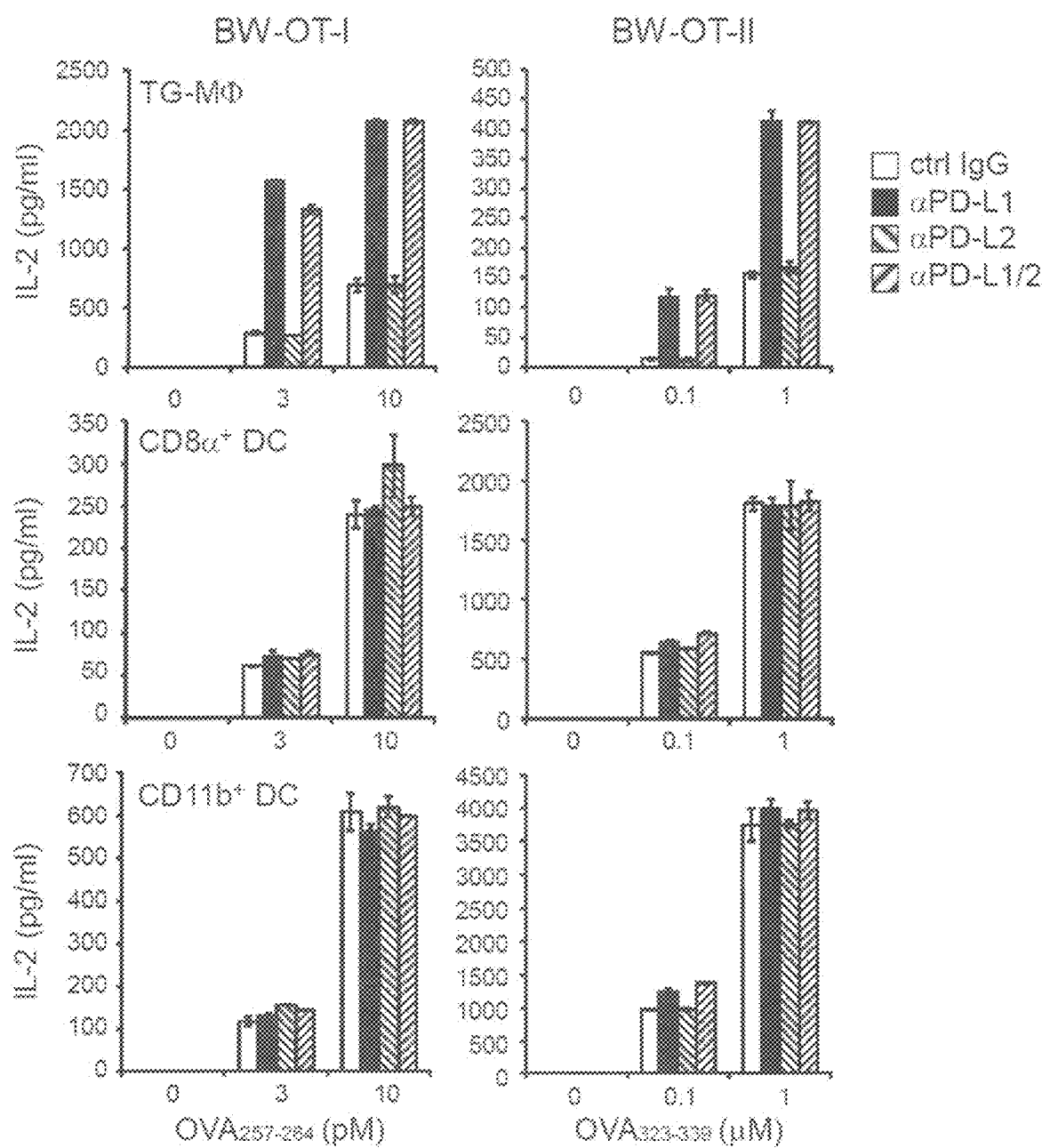
FIG. 11 shows IL-2 production from T cells when LPS-activated TG-MΦ (upper row), splenic CD8α+ (middle row), and CD11b+ (lower row) DC were pulsed with antigenic peptide in the amounts shown in the drawing, and BW-OT-I cells (left) and BW-OT-II cells (right) were stimulated by these cells. Function-inhibiting antibodies against PD-L1 and PD-L2 and isotype control IgG were added as shown in the drawing.
Figure 12:
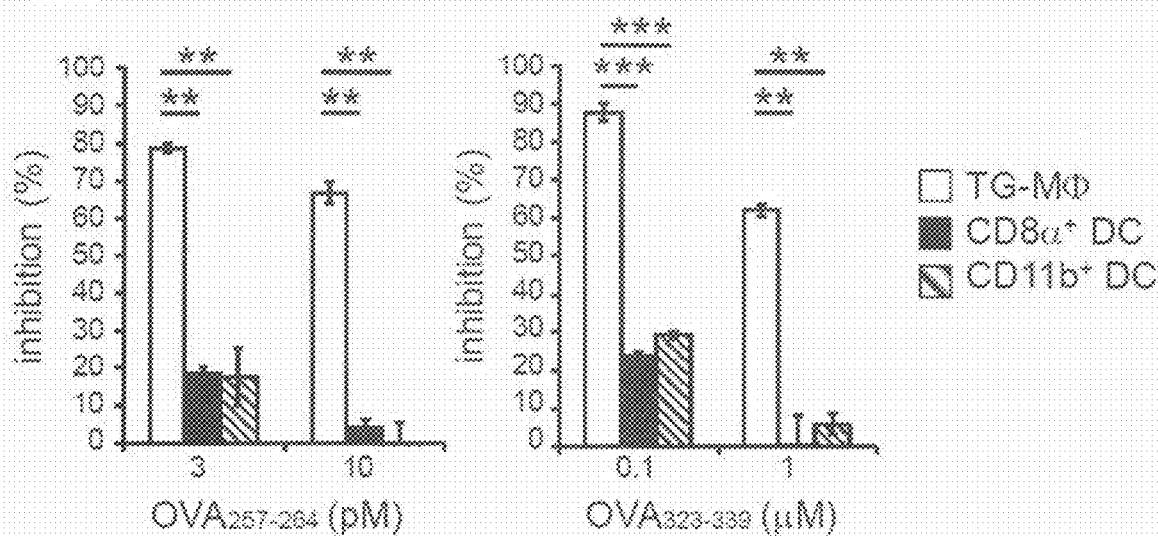
FIG. 12 shows the rate of PD-1 mediated inhibition of IL-2 production under the conditions shown in the drawing. One-way ANOVA with Dunnett's post-test. p<0.01; *p<0.001.

Next, by using CD8$\alpha^+$ and CD11b$^+$DC and TG-MCD were used as antigen-presenting cells, T lymphoma cells (BW-OT-I cells) that respond to pOVA$_{257-264}$/H2-K$^b$, or T lymphoma cells (BW-OT-II cells) that respond to pOVA$_{323-339}$/I-A$^b$ were stimulated (FIG. 11). In both BW-OT-I and BW-OT-II cells, TG-MCD elicited the inhibitory function of PD-1, in agreement with its strong PD-1-EC binding ability (FIG. 11, upper row). In contrast, CD8$\alpha^+$ and CD11b$^+$DC could not elicit PD-1-mediated inhibitory effects on the activation of BW-OT-I cells and BW-OT-II cells (FIG. 11, middle and lower). FIG. 12 shows the result of further analysis of the data shown in FIG. 11. These results indicate that in T cell activation by T-DC interaction, DC expresses a sufficient amount of CD80 to interfere with PD-L1/PD-1 binding, controlling PD-1 function.

Test 3: PD-L1 and CD80 Mutants without Cis-PD-L1/CD80 Interactions

Figure 13:
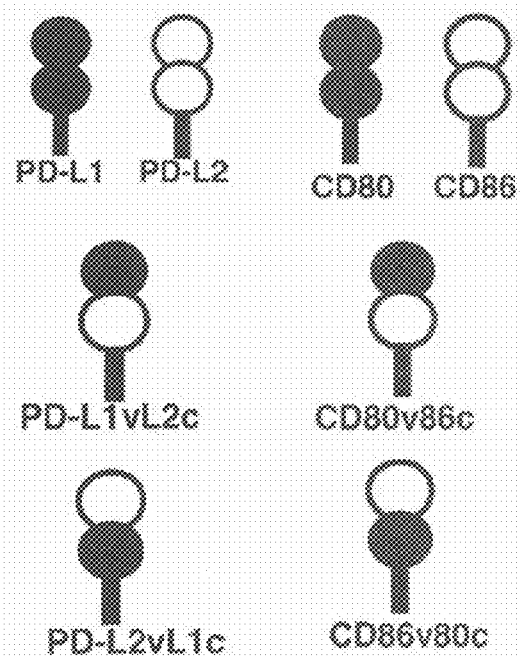
FIG. 13 schematically illustrates chimeric molecules of PD-L1, PD-L2, CD80 and CD86 in which the IgV and IgC domains have been swapped.
Figure 14:
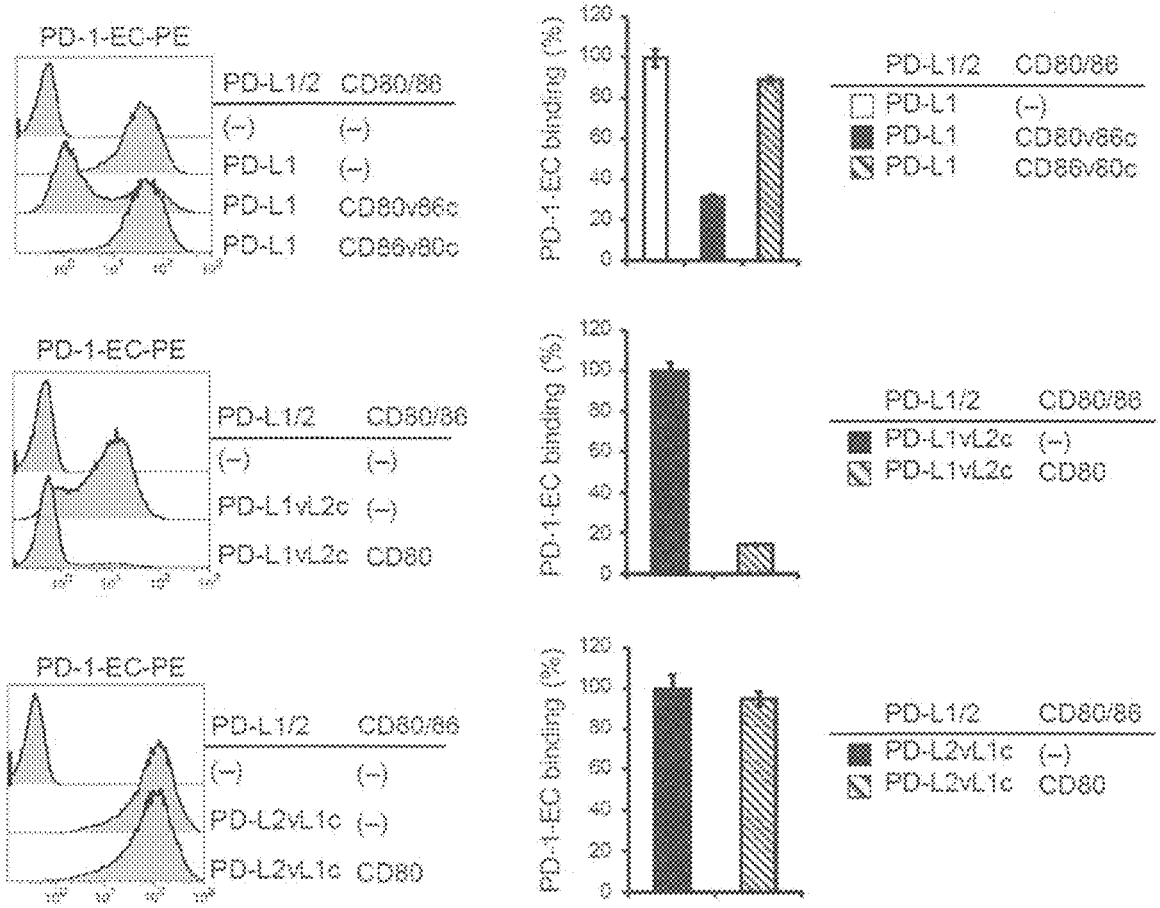
FIG. 14 shows the PD-1-EC binding intensities of IIAdL1 cells expressing the molecules shown in the drawing.
Figure 16:
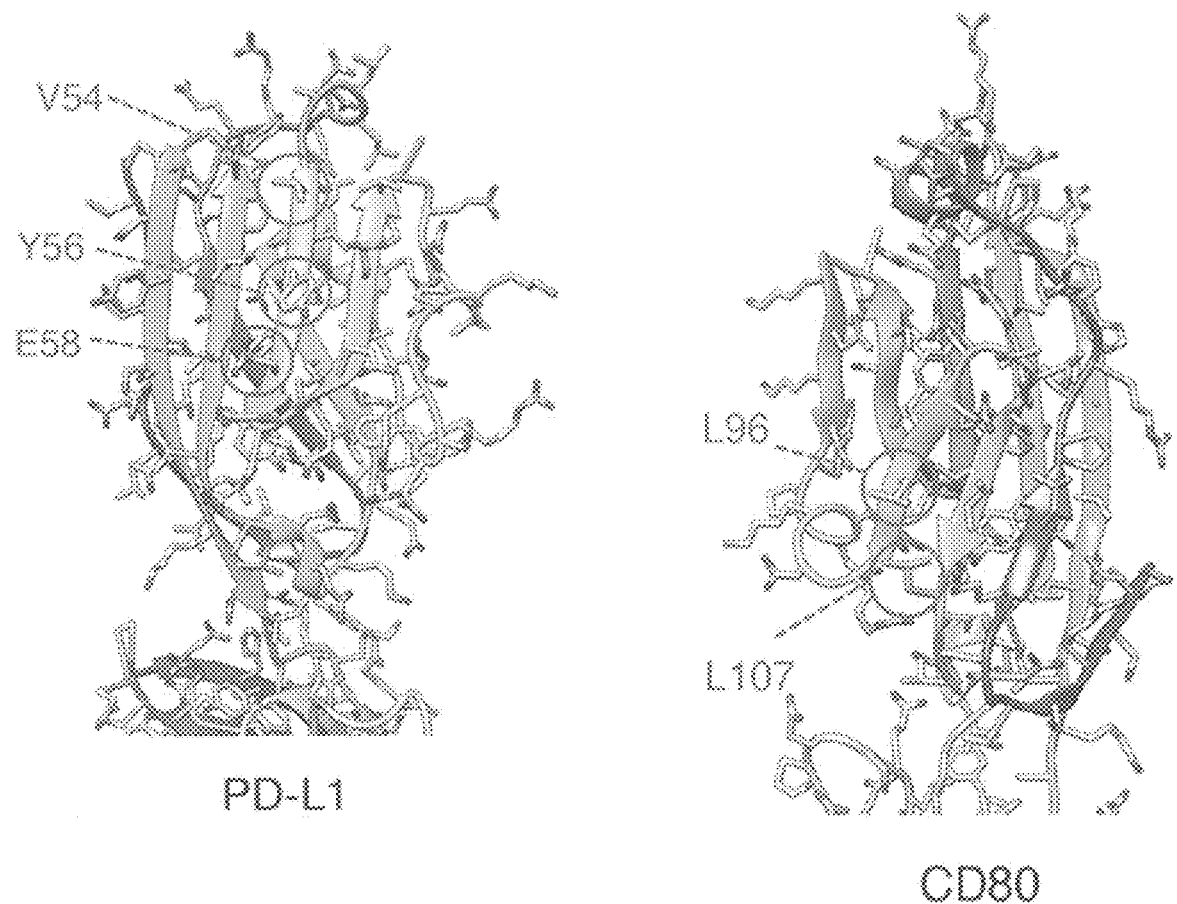
FIG. 16 shows the predicted 3D structures of mouse PD-L1 (left) and mouse CD80 (right). Amino acid residues that affect the cis-PD-L1/CD80 interaction are shown.

Attempts were made to isolate PD-L1 mutants that retain other functions but cannot bind to CD80, and CD80 mutants that cannot bind to PD-L1. By analyzing the binding characteristics of chimeric molecules of PD-L1, PD-L2, CD80, and CD86 in which the IgV and IgC domains were swapped, it was clarified that the IgV domains of PD-L1 and CD80 were involved in their interaction (FIGS. 13 and 14). Random mutations were introduced into the IgV domain of PD-L1 by using error prone PCR, these mutants were overexpressed in IIAdL1-CD80 cells, and cells that acquired PD-1-EC binding ability were separated by cell sorting. I took it. PD-L1 mutants isolated from these cells had high mutation rates at V54, Y56, and E58 (FIG. 15, top row). The predicted three-dimensional (3D) structure of mouse PD-L1 indicated that these amino acid residues were located in the C strand of PD-L1. This C chain is close to the PD-1-interacting surface (Lin, D. Y.-W. Et al. Proc. Natl. Acad. Sci. U.S.A. 105, 3011-6 (2008)) (FIG. 16, left). These results suggest that the PD-L1/CD80 interaction surface partially overlaps the PD-L1/PD–1 interaction surface.

Figure 17:
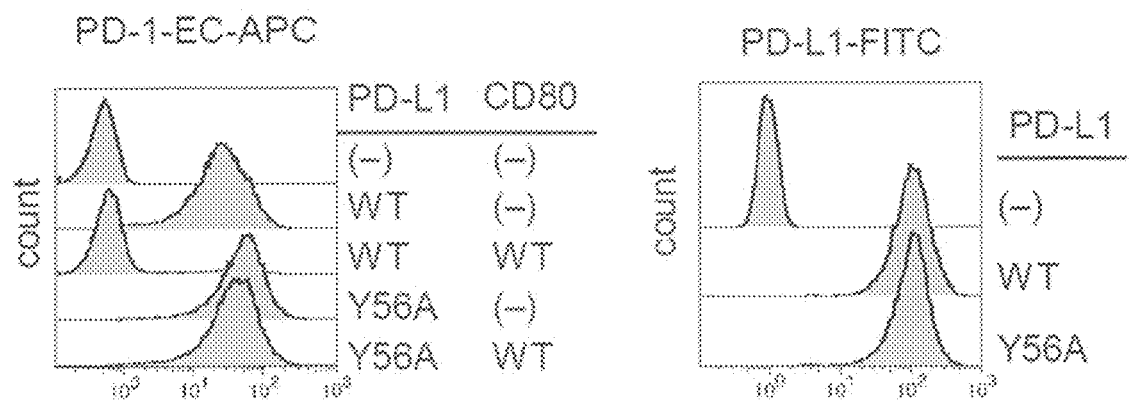
FIG. 17 shows the binding of PD-1-EC to PD-L1Y56A in the presence of CD80. The intensities of the binding of PD-1-EC (left) and anti-PD-L1 antibody (right) to IIAdL1 cells expressing the molecule shown in the drawing is shown.

By examining a series of point mutants at Y56 (FIG. 15, lower), PD-L1Y56A was used for subsequent analyses because this Y56A mutant bound to PD-1-EC comparably in the presence or absence of CD80 (FIG. 17, left) and was expressed in IIAdL1 cells at similar levels to wild-type PD-L1 (FIG. 17, right).

Figure 18:
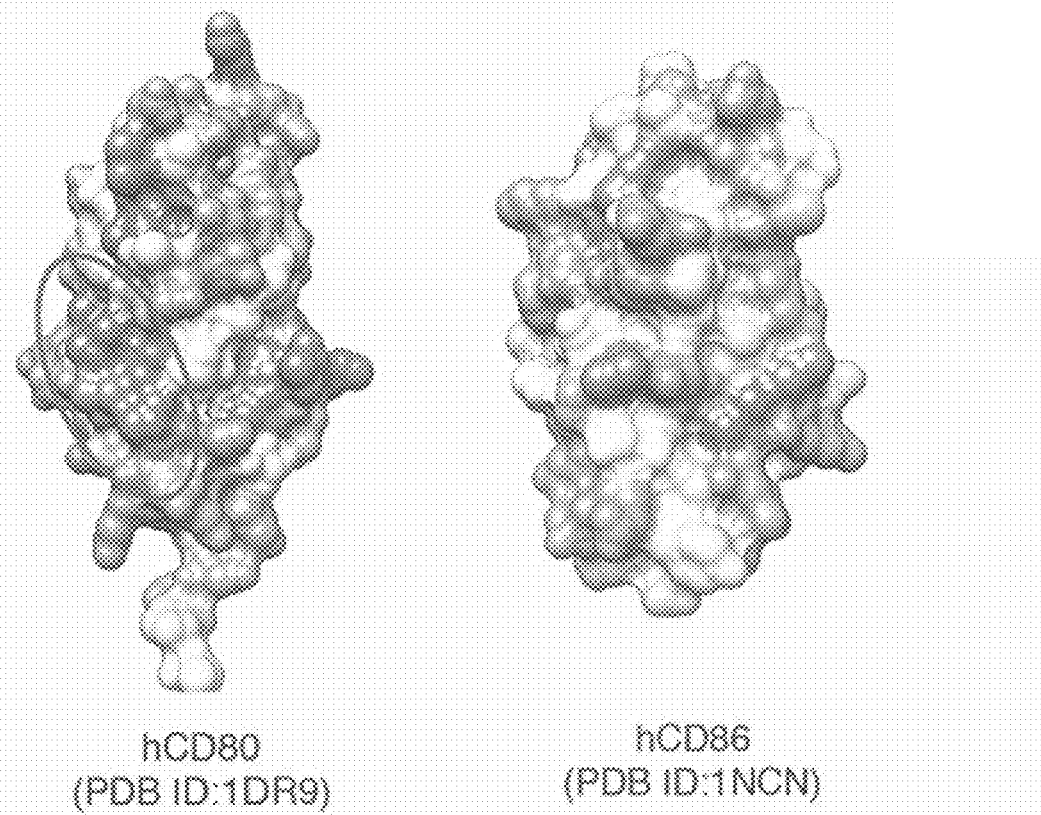
FIG. 18 shows the hydrophobicity (gray) of human CD80 (left) and CD86 (right). The hydrophobicity of these molecules was analyzed with the UCSF Chimera Software. In the drawing, the circled area shows the unique hydrophobic patch found on the DEB surface of CD80.
Figure 19:
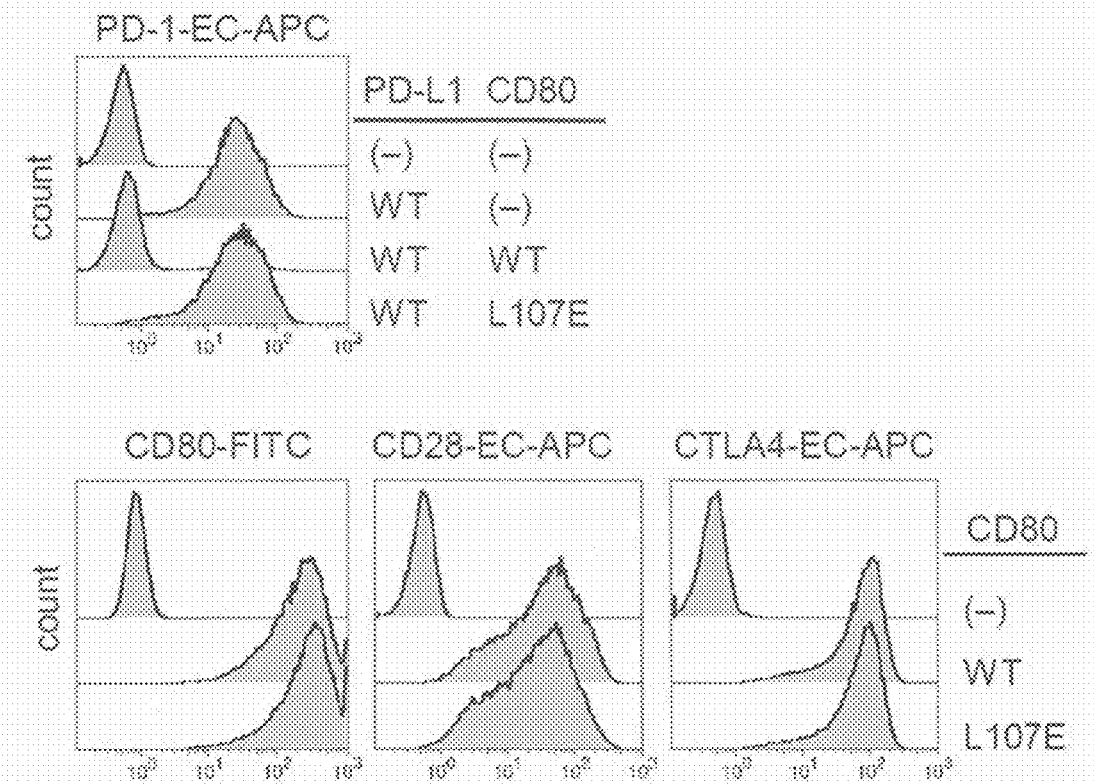
FIG. 19 shows the binding of PD-1-EC to PD-L1 in the presence of CD80L107E. The intensities of the binding of PD-1-EC, anti-CD80 antibody, CD28-EC, and CTLA-4-EC to IIAdL1 cells expressing the molecule shown in the drawing are shown.
Figure 20:
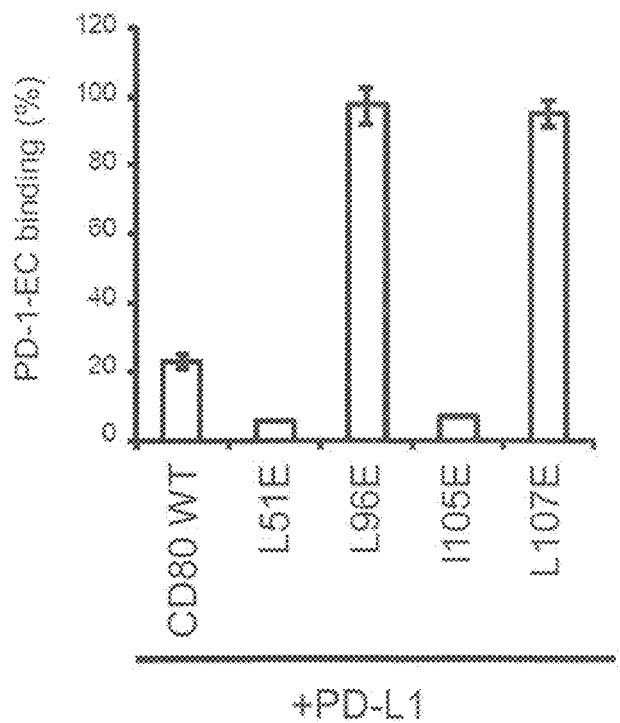
FIG. 20 shows the PD-1-EC binding abilities of IIAdL1-PD-L1 cells expressing CD80 in which hydrophobic residues in the hydrophobic patch are replaced with amino acids. The PD-1-EC binding intensities of cells are shown in comparison with the PD-1-EC binding intensities of IIAdL1-PD-L1 cells that do not have CD80.
Figure 21:
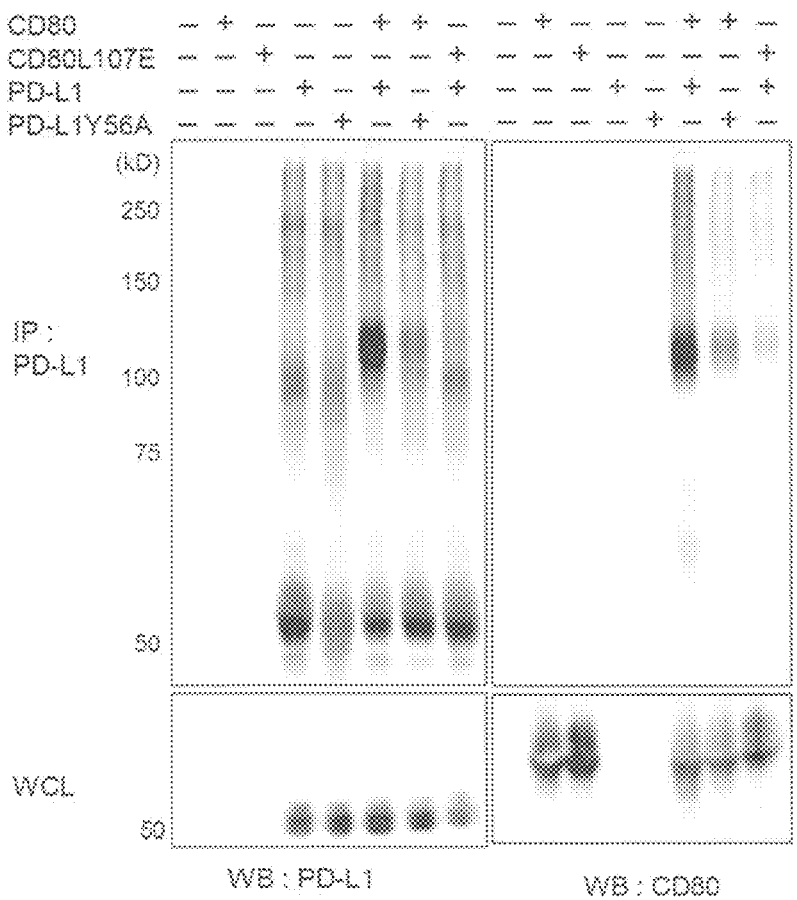
FIG. 21 shows the lack of co-immunoprecipitation of PD-L1Y56A/CD80 and PD-L1/CD80L107E. WCL: whole uncrosslinked cell lysate.

Because CD28 binds to the AGFCC'C" face of CD80 (Ikemizu, S. et al., Immunity 12, 51-60(2000); Stamper, C. C. et al. Nature 410, 608-11(2001); Evans, E. J. et al. Nat. Immunol. 6, 271-279(2005)) and CD80 can bind CD28 in the presence of PD-L1 (data not shown), the DEB face of CD80 was focused. By comparing the hydrophobicities of CD80 (Ikemizu, S. et al., Already mentioned) and CD86 (Zhang, X., Schwartz, J.-C. D., Almo, S. C. & Nathenson, S. G., Proc. Natl. Acad. Sci. U.S.A. 100, 2586-91 (2003)), a distinctive hydrophobic patch in the DEB face of CD80 was found (FIG. 18). Then, amino acid residues in this hydrophobic patch were mutated. CD80 with either the L96E or L107E mutation failed to interfere with PD-L1/PD-1 binding (FIG. 19, upper row, and FIG. 20). CD80L107E mutant did not interfere with PD-L1/PD-1 binding, bound to CD28 and CTLA-4 at the levels comparable to that of wild-type CD80, and showed expression levels in IIAdL1 cells similar to those of wild-type CD80 (FIG. 19). Therefore, CD80L107E was used for the subsequent analysis. In addition, co-immunoprecipitations of CD80 with PD-L1 Y56A were severely attenuated, and coimmunoprecipitations of CD80L107E with CD80 were nearly abolished (FIG. 21).

Figure 22:
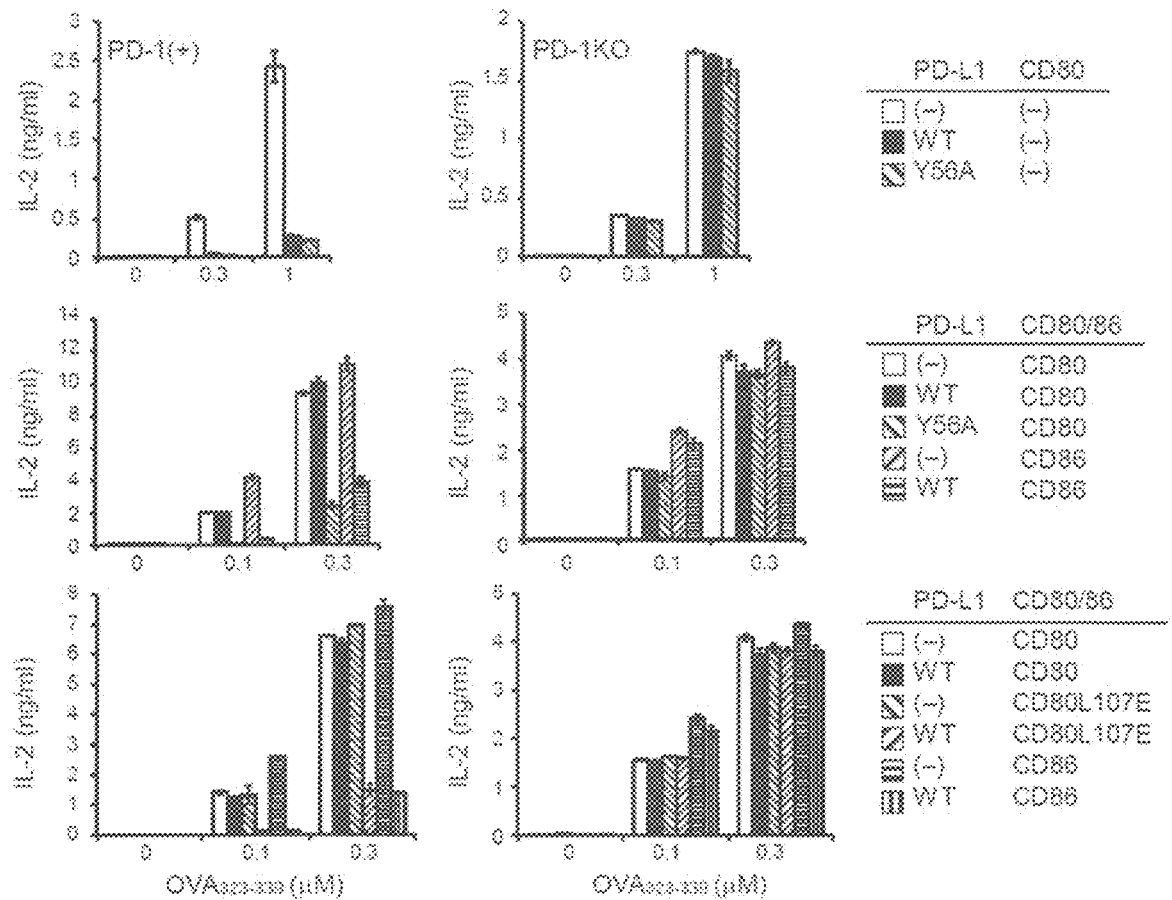
FIG. 22 shows IL-2 production from T cells when antigen-presenting cells expressing the molecules shown in the drawing were co-cultured with PD-1-expressing DO11.10 T cells (PD-1 (+)) (left) or PD-1-deficient DO11.10T cells (PD-1KO) (right). Antigen peptide in the amounts in the drawing was used.
Figure 23:
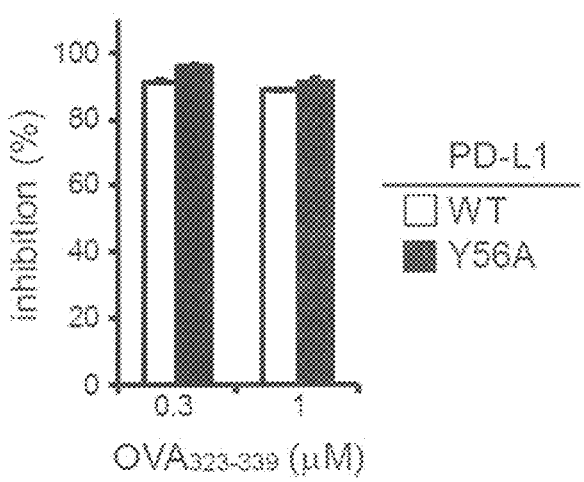
FIG. 23 shows the results of further analysis of the data shown in the upper row of FIG. 22. The rates of PD-1-dependent inhibition mediated by PD-L1 and PDL1Y56A are shown.

Next, the function of these mutants was tested. When IIAdL1 cells expressing PD-L1Y56A were used as antigen-presenting cells to stimulate DO11.10 T cells, PD-L1Y56A elicited PD-1-mediated inhibitory effects at levels comparable to those of wild-type PD-L1 in the absence of CD80 (FIG. 22, upper row, and FIG. 23). In addition, PD-L1 Y56A elicited the PD-1 function even in the presence of CD80 (FIG. 22, middle row, and FIG. 24). This result indicates that PD-L1Y56A can evade the inhibitory effect of CD80 and elicit PD-1 activity. When CD80L107E was expressed on IIAdL1 cells in the absence of PD-L1, CD80L107E enhanced IL-2 production from DO11.10 T cells by antigen stimulation to the same extent as wild-type CD80. Furthermore, PD-L1 triggered PD-1 functions in the presence of CD80L107E (FIG. 22, lower row, and FIG. 24). This result indicates that CD80L107E cannot inhibit PD-L1 from eliciting the PD-1 function.

Figure 27:
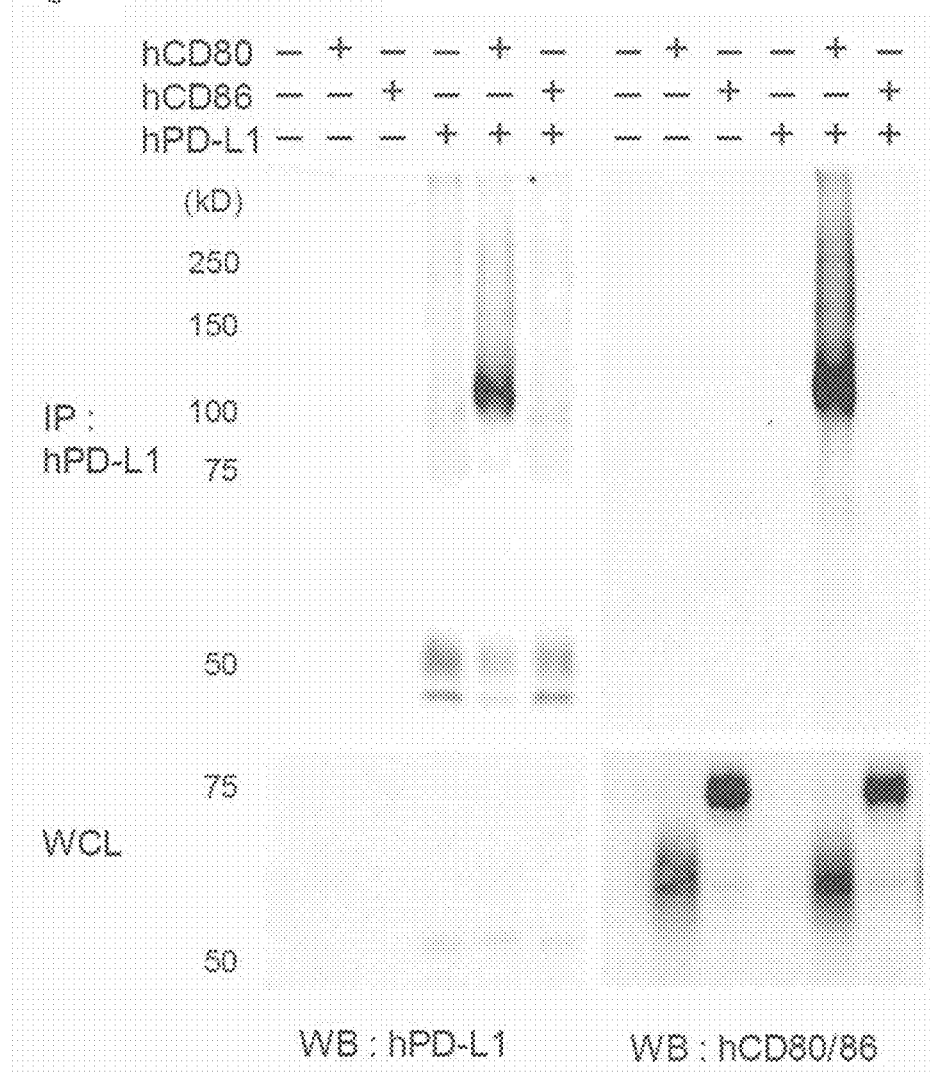
FIG. 27 shows co-immunoprecipitation of human CD80 and human PD-L1 in IIAdL1 cells. WCL: whole uncrosslinked cell lysate.
Figure 28:
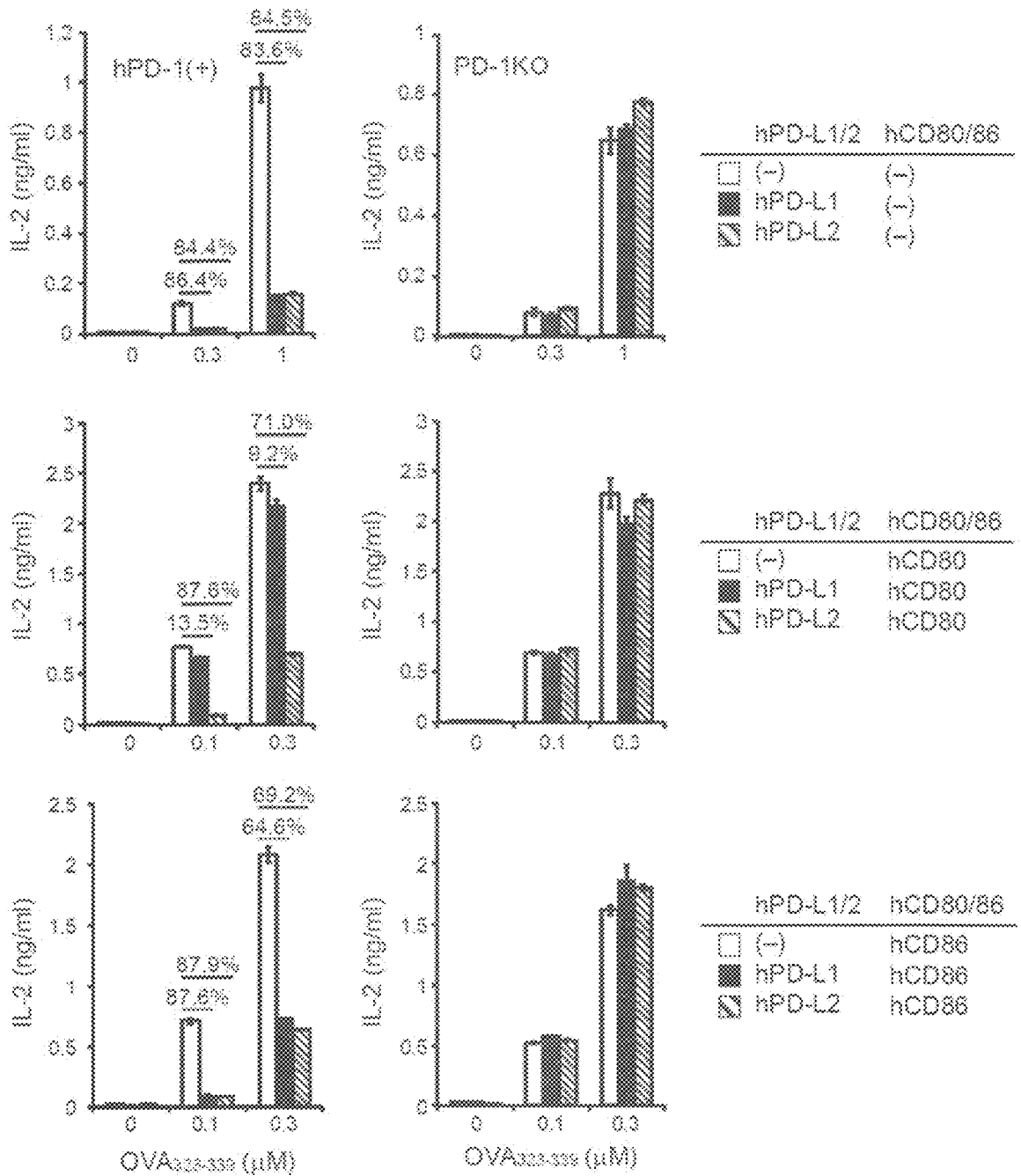
FIG. 28 shows IL-2 production from T cells when antigen-presenting cells shown in the drawing were pulsed with antigen peptide in the amounts shown in the drawing, and were co-cultured with DO11.10 T cells including human PD-1 (hPD-1 (+)) (left) or not including the same (PD-1KO) (right). The rates of human PD-1-mediated inhibition of IL-2 production are shown in the drawing.
Figure 30:
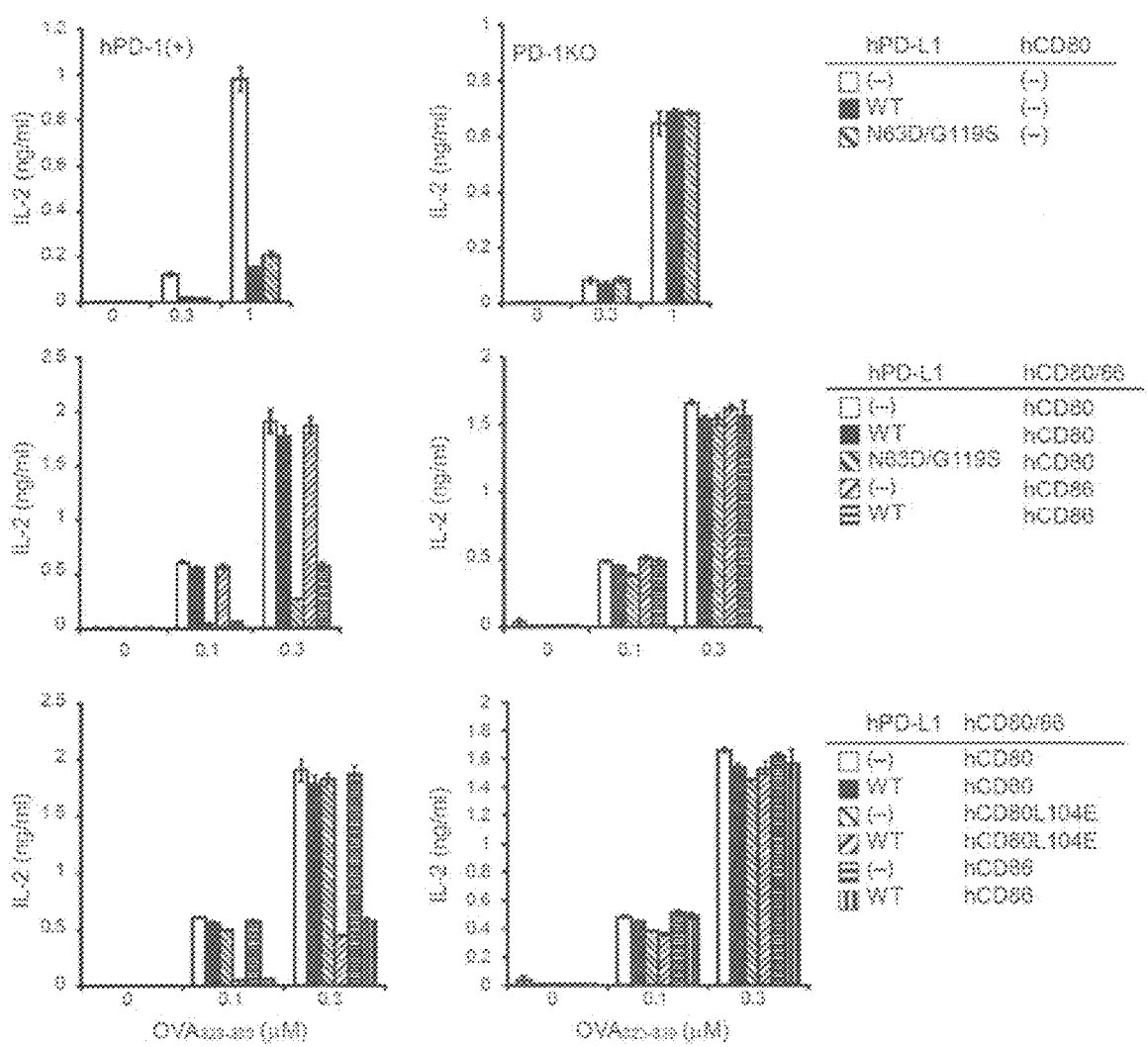
FIG. 30 shows IL-2 production from T cells when antigen-presenting cells expressing the molecules shown in the drawing were co-cultured with human PD-1-expressing (hPD-1 (+)) (left) or PD-1-deficient (PD-1KO) (right) DO11.10T cells. Antigen peptide in the amounts in the drawing was used.

Test 4: Attenuation of PD-1 Mediated Inhibition by Cis-PD-L1/CD80 Interaction in Humans A similar experiment was performed using human orthologs to investigate whether the PD-1 mediated inhibitory effect was also attenuated by the cis-PD-L1/CD80 interaction in humans. Similarly to mouse molecules, human CD80 bound to human PD-L1 and attenuated the binding of human PD-L1 to human PD-1, but these did not occur to human CD86 (FIGS. 25 and 26). Human CD80 was co-immunoprecipitated with human PD-L1, but human CD86 was not (FIG. 27). Furthermore, the cis interaction between human CD80 and human PD-L1 inhibited human PD-L1 from eliciting the inhibitory function of PD-1 (FIG. 28). We have also succeeded in isolating human CD80 mutants and human PD-L1 mutants lacking cis-PD-L1/CD80 interactions and unable to control the PD-1 function (FIGS. 29 and 30). Human PD-L1N63D/G119S mutant elicited PD-1-mediated inhibition at a level comparably to that of wild-type human PD-L1 in the absence of human CD80 (FIG. 30, upper row), and elicited PD-1-mediated inhibition even in the presence of human CD80 (FIG. 30, middle row). In addition, the human CD80L104E mutant was unable to prevent PD-L1 from eliciting PD-1-mediated inhibition (FIG. 30, lower row).

Figure 31:
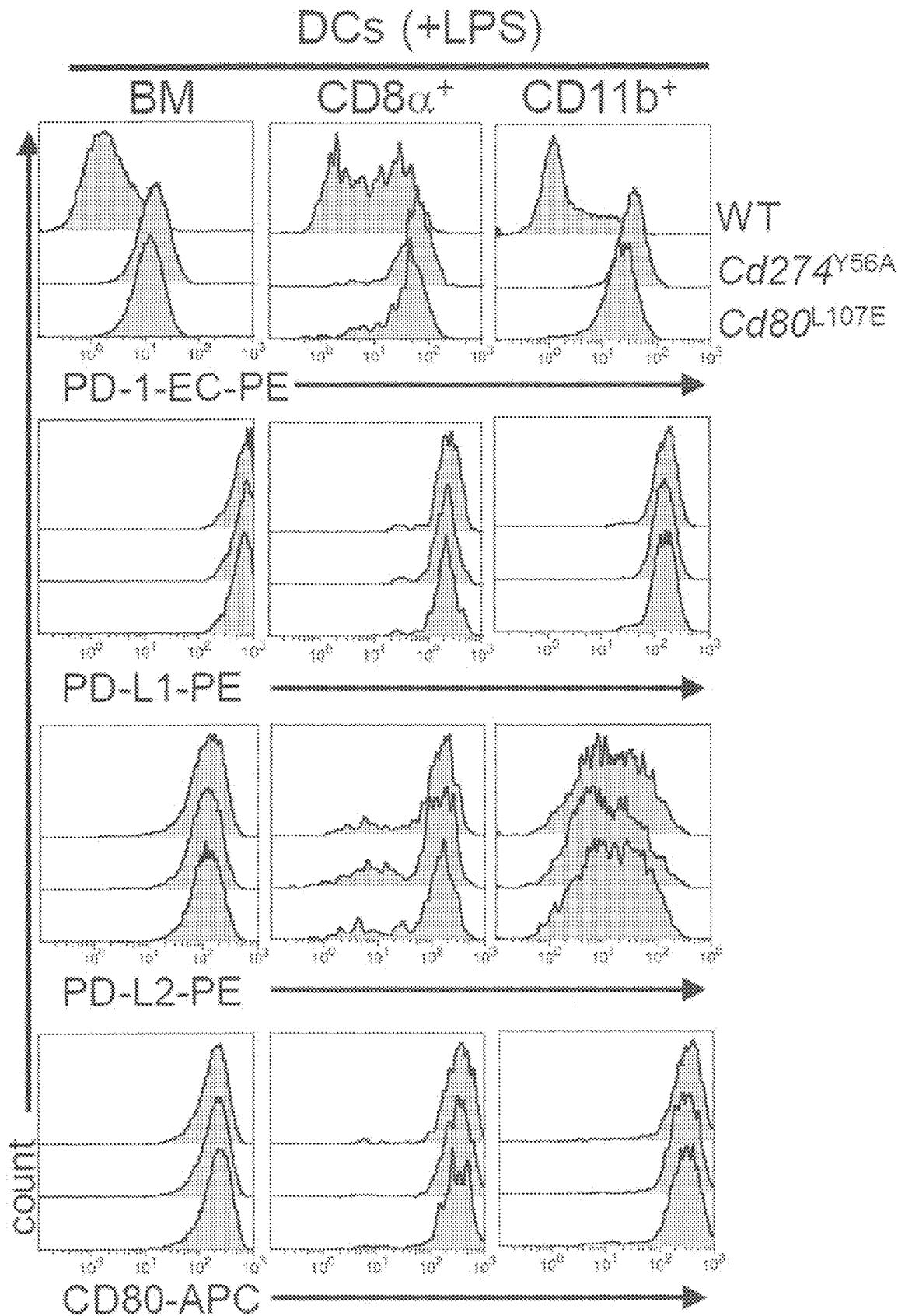
FIG. 31 shows PD-1-EC binding intensities, as well as expression levels of PD-L1, PD-L2, and CD80 in LPS-activated BM-DC, splenic CD8α+, and CD11b+DC derived from C57BL/6N-Cd80$^{L107E}$ mice and C57BL/6N-Cd274$^{Y56A}$ mice.
Figure 32:
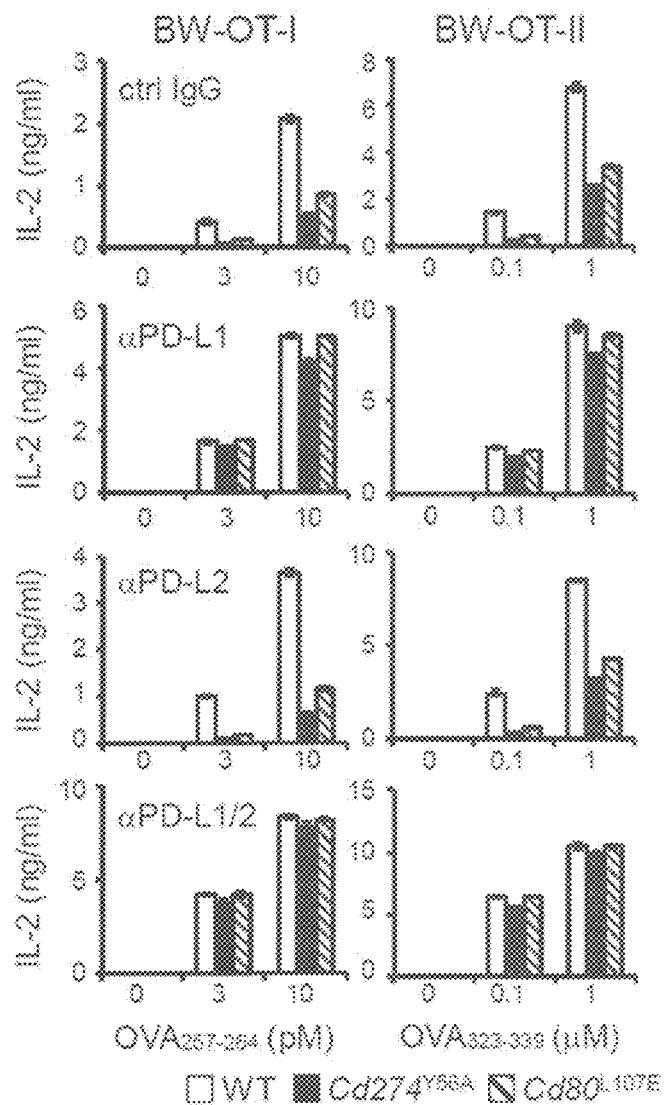
FIG. 32 shows concentrations of IL-2, which indicate PD-1-mediated inhibition of IL-2 production in BW-OT-I cells (left) and BW-OT-II cells (right) stimulated by BM-DC derived from C57BL/6N-Cd80$^{L107E}$ and C57BL/6N-Cd274$^{Y56A}$ mice.
Figure 33:
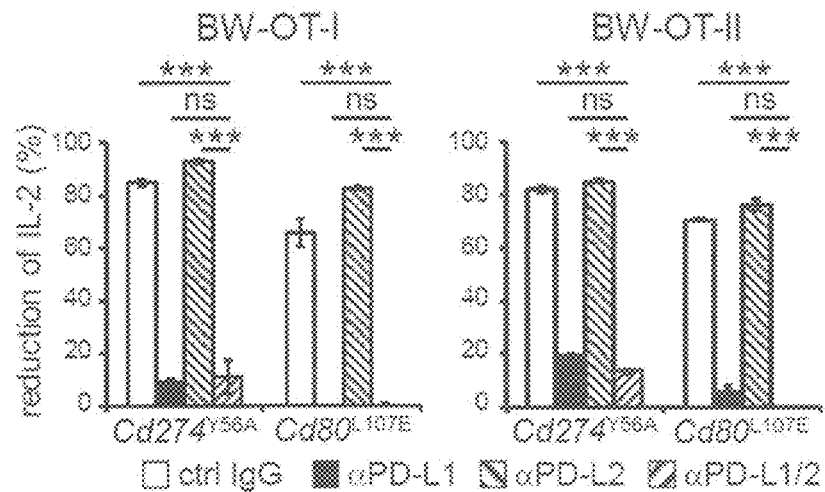
FIG. 33 shows relative values indicating the results of FIG. 32. Data on antigen concentration of 3 pM for BW-OT-I cells and data on antigen concentration of 0.1 μM for BW-OT-II cells were used. One-way ANOVA with Dunnett's post-test. ***p<0.001.
Figure 34:
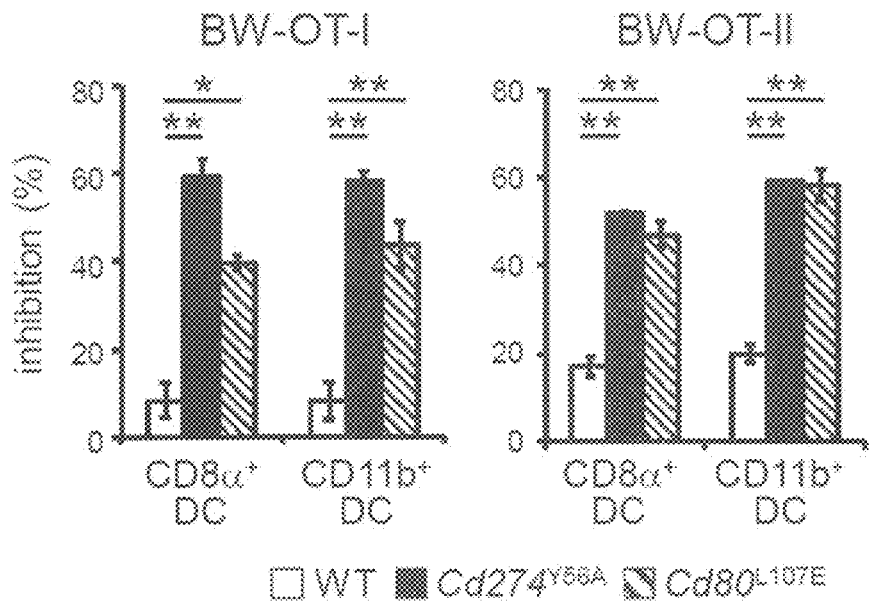
FIG. 34 shows PD-1-mediated inhibition of IL-2 production in BW-OT-I cells (left) and BW-OT-II cells (right) stimulated by splenic CD8α+, and CD11b+DC derived from C57BL/6N-Cd80$^{L107E}$ mice and C57BL/6N-Cd274$^{Y56A}$ mice. One-way ANOVA with Dunnett's post-test. *p<0.05; **p<0.01.

Test 5: Attenuation of T Cell Response to Immunogenicity, Tumor Cells and Autologous Tissue in the Absence of Cis-PD-L1/CD80 Interaction To investigate the biological significance of cis-PD-L1/CD80 interactions in vivo, knock-in mice of PD-L1Y56A and CD80L107E were generated using the CRISPR/Cas9 system (C57BL/6N-Cd274$^{Y56A}$ mice and C57BL/6N-Cd80$^{L107E}$ mice). The C57BL/6N-Cd274$^{Y56A}$ mice and the C57BL/6N-Cd80$^{L107E}$ mice were born normally, without any apparent impairment, and grew healthy. Activated CD8α$^+$DC and CD11b$^+$DC, and granulocyte-macrophage colony-stimulating factor (GM-CSF)-induced bone marrow-derived dendritic cells (BM-DCs) from knock-in mice showed much stronger PD-1-EC-binding ability compared to those from wild-type mice, despite similar expression levels for CD80, PD-L1, and PD-L2 (FIG. 31). The expression levels of CD86 and MHC II on these cells were also comparable. Activated DCs from wild-type mice elicited little inhibitory effect of PD-1 on BW-OT-I and BW-OT-II cell activation, but activated DCs from C57BL/6N-Cd274$^{Y56A}$ mice and C57BL/6N-Cd80$^{L107E}$ mice elicited inhibitory effects (FIGS. 32 to 34).

Figure 35:
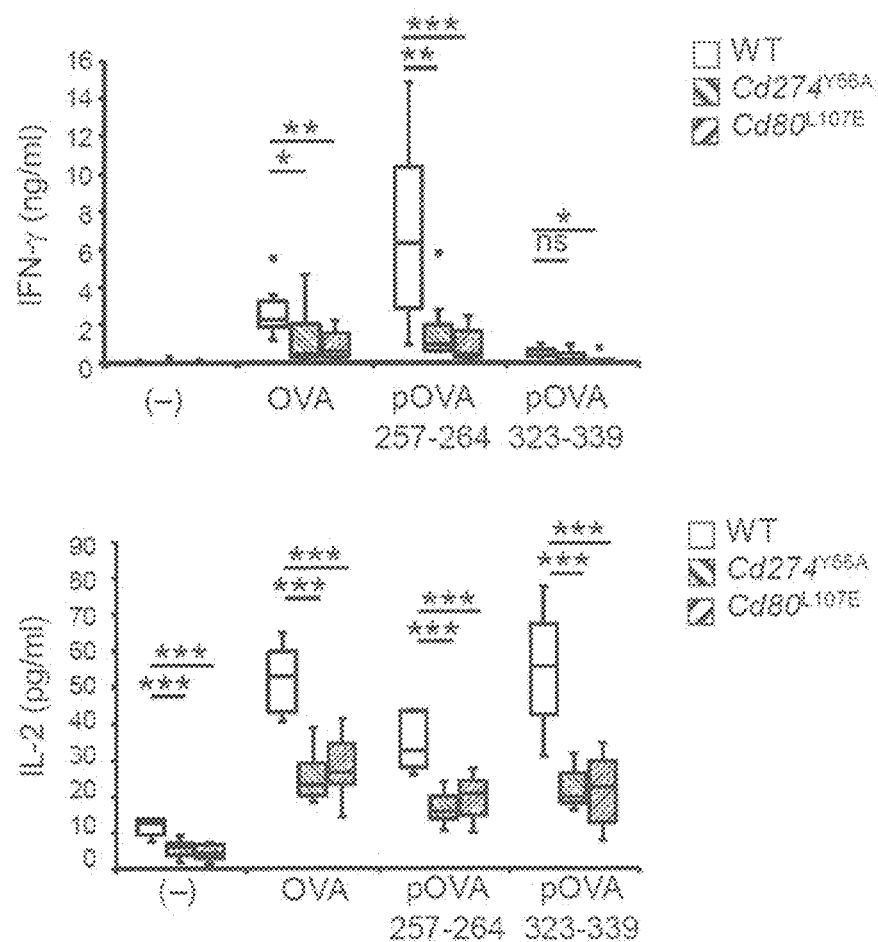
FIG. 35 shows that OVA-specific T cells capable of producing IFN-γ (upper) and IL-2 (lower) were not induced in immunoinduction experiments in the absence of cis-PD-L1/CD80 interaction (n=9). One-way ANOVA with Dunnett's post-test. *p<0.05; p<0.01; *p<0.001.

Next, the effect of the cis-PD-L1/CD80 interaction on the immune response against foreign antigens in vivo was investigated. C57BL/6N-Cd274$^{Y56A}$ and C57BL/6N-Cd80$^{L107E}$ mice were inoculated with OVA protein emulsified in Freund's complete adjuvant (CFA) as an antigen, and T cells in regional lymph nodes were restimulated one week later. IFN-γ, production and IL-2 production from T cells, upon stimulation with OVA protein and MHC I- and MHC II-restricted OVA peptides, was significantly reduced in both knock-in mice compared to those in wild-type mice (FIG. 35). These results indicate that PD-1 function is controlled in wild-type mice by cis-PD-L1/CD80 interactions during the induction of immune responses against foreign antigens.

Figure 36:
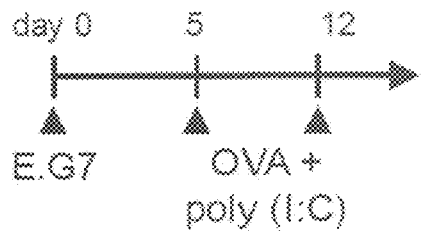
FIG. 36 shows an experimental design of vaccination with OVA and poly(I:C).
Figure 37:
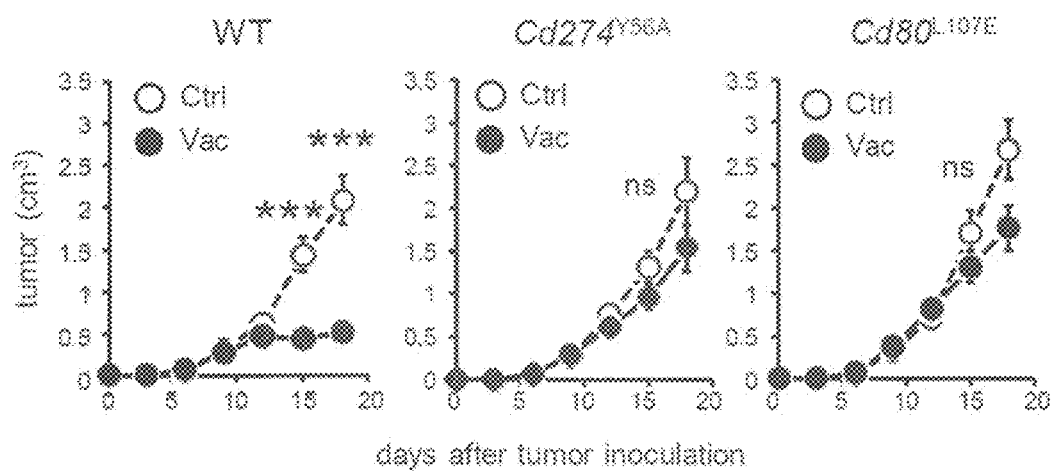
FIG. 37 shows volumes of E.G7 tumors in wild-type, Cd80$^{L107E}$, and Cd274$^{Y56A}$ mice immunized with PBS (Ctrl) or OVA and poly(I:C) (Vac). Unpaired student's two-sided t-test. ***p<0.001.
Figure 38:
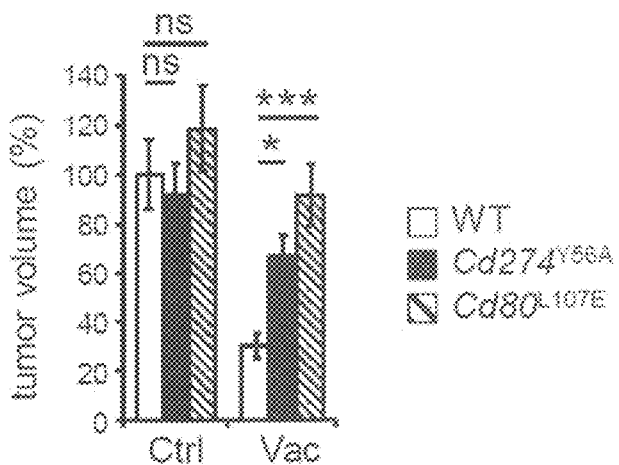
FIG. 38 shows relative volumes of E.G7 tumors (day 15) in wild-type, Cd80$^{L107E}$, and Cd274$^{Y56A}$ mice immunized with PBS (Ctrl) or OVA and poly(I:C) (Vac). Shown (n≥8). One-way ANOVA with Dunnett's post-test. *p<0.05; ***p<0.001.
Figure 39:
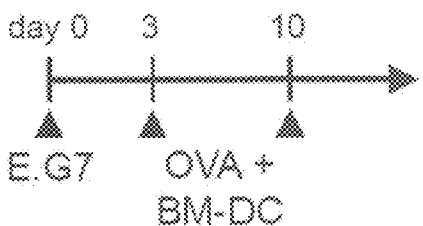
FIG. 39 shows an experimental design of vaccination with OVA-pulsed BM-DC.
Figure 40:
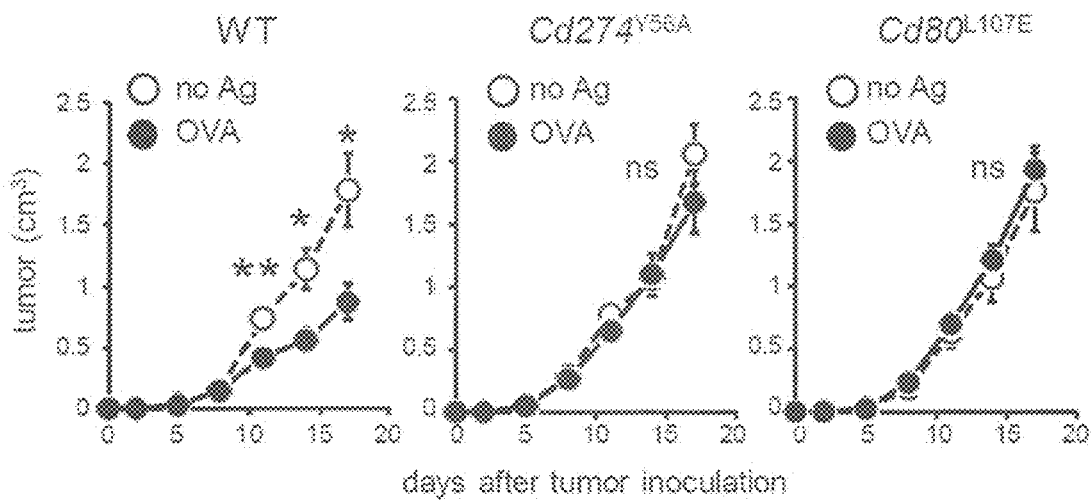
FIG. 40 shows volumes of E.G7 tumors in wild-type mice immunized with BM-DCs derived from wild-type, Cd274$^{Y56A}$, and Cd80$^{L107E}$ mice. Unpaired student's two-sided t-test. *p<0.05; **p<0.01.
Figure 41:
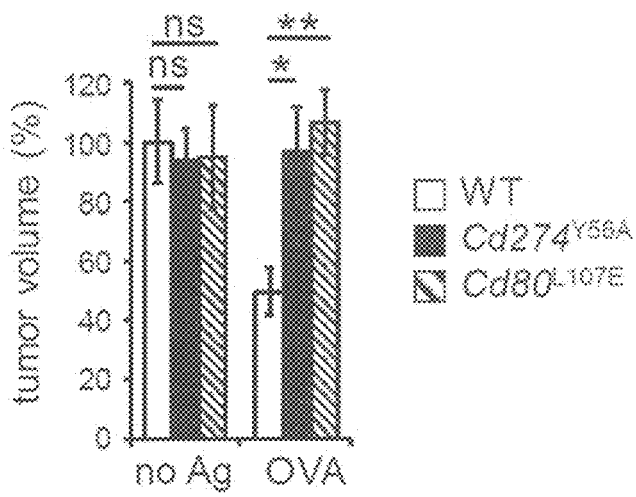
FIG. 41 shows relative volumes (day 14) of E.G7 tumors in wild-type mice immunized with BM-DCs derived from wild-type, Cd274$^{Y56A}$, and Cd80$^{L107E}$ mice (n=7). One-way ANOVA with Dunnett's post-test. *p<0.05; **p<0.01.

Next, the involvement of cis-PD-L1/CD80 interactions in cancer immunotherapy was tested. Mice were inoculated with E.G7 lymphoma cells that express OVA (Moore, M. W., Carbone, F. R. & Bevan, M. J., Cell 54, 777-85(1988)), and were vaccinated with OVA protein together with poly(I:C) (FIG. 36). Tumor growth was substantially suppressed by vaccination in wild-type mice, whereas significant curative effects were not observed in C57BL/6N-Cd274$^{Y56A}$ and C57BL/6N-Cd80$^{L107E}$ mice (FIGS. 37 and 38). In addition, dendritic cell vaccines were used to directly examine the role of cis-PD-L1/CD80 interactions on antigen-presenting cells. Wild-type mice inoculated with E.G7 cells were administered with OVA-pulsed BM-DCs from wild-type mice and knock-in mice, and an immune response was induced (FIG. 39). Consistent with the effects of protein vaccination, dendritic cell vaccine therapy with wild-type mouse-derived BM-DC induced a strong anti-tumor immune response, but the immunization with BM-DCs from C57BL/6N-Cd274$^{Y56A}$ mice and C57BL/6N-Cd80$^{L107E}$ did not induce an antitumor immune responses (FIGS. 40 and 41). These results indicate that the control of PD-1 function by the cis-PD-L1/CD80 interactions is very important for the induction of anti-tumor immune responses.

Figure 42:
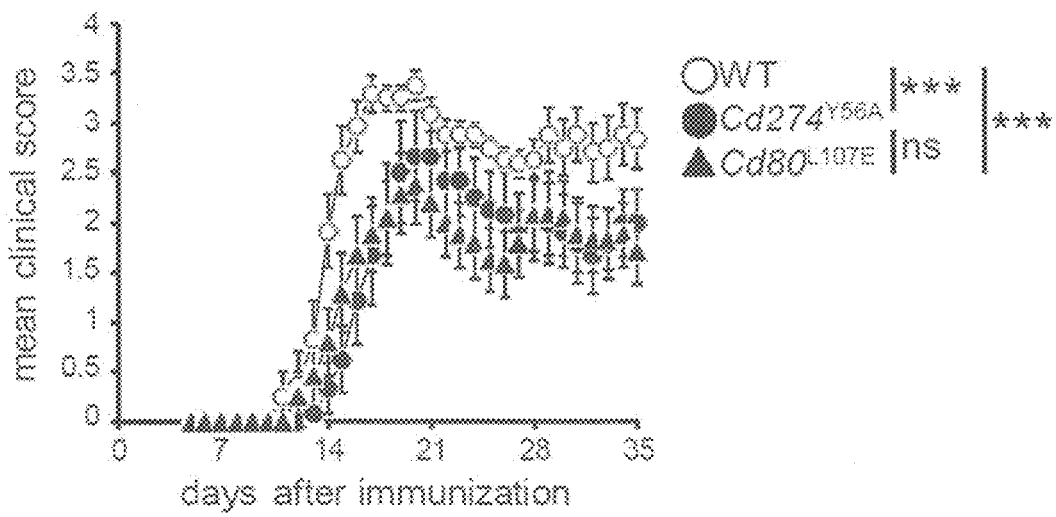
FIG. 42 shows clinical scores of experimental autoimmune encephalomyelitis (EAE) in wild-type, Cd274$^{Y56A}$, and Cd80$^{L107E}$ mice (n=12). Two-way repeated measures ANOVA with Tukey HSD post-test. ***p<0.001.

Furthermore, the role of the cis-PD-L1/CD80 interaction in autoimmunity was investigated using experimental autoimmune encephalomyelitis (EAE), which is a mouse model of multiple sclerosis. C57BL/6N-Cd274$^{Y56A}$ and C57BL/6N-Cd80$^{L107E}$ mice showed significantly reduced symptoms of EAE caused by immunoinduction induced by MOG peptide as an antigen compared to those in wild-type mice (FIG. 42). Similarly, upon restimulation with the MOG peptide, IL-17 production from splenic cells from C57BL/

Figure 43:
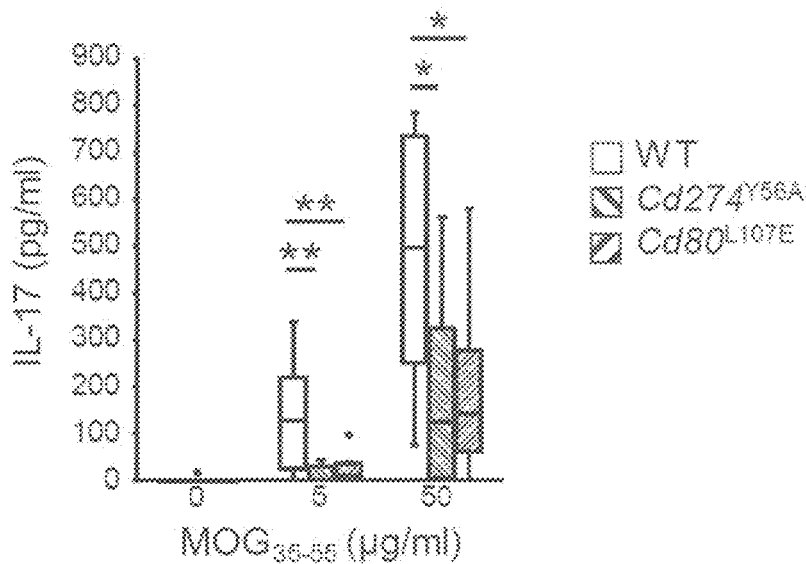
FIG. 43 shows that IL-17-producing cells were not induced during EAE induction in the absence of cis-PD-L1/CD80 interaction (n=8). One-way ANOVA with Dunnett's post-test. *p<0.05; **p<0.01.

6N-Cd274$^{Y56A}$ nice and C57BL/6N-Cd80$^{L107E}$ mice immunized with the MOG peptide was significantly lower (FIG. 43). These findings indicate that PD-1 inhibitory effects were hampered by cis-PD-L1/CD80 interactions in wild-type mice at the onset of EAE, whereas PD-L1, liberated from CD80 in C57BL/6N-Cd274$^{Y56A}$ mice and C57BL/6N-Cd80$^{L107E}$ mice, binds to PD-1 and exerts inhibitory effects, thereby alleviating the symptoms of EAE.

Tests with Anti-CD80 Antibody

Materials and Methods

Soluble Protein

A cDNA fragment encoding the extracellular region of mouse CD80 was amplified by PCR and fused with the Fc region of human IgG1 (hIgG1Fc). Chimeric cDNA was cloned into an expression vector modified from pEFBOS-neo. The plasmid was transfected into Plat-E cells using Avalanche-Omni Transfection Reagent (EZ Biosystems), and the culture supernatant was collected after 48 hours. Mouse CD80-hIgG1Fc was purified with protein G (GE Healthcare).

Mouse

C57BL/6N-Cd80$^{-/-}$ mice were bred in an environmentally controlled clean room under specific pathogen-free conditions. All mouse protocols have been approved by the Institutional Animal Care and Use Committee (IACUC) of Tokushima University Generation of Anti-Mouse CD80 Monoclonal Antibody (mAb)

C57BL/6N-Cd80$^{-/-}$ mouse lymph node cells inoculated with mouse CD80-hIgG1Fc protein as an antigen to induce an immune response were fused with SP2/o cells by electric cell fusion (LF301, BEX). The culture supernatants of hybridoma clones were tested for their ability to dissociate cis-PD-L1/CD80 interactions.

Generation of Anti-Human CD80 mAb

BALB/c mouse lymph node cells inoculated with human CD80-hIgG1Fc protein (R&D Systems) as an antigen to induce an immune response were fused with SP2/o cells using Sendai virus coat (GenomONE-CF, Ishihara Sangyo Kaisha). The culture supernatants of hybridoma clones were tested for their ability to dissociate cis-PD-L1/CD80 interactions.

Stimulation of DO11.10 T Cells and TCR-Reconstructed Cells

DO11.10 T cells (5×10$^4$ cells/well) were stimulated for 12-14 hours with IIAdL1 cells (1×10$^4$ cells/well) pulsed with OVA323-339 peptide (ISQAVHAAHAEINEAGR, >95% purity, Sigma-Aldrich Japan or eurofins genomics) in the amounts shown in the drawing. 5 µg/ml anti-mouse CD80 antibody (TKMG48, 1G10 (BD bioscience), RM80 (Biorad)), mouse IgG1 isotype control (MOPC-21, Biolegend), anti-human CD80 antibody (TKMF5), and mouse IgG2a isotype control (MOPC-173, Biolegend) were added as described below. The concentrations of IL-2 in the culture supernatants were measured by ELISA (Biolegend).

EAE

Mice were immunized by subcutaneous inoculation of MOG$_{35-55}$ peptide (200 µg, MEVGWYRSPFSRVVH-LYRNGK, >95% purity, Eurofins) emulsified with Freund's incomplete adjuvant (BD Biosciences) containing *M. tuberculosis* H37RA (200 µg, BD Biosciences) (Day 0). Pertussis toxin (200 ng, List Biological Laboratories) was intraperitoneally administered on days 0 and 2. As shown in FIGS. 47 and 48, 500 µg of anti-mouse CD80 antibody (TKMG48) or isotype control mouse IgG1 (MOPC21, Bio X cell) was intraperitoneally administered. Clinical scores were evaluated in blind every day as follows: 0, no clinical signs; 1, dragging; 2, hindlimb weakness; 3, hindlimb paralysis; 4, hindlimb and forelimb paralysis; 5, moribund state.

Antibody Binding to CD80 Molecule

Respective bindings of TKMG48 and 16-10A1 to DOdKO cells transfected with mouse CD80, chimeric molecules in which the IgV and IgC domains of CD80 and CD86 were swapped (see FIG. 13), or mouse CD80 mutant lacking the binding ability to mouse PD-L1 (having L96E and/or L107E mutation) were evaluated by flow cytometry. The bindings of TKMF5 and 2D10 to DOdKO cells introduced with human CD80 or human CD80 mutants (having I92E and L104E mutations) lacking the ability to bind to human PD-L1 were evaluated by flow cytometry.

Evaluation of Binding of Anti-Mouse CD80 Antibody (TKMG48) and Anti-Human CD80 Antibody (TKMF5)

The binding affinity of the anti-mouse CD80 antibody (TKMG48) against the mouse CD80-soluble protein and the binding affinity of the anti-human CD80 antibody (TKMF5) against the human CD80-soluble protein were measured by biolayer interferometry. Briefly, a cDNA fragments encoding the extracellular region of mouse or human CD80 was amplified by PCR. A strep tag was added to the C-terminus of CD80. The chimeric cDNA was cloned into an expression vector modified from pEBMulti-Neo (Wako). Plat-E cells were transfected with the plasmid using Avalanche-Omni Transfection Reagent (EZ Biosystems) and the culture supernatant was collected after 48 hours. Monomeric CD80 (strep-tagged) was immobilized on a streptavidin-coated biosensor chip (Pall ForteBio) and binding of anti-CD80 antibodies at various concentrations was monitored with BLItz (Pall ForteBio). The chips were washed with PBS and the dissociation rates were analyzed. The binding rate constant (ka), the dissociation rate constant (kd), and the dissociation constant (KD) were calculated with BLItz Pro software.

[Result]

Immunosuppression by Anti-CD80 Antibody

Figure 44:
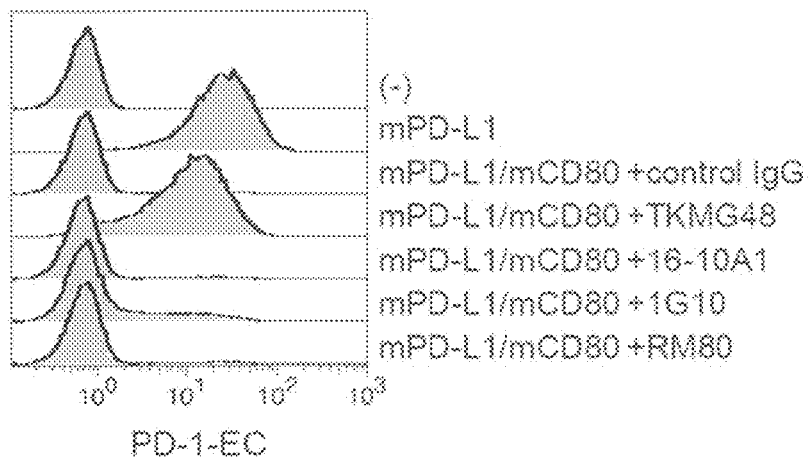
FIG. 44 shows that the anti-mouse CD80 antibody TKMG48 separated mPD-L1 and mCD80, and restored mPD-1 binding ability of mPD-L1.

Investigation was made on whether anti-mouse CD80 antibodies could allow mouse PD-1-EC to bind to mouse PD-L1 when mouse CD80 and mouse PD-L1 were present on the same antigen-presenting cells. PD-1 and PD-L1 gene-deficient DO11.10 T cells (DOdKO cells) were transfected with mouse PD-L1 and CD80 to obtain DOdKO-mPD-L1/mCD80 cells. DOdKO-mPD-L1/mCD80 cells were pretreated with 10 µg/ml of each anti-mouse CD80 antibody for 20 minutes at 37° C., followed by staining with mouse PD-1-EC. Mouse PD-1-EC bound to DOdKO-mPD-L1/mCD80 cells pretreated with TKMG48, but did not bind in cases where pretreated with other antibodies (FIG. 44). The effect of the TKMG48 pretreatment was evaluated by the following formula using the binding mean fluorescence intensity of mouse PD-1-EC.

(TKMG48 treated group−control group)/(control IgG group−control group)

The amount of binding of mouse PD-1-EC to DOdKO-mPD-L1/mCD80 cells pretreated with TKMG48 was about 10.1 times that of pretreated with control IgG. These results show that TKMG48 binds mouse PD-1-EC to mouse PD-L1 when mouse CD80 and mouse PD-L1 are present on the same antigen-presenting cells.

Figure 45:
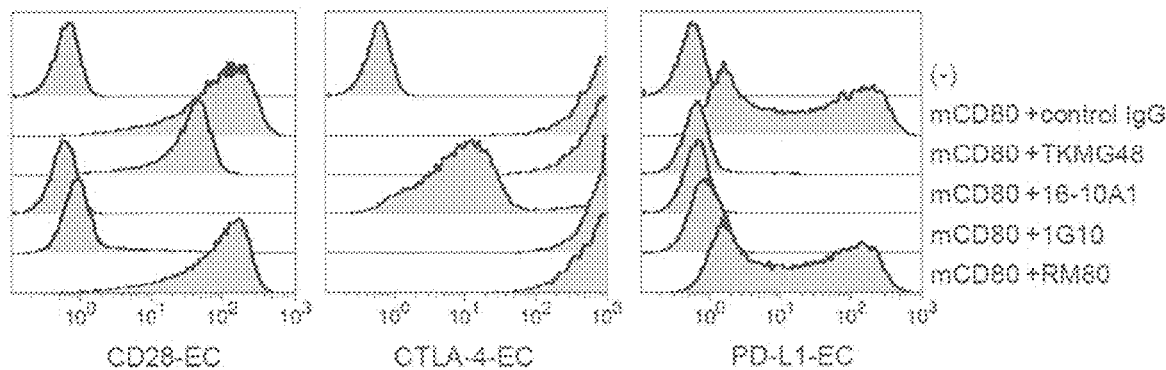
FIG. 45 shows that the anti-mouse CD80 antibody TKMG48 did not inhibit the binding of mCD80 to mCTLA-4 but weakly inhibited the binding of mCD80 to mCD28.

Investigation was made on the effects of anti-mouse CD80 antibodies on the interactions between CD80 and CD28, CD80 and CTLA-4, and CD80 and PD-L1. DOdKO-CD80 cells were pretreated with each anti-mouse CD80 antibody shown in FIG. 45 at 10 µg/ml for 20 minutes at 4° C., followed by staining with mouse CD28-EC, CTLA-4-EC or PD-L1-EC. The results are shown in FIG. 45. TKMG48 strongly inhibited the binding of PD-L1-EC to CD80. The binding of CD28-EC to CD80 was weakly inhibited by TKMG48, but the binding of CTLA-4-EC to CD80 was not inhibited by TKMG48. 16-10A1 strongly inhibited the interactions between CD80 and CD28-EC and between CD80 and PD-L1-EC, and partially inhibited the interaction between CD80 and CTLA-4-EC. 1G10 strongly inhibited the interactions between CD80 and CD28-EC and between CD80 and PD-L1-EC, but did not inhibit the interaction between CD80 and CTLA-4-EC. RM80 did not inhibit the binding of CD28-EC, CTLA-4-EC, and PD-L1-EC to CD80.

Figure 46:
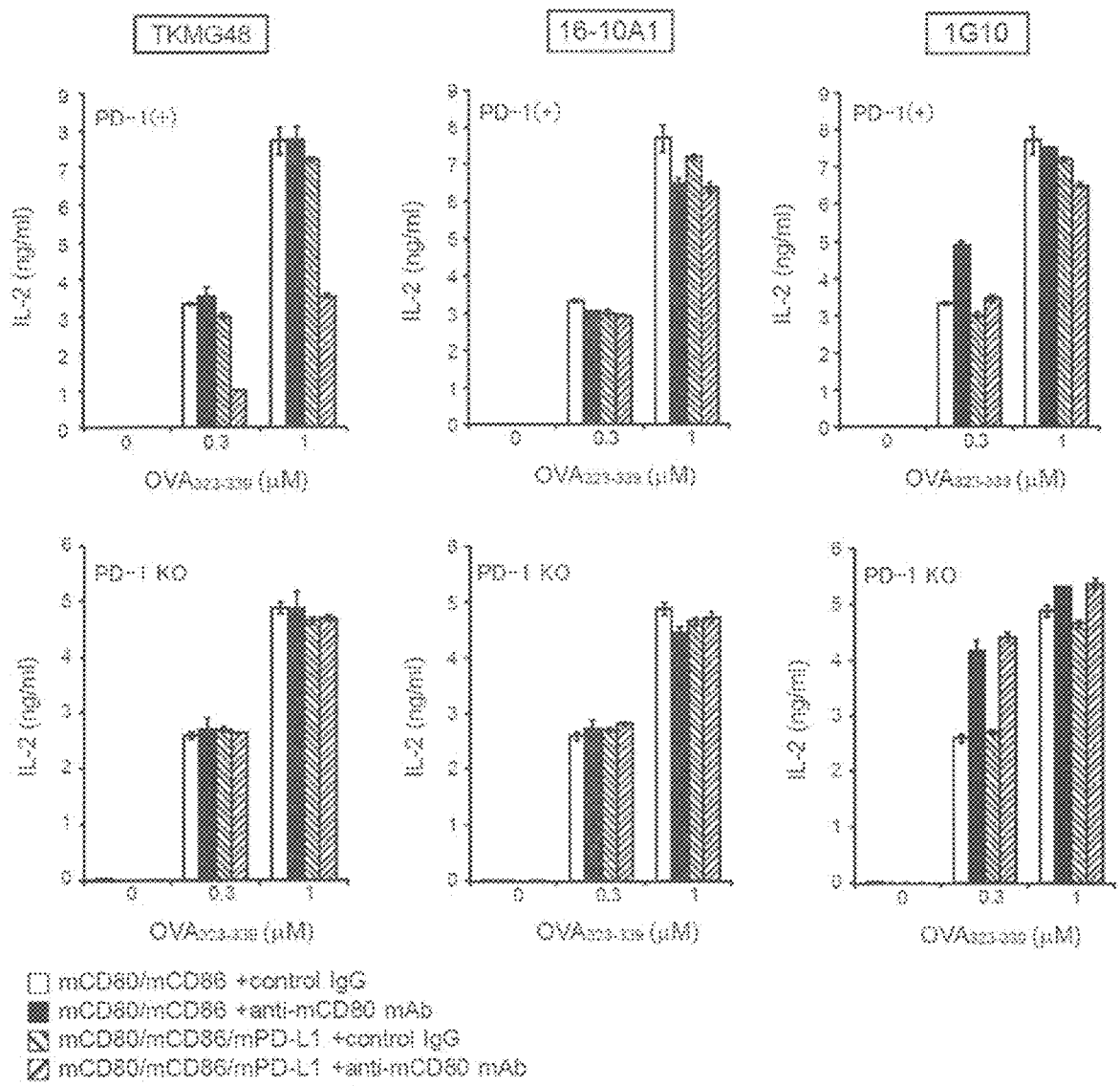
FIG. 46 shows that the addition of the anti-mouse CD80 antibody TKMG48 allowed mPD-L1 to bind to mPD-1 even in the presence of mCD80, thereby suppressing T cell activation.

Investigation was made on whether TKMG48 could allow PD-L1 to induce the inhibitory effect of PD-1 when CD80 and PD-L1 were present on the same antigen-presenting cells. PD-1-expressing or PD-1-deficient DO11.10 T cells were stimulated with IIAdL1-CD80/CD86 or IIAdL1-CD80/CD86/PD-L1 cells pulsed with OVA$_{323-339}$. Anti-mouse CD80 antibodies or control IgG (5 µg/ml) were added as shown in FIG. 46. The results are shown in FIG. 46. IL-2 production by antigen-stimulated DO11.10 T cells was inhibited by PD-1 when TKMG48 was added, but was not inhibited when 16-10A1 or IG10 was added. These results indicate that TKMG48 dissociates the interaction between cis-PD-L1 and CD80, allowing PD-L1 to induce the inhibitory effect of PD-1.

The therapeutic effect of TKMG48 on experimental autoimmune encephalomyelitis (EAE) was evaluated. C57BL/6N mice were inoculated with CFA-emulsified MOG$_{35-55}$ peptide as an antigen (day 0). 500 µg of TKMG48 or isotype control (mouse IgG1) was intraperitoneally administered to mice on days 1, 3, 5, 7, 10, and 13. The results are shown in FIG. 47. Treatment with TKMG48 significantly reduced the symptoms of EAE. Similarly, C57BU6N mice and C57BL/6N-Cd274$^{-/-}$ mice (PD-L1 knockout mice) were inoculated with CFA-emulsified MOG$_{35-55}$ peptide as antigen (day 0). 500 µg of TKMG48 or isotype control (mouse IgG1) was intraperitoneally administered to mice on days 1, 3, 5, 7, 10, 13, and 16. The results are shown in FIG. 48. Treatment with TKMG48 significantly reduced EAE symptoms in a PD-L1-dependent manner. These results indicate that the activation of the PD-1 signal by dissociation of the interaction between cis-PD-L1 and CD80 is effective in the treatment of an autoimmune disease.

Investigation was made on whether TKMF5 as an anti-human CD80 antibody could allow human PD-1-EC to bind to human PD-L1 when human CD80 and human PD-L1 were present on the same antigen-presenting cells. DOdKO-hPD-L1/hCD80 cells were pretreated with TKMF5 for 20 minutes at 37° C., followed by staining with human PD-1-EC. The binding of PD-1-EC to DOdKO-hPD-L1/hCD80 cells increases depending on the concentration of TKMF5. For example, the ratio of cells that bound to PD-1-EC in the presence of 30 µg/mL TKMF5 was about 50%. This result indicates that TKMF5 binds human PD-1-EC to human PD-L1 when human CD80 and human PD-L1 are present on the same antigen-presenting cell.

The effects of TKMF5 on the interaction between CD80 and CD28, the interaction between CD80 and CTLA-4, and the interaction between CD80 and PD-L1 were investigated. PD-1 gene-deficient DO11.10 T cells (DOdPD cells) were transfected with human CD80 to obtain DOdPD-hCD80 cells. DOdPD-hCD80 cells were pretreated with 10 µg/ml TKMF5 for 20 minutes at 4° C., followed by staining with human CD28-EC, human CTLA-4-EC, or human PD-L1-EC. In DOdPD-hCD80 cells pretreated with TKMF5, the intensity of the binding between human CD80 and human CD28-EC, and the binding between human CD80 and human CTLA-4-EC, were 80% or more of that of the untreated control, whereas the intensity of binding between human CD80 and human PD-1-EC was 10% or less of that of the untreated control. This result indicates that TKMF5 inhibits the binding of human PD-L1-EC to human CD80, but does not inhibit the binding of human CD28-EC and human CTLA-4-EC to human CD80.

Figure 49:
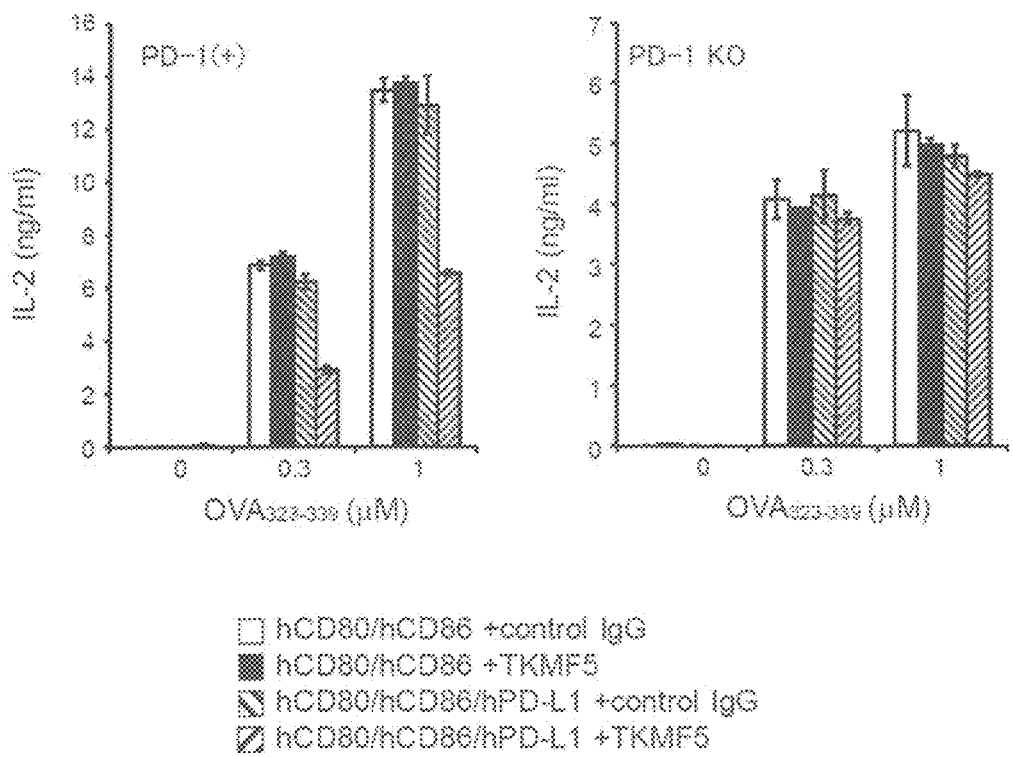
FIG. 49 shows that the addition of the anti-human CD80 antibody TKMF5 allowed hPD-L1 to bind to hPD-1 even in the presence of hCD80, thereby suppressing T cell activation.

Investigation was made on whether TKMF5 could allow PD-L1 to induce the inhibitory effect of PD-1 when CD80 and PD-L1 were on the same antigen-presenting cells. IIAdL1-hCD80/hCD86 or IIAdL1-hCD80/hCD86/hPD-L1 cells pulsed with OVA peptide were cultured in the presence of TKMF5 or isotype control IgG (10 µg/ml) along with PD-1-expressing or PD-1-deficient DO11.10 cells. The results are shown in FIG. 49. Addition of TKMF5 induced TCR-induced inhibition of IL-2 production in PD-1 expressing DO11.10 T cells, but did not induced the same in PD-1 deficient cells. These results indicate that TKMF5 dissociates the interaction between cis-hPD-L1 and hCD80 on antigen-presenting cells, allowing PD-L1 to induce the inhibitory effect of PD-1.

Figure 50:
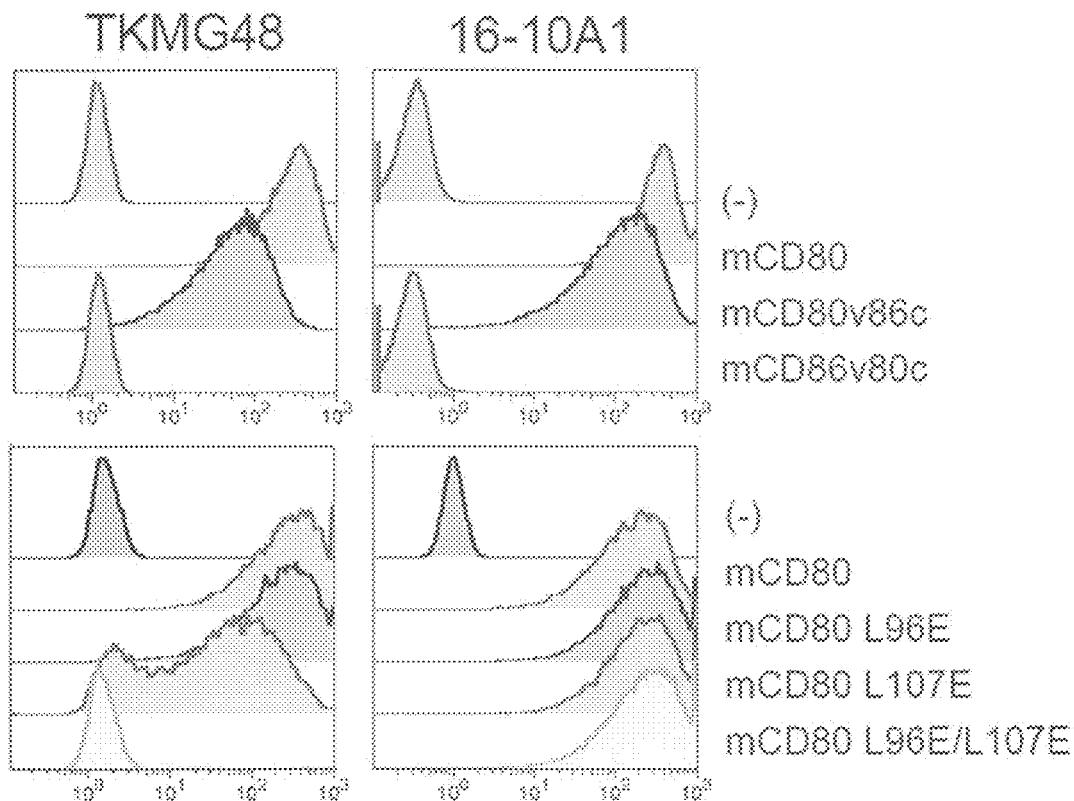
FIG. 50 shows that the anti-mouse CD80 antibody TKMG48 had low binding to CD80 mutants lacking the ability to bind PD-L1. 16-10A1 is a commercially available anti-mouse CD80 antibody.

FIG. 50 shows the results of evaluation by flow cytometry of the bindings of TKMG48 (left) and 16-10A1 (right) to DOdKO cells transfected with mouse CD80, chimeric molecules in which the IgV and IgC domains of CD80 and CD86 were swapped (see FIG. 13) (upper row), or mouse CD80 mutant lacking the binding ability to mouse PD-L1 (having L96E and/or L107E mutation) (lower row). TKMG48 and 16-10A1 recognized the IgV region of CD80 (upper). The binding of TKMG48 to the CD80 mutant lacking the ability to bind to PD-L1 was low (left). On the other hand, 16-10A1 showed the binding to the CD80 mutant lacking the ability of binding to PD-L1, comparable to that to the wild-type CD80 (right).

FIG. 51 shows the results of evaluation by flow cytometry of the bindings of TKMF5 (left) and 2D10 (right) to DOdKO cells transfected with human CD80, or a human CD80 mutant (having I92E and L104E mutations) lacking the ability to bind to human PD-L1. The binding of TKMF5 to the human CD80 mutant lacking the ability to bind to human PD-L1 was significantly low (left). On the other hand, 2D10 showed the binding to the human CD80 mutant lacking the ability to bind to human PD-L1, comparable to that to the wild-type human CD80 (right).

The binding affinity of the anti-mouse CD80 antibody (TKMG48) and the anti-human CD80 antibody (TKMF5) against mouse CD80 or human CD80 was evaluated. As a result, TKMG48 had an equilibrium dissociation constant (KD) of 1.232 nmol/L, and TKMF5 had an equilibrium dissociation constant (KD) of 11.44 nmol/L.

INDUSTRIAL APPLICABILITY

The substance of the present invention that promotes the binding of PD-L1 to PD-1 and is selected from an anti-CD80 antibody and an anti-PD-L1 antibody is useful as an immunosuppressive agent, or is useful for preventing and/or treating or an autoimmune disease, an allergic disease or a graft-versus-host disease.

The invention claimed is:

1. An anti-CD80 antibody comprising:
a heavy chain variable region that includes a heavy chain CDR1 including the amino acid sequence of SEQ ID NO: 9, a heavy chain CDR2 including the amino acid sequence of SEQ ID NO: 10, and a heavy chain CDR3 including the amino acid sequence of SEQ ID NO: 11, and
a light chain variable region that includes a light chain CDR1 including the amino acid sequence of SEQ ID NO: 12, a light chain CDR2 including the amino acid sequence of SEQ ID NO: 13, and a light chain CDR3 including the amino acid sequence of SEQ ID NO: 14.

2. An immunosuppressive agent comprising the antibody according to claim 1 as an active ingredient.

3. A therapeutic agent for an autoimmune disease, an allergic disease, or a graft-versus-host disease, comprising the antibody according to claim 1 as an active ingredient.

4. The anti-CD80 antibody according to claim 1, wherein the anti-CD80 antibody includes:
a heavy chain variable region that includes an amino acid sequence having an identity of 90% or more with the amino acid sequence of SEQ ID NO: 7; and
a light chain variable region that includes an amino acid sequence having an identity of 90% or more with the amino acid sequence of SEQ ID NO: 8.

5. An immunosuppressive agent comprising the antibody according to claim 4 as an active ingredient.

6. A therapeutic agent for an autoimmune disease, an allergic disease, or a graft-versus-host disease, comprising the antibody according to claim 4 as an active ingredient.

7. An anti-CD80 antibody comprising:
a heavy chain variable region that includes a heavy chain CDR1 including the amino acid sequence of SEQ ID NO: 17, a heavy chain CDR2 including the amino acid sequence of SEQ ID NO: 18, and a heavy chain CDR3 including the amino acid sequence of SEQ ID NO: 19, and
a light chain variable region that includes a light chain CDR1 including the amino acid sequence of SEQ ID NO: 20, a light chain CDR2 including the amino acid sequence of SEQ ID NO: 21, and a light chain CDR3 including the amino acid sequence of SEQ ID NO: 22.

8. An immunosuppressive agent comprising the antibody according to claim 7 as an active ingredient.

9. A therapeutic agent for an autoimmune disease, an allergic disease, or a graft-versus-host disease, comprising the antibody according to claim 7 as an active ingredient.

10. The anti-CD80 antibody according to claim 7, wherein the anti-CD80 antibody includes:
a heavy chain variable region that includes an amino acid sequence having an identity of 90% or more with the amino acid sequence of SEQ ID NO: 15; and
a light chain variable region that includes an amino acid sequence having an identity of 90% or more with the amino acid sequence of SEQ ID NO: 16.

11. An immunosuppressive agent comprising the antibody according to claim 10 as an active ingredient.

12. A therapeutic agent for an autoimmune disease, an allergic disease, or a graft-versus-host disease, comprising the antibody according to claim 10 as an active ingredient.

* * * * *

UNITED STATES PATENT AND TRADEMARK OFFICE
CERTIFICATE OF CORRECTION

| | | |
|---|---|---|
| PATENT NO. | : 12,234,289 B2 | Page 1 of 1 |
| APPLICATION NO. | : 17/311148 | |
| DATED | : February 25, 2025 | |
| INVENTOR(S) | : Taku Okazaki et al. | |

It is certified that error appears in the above-identified patent and that said Letters Patent is hereby corrected as shown below:

On the Title Page

Column 1, Line 1, (54) Title, delete "IMMUNOSUPPRESIVE" and insert --IMMUNOSUPPRESSIVE-- therefor; and In the Specification Column 1, Line 1, Title, delete "IMMUNOSUPPRESIVE" and insert --IMMUNOSUPPRESSIVE-- therefor.

Signed and Sealed this
Sixth Day of May, 2025

Coke Morgan Stewart
*Acting Director of the United States Patent and Trademark Office*